United States Patent
Smith et al.

(10) Patent No.: US 11,583,528 B2
(45) Date of Patent: Feb. 21, 2023

(54) FFA1 (GPR40) AS A THERAPEUTIC TARGET FOR NEURAL ANGIOGENESIS DISEASES OR DISORDERS

(71) Applicant: Children's Medical Center Corporation, Boston, MA (US)

(72) Inventors: Lois Smith, West Newton, MA (US); Jean-Sebastien Joyal, Boston, MA (US)

(*) Notice: Subject to any disclaimer, the term of this patent is extended or adjusted under 35 U.S.C. 154(b) by 218 days.

(21) Appl. No.: 15/999,535

(22) PCT Filed: Feb. 17, 2017

(86) PCT No.: PCT/US2017/018418
§ 371 (c)(1),
(2) Date: Aug. 17, 2018

(87) PCT Pub. No.: WO2017/143220
PCT Pub. Date: Aug. 24, 2017

(65) Prior Publication Data
US 2021/0322414 A1    Oct. 21, 2021

Related U.S. Application Data

(60) Provisional application No. 62/296,252, filed on Feb. 17, 2016.

(51) Int. Cl.
| | | |
|---|---|---|
| *A61K 31/513* | (2006.01) |
| *A61K 31/352* | (2006.01) |
| *A61K 31/519* | (2006.01) |
| *G01N 33/50* | (2006.01) |

(52) U.S. Cl.
CPC .......... *A61K 31/513* (2013.01); *A61K 31/352* (2013.01); *A61K 31/519* (2013.01); *G01N 33/5044* (2013.01); *G01N 2800/164* (2013.01); *G01N 2800/50* (2013.01)

(58) Field of Classification Search
CPC ............. A61K 31/513; G01N 33/5044; G01N 2800/164; G01N 2800/50
See application file for complete search history.

(56) References Cited

U.S. PATENT DOCUMENTS

| | | |
|---|---|---|
| 4,853,224 A | 8/1989 | Wong |
| 4,863,457 A | 9/1989 | Lee |
| 4,997,652 A | 3/1991 | Wong |
| 5,098,443 A | 3/1992 | Parel et al. |
| 5,139,941 A | 8/1992 | Muzyczka et al. |
| 5,185,152 A | 2/1993 | Peyman |
| 5,252,479 A | 10/1993 | Srivastava |
| 5,378,475 A | 1/1995 | Smith et al. |
| 5,443,505 A | 8/1995 | Wong et al. |
| 5,554,187 A | 9/1996 | Rizzo |
| 5,710,182 A | 1/1998 | Reunamaeki et al. |
| 5,725,493 A | 3/1998 | Avery et al. |
| 2006/0252107 A1 | 11/2006 | Kubota et al. |
| 2009/0012093 A1 | 1/2009 | Fukatsu et al. |
| 2011/0318424 A1 | 12/2011 | Cepko et al. |
| 2013/0096165 A1 | 4/2013 | He et al. |
| 2013/0165501 A1 | 6/2013 | Purschke et al. |

FOREIGN PATENT DOCUMENTS

| | | |
|---|---|---|
| CN | 1735408 A | 2/2006 |
| CN | 102076670 A | 5/2011 |
| WO | WO 90/11092 A1 | 10/1990 |
| WO | WO 93/24641 A2 | 12/1993 |
| WO | WO 94/13788 A1 | 6/1994 |
| WO | WO 94/24983 A2 | 11/1994 |
| WO | WO 2004/106276 A1 | 12/2004 |
| WO | 2005050225 A2 | 6/2005 |
| WO | WO 2005/051890 A1 | 6/2005 |
| WO | WO 2005/087710 A1 | 9/2005 |
| WO | WO 2017/143220 A1 | 8/2017 |

OTHER PUBLICATIONS

Li, Chao, et al. "Biochemical alterations in the retinas of very low-density lipoprotein receptor knockout mice: an animal model of retinal angiomatous proliferation." Archives of ophthalmology, 125(6): 795-803 (2007).
Vanhoutte et al., "Human Safety, Pharmacokinetics and Pharmacodynamics of the Gpr84 Antagonist Glpg1205, a Potential New Approach to Treat IBD," United European Gastroenterology Journal, 2(1 Supplement):A132-A605, Poster P0341 (2014).
Prihandoko et al. "Distinct phosphorylation clusters determines the signalling outcome of the free fatty acid receptor 4/G Protein-Coupled Receptor 120." Molecular pharmacology, 89(5):505-20 (2016).
International Search Report dated Jul. 19, 2017 issued in corresponding PCT/US2017/018418.
Alquier et al., Deletion of GPR40 impairs glucose-induced insulin secretion in vivo in mice without affecting intracellular fuel metabolism in islets. Diabetes. Nov. 2009;58(11):2607-15. doi: 10.2337/db09-0362. Epub Aug. 31, 2009.
Al-Ubaidi et al., Bilateral retinal and brain tumors in transgenic mice expressing simian virus 40 large T antigen under control of the human interphotoreceptor retinoid-binding protein promoter. J Cell Biol. Dec. 1992;119(6):1681-7. doi: 10.1083/jcb.119.6.1681.
Anderson, W.F. Human gene therapy. Nature. Apr. 3, 1998;392(6679 Suppl):25-30. doi: 10.1038/32058.

(Continued)

*Primary Examiner* — Sahar Javanmard
(74) *Attorney, Agent, or Firm* — Wolf, Greenfield & Sacks, P.C.

(57) ABSTRACT

The instant invention provides methods and compositions related to discovery of Free Fatty Acid Receptor 1 (FFA1) as a therapeutic target for treatment or prevention of diseases or disorders of neurons that are characterized by angiogenesis, or of vascular diseases of the eye, retinal degeneration and/or tumors more generally. Therapeutic and/or prophylactic uses and compositions of known FFA1 inhibitors, including small molecules and nucleic acid agents, are described. Methods for identification of novel FFA1 inhibitors are also provided.

15 Claims, 36 Drawing Sheets

Specification includes a Sequence Listing.

(56) References Cited

OTHER PUBLICATIONS

Barot et al., Mitochondrial dysfunction in retinal diseases. Curr Eye Res. Dec. 2011;36(12):1069-77. doi: 10.3109/02713683.2011. 607536. Epub Oct. 6, 2011. Author Manuscript. 16 pages.

Bottoni et al., Treatment of retinal angiomatous proliferation in age-related macular degeneration: a series of 104 cases of retinal angiomatous proliferation. Arch Ophthalmol. Dec. 2005;123(12):1644-50. doi: 10.1001/archopht.123.12.1644.

Briscoe et al., The orphan G protein-coupled receptor GPR40 is activated by medium and long chain fatty acids. J Biol Chem. Mar. 28, 2003;278(13):11303-11. doi: 10.1074/jbc.M211495200. Epub Dec. 19, 2002.

Briscoe et al., Pharmacological regulation of insulin secretion in MIN6 cells through the fatty acid receptor GPR40: identification of agonist and antagonist small molecules. Br J Pharmacol. Jul. 2006;148(5):619-28. doi: 10.1038/sj.bjp.0706770. Epub May 15, 2006.

Cahill, G.F., Starvation in man. N Engl J Med. Mar. 19, 1970;282(12):668-75. doi: 10.1056/NEJM197003192821209. PMID: 4915800.

Calvano et al., A network-based analysis of systemic inflammation in humans. Nature. Oct. 13, 2005;437(7061):1032-7. doi: 10.1038/nature03985. Epub Aug. 31, 2005. Erratum in: Nature. Dec. 1, 2005;438(7068):696.

Chen et al., Photoreceptor degeneration and retinal inflammation induced by very low-density lipoprotein receptor deficiency. Microvasc Res. Jun. 2009;78(1):119-27. doi: 10.1016/j.mvr.2009.02.005. Epub Mar. 10, 2009. Author Manuscript. 20 pages.

Choi et al., Effects of adeno-associated virus DNA hairpin structure on recombination. J Virol. Jun. 2005;79(11):6801-7. doi: 10.1128/JVI.79.11.6801-6807.2005.

Cohen et al., Glucose catabolism of rabbit retina before and after development of visual function. J Neurochem. May 1960;5:253-76. doi: 10.1111/j.1471-4159.1960.tb13363.x.

Curiel et al., High-efficiency gene transfer mediated by adenovirus coupled to DNA-polylysine complexes. Hum Gene Ther. Apr. 1992;3(2): 147-54. doi: 10.1089/hum.1992.3.2-147.

Daniel et al., Outcomes in Eyes with Retinal Angiomatous Proliferation in the Comparison of Age-Related Macular Degeneration Treatments Trials (CATT). Ophthalmology. Mar. 2016;123(3):609-16. doi: 10.1016/j.ophtha.2015.10.034. Epub Dec. 8, 2015. Author Manuscript. 17 pages.

Deerinck et al., T., Enhancing Serial Block-Face Scanning Electron Microscopy to Enable High Resolution 3-D Nanohistology of Cells and Tissues. Microscopy and Microanalysis. Aug. 2010; 16(S2), 1138-1139. doi:10.1017/S1431927610055170.

Dinculescu et al., Adeno-associated virus-vectored gene therapy for retinal disease. Hum Gene Ther. Jun. 2005;16(6):649-63. doi: 10.1089/hum.2005.16.649.

Dornburg, R., Reticuloendotheliosis viruses and derived vectors. Gene Ther. Jul. 1995;2(5):301-10.

Dorrell et al., MI, Antioxidant or neurotrophic factor treatment preserves function in a mouse model of neovascularization-associated oxidative stress. J Clin Invest. Mar. 2009;119(3):611-23. doi: 10.1172/JCI35977. Epub Feb. 2, 2009.

Eglitis et al., Retroviral vectors for introduction of genes into mammalian cells. Biotechniques. Jul.-Aug 1988;6(7):608-14.

Feehan et al., Identifying subtypes of patients with neovascular age-related macular degeneration by genotypic and cardiovascular risk characteristics. BMC Med Genet. Jun. 17, 2011;12:83. doi: 10.1186/1471-2350-12-83.

Felgner et al., Lipofection: a highly efficient, lipid-mediated DNA-transfection procedure. Proc Natl Acad Sci U S A. Nov. 1987;84(21):7413-7. doi: 10.1073/pnas.84.21.7413.

Ferrannini et al., Effect of fatty acids on glucose production and utilization in man. J Clin Invest. Nov. 1983;72(5):1737-47. doi: 10.1172/JCI111133.

Fisher et al., Transduction with recombinant adeno-associated virus for gene therapy is limited by leading-strand synthesis. J Virol. Jan. 1996;70(1):520-32. doi: 10.1128/JVI.70.1.520-532.1996.

Fletcher et al., Observations regarding retinopathy in mitochondrial trifunctional protein deficiencies. Mol Genet Metab. May 2012;106(1):18-24. doi: 10.1016/j.ymgme.2012.02.015. Epub Mar. 8, 2012. Author Manuscript. 16 pages.

Fritsche et al., Age-related macular degeneration is associated with an unstable ARMS2 (LOC387715) mRNA. Nat Genet. Jul. 2008;40(7):892-6. doi: 10.1038/ng.170. Epub May 30, 2008.

Fukushima et al., Different roles of GPR120 and GPR40 in the acquisition of malignant properties in pancreatic cancer cells. Biochemical and Biophysical Research Communications. Aug. 2015;465(3):512-515.

Furukawa et al., Crx, a novel otx-like homeobox gene, shows photoreceptor-specific expression and regulates photoreceptor differentiation. Cell. Nov. 14, 1997;91(4):531-41. doi: 10.1016/s0092-8674(00)80439-0.

GenBank Submission: NIH/NCBI Accession No. NM_005303.2, Minami et al., Jun. 21, 2021. 4 pages.

GenBank Submission: NIH/NCBI Accession No. NP_005294.1., Guzman-Silva et al., Jun. 11, 2022. 4 pages.

Gospe et al., Facilitative glucose transporter Glut1 is actively excluded from rod outer segments. J Cell Sci. Nov. 1, 2010; 123(Pt 21):3639-44. doi: 10.1242/jcs.072389. Epub Oct. 5, 2010.

Goudriaan et al., The VLDL receptor plays a major role in chylomicron metabolism by enhancing LPL-mediated triglyceride hydrolysis. J Lipid Res. Aug. 2004;45(8):1475-81. doi: 10.1194/jlr.M400009-JLR200. Epub May 16, 2004.

Grieger et al., Samulski RJ. Production and characterization of adeno-associated viral vectors. NatProtoc. 2006;1(3):1412-28. doi: 10.1038/nprot.2006.207.

Hardy et al., Oleate promotes the proliferation of breast cancer cells via the G protein-coupled receptor GPR40. J Biol Chem. Apr. 8, 2005;280(14):13285-91. doi: 10.1074/jbc.M410922200. Epub Feb. 4, 2005.

Honoré et al., Fatty acid receptor Gpr40 mediates neuromicrovascular degeneration induced by transarachidonic acids in rodents. Arterioscler Thromb Vase Biol. May 2013;33(5):954-61. doi: 10.1161/ATVBAHA. 112.300943. Epub Mar. 21, 2013.

Hu et al., Expression of VLDLR in the retina and evolution of subretinal neovascularization in the knockout mouse model's retinal angiomatous proliferation. Invest Ophthalmol Vis Sci. Jan. 2008;49(1):407-15. doi: 10.1167/iovs.07-0870.

Hua et al., Resveratrol inhibits pathologic retinal neovascularization in Vldlr(−/−) mice. Invest Ophthalmol Vis Sci. Apr. 25, 2011;52(5):2809-16. doi: 10.1167/iovs.10-6496.

Itoh et al., Free fatty acids regulate insulin secretion from pancreatic beta cells through GPR40. Nature. Mar. 13, 2003;422(6928):173-6. doi: 10.1038/nature01478. Epub Feb. 23, 2003.

Jain et al., Metabolite profiling identifies a key role for glycine in rapid cancer cell proliferation. Science. May 25, 2012;336(6084):1040-4. doi: 10.1126/science.1218595.

Joyal et al., Retinal lipid and glucose metabolism dictates angiogenesis through the lipid sensor Ffar1. Nat Med. Apr. 2016;22(4):439-45. doi: 10.1038/nm.4059. Epub Mar. 14, 2016. Erratum in: Nat Med. Jun. 7, 2016;22(6):692. Author Manuscript. 24 pages.

Kaelin, WG Jr., Cancer and altered metabolism: potential importance of hypoxia-inducible factor and 2-oxoglutarate-dependent dioxygenases. Cold Spring Harb Symp Quant Biol. 2011;76:335-45. doi: 10.1101/sqb.2011.76.010975. Epub Nov. 16, 2011.

Kebede et al., The fatty acid receptor GPR40 plays a role in insulin secretion in vivo after high-fat feeding. Diabetes. Sep. 2008;57(9):2432-7. doi: 10.2337/db08-0553. Epub Jun. 16, 2008. Erratum in: Diabetes. Nov. 2008;57(11):3166.

Khani et al., AAV-mediated expression targeting of rod and cone photoreceptors with a human rhodopsin kinase promoter. Invest Ophthalmol Vis Sci. Sep. 2007;48(9):3954-61. doi: 10.1167/iovs. 07-0257.

Klepper, J., Glucose transporter deficiency syndrome (GLUT1DS) and the ketogenic diet. Epilepsia. Nov. 2008;49 Suppl 8:46-9. doi: 10.1111/j.1528-1167.2008.01833.x.

Komáromy et al., Targeting gene expression to cones with human cone opsin promoters in recombinant AAV. Gene Ther. Jul. 2008;15(14):1049-55. doi: 10.1038/gt.2008.32. Epub Mar. 13, 2008.

(56) References Cited

OTHER PUBLICATIONS

Erratum in: Gene Ther. Jul. 2008;15(14):1073. Glushakova, L G [added]. Erratum in: Gene Ther. Dec. 2011;18(12):1179. Author Manuscript. 17 Pages.

Lebherz et al., Novel AAV serotypes for improved ocular gene transfer. J Gene Med. Apr. 2008;10(4):375-82. doi: 10.1002/jgm.1126. Author Manuscript. 16 pages.

Lefebvre et al., Sorting out the roles of PPAR alpha in energy metabolism and vascular homeostasis. J Clin Invest. Mar. 2006;116(3):571-80. doi: 10.1172/JCI27989.

Lim et al., Age-related macular degeneration. Lancet. May 5, 2012;379(9827):1728-38. doi: 10.1016/S0140-6736( 12)60282-7.

Lopaschuk et al., Myocardial fatty acid metabolism in health and disease. Physiol Rev. Jan. 2010;90(1):207-58. doi: 10.1152/physrev.00015.2009.

Mantych et al., Characterization of glucose transporter isoforms in the adult and developing human eye. Endocrinology. Aug. 1993;133(2):600-7. doi: 10.1210/endo.133.2.8344201.

Miller, A.D., Retrovirus packaging cells. Hum Gene Ther. 1990 Spring;1(1):5-14. doi: 10.1089/hum.1990.1.1-5.

Naik et al., Safety, tolerability, pharmacokinetics, and pharmacodynamic properties of the GPR40 agonist TAK-875: results from a double-blind, placebo-controlled single oral dose rising study in healthy volunteers. J Clin Pharmacol. Jul. 2012;52(7):1007-16. doi: 10.1177/0091270011409230. Epub May 24, 2011.

Nakamura et al., Regulation of energy metabolism by long-chain fatty acids. Prog Lipid Res. Jan. 2014;53:124-44. doi: 10.1016/j.plipres.2013.12.001. Epub Dec. 18, 2013.

Nehra et al., Docosahexaenoic acid, G protein-coupled receptors, and melanoma: is G protein-coupled receptor 40 a potential therapeutic target? J Surg Res. May 15, 2014;188(2):451-8. doi: 10.1016/j.jss.2014.01.037. Epub Jan. 29, 2014. Author Manuscript. 18 pages.

Niu et al., Very-low-density lipoprotein: complex particles in cardiac energy metabolism. J Lipids. 2011;2011:189876. doi: 10.1155/2011/189876. Epub Jul. 3, 2011.

Obunike et al., Transcytosis of lipoprotein lipase across cultured endothelial cells requires both heparan sulfate proteoglycans and the very low density lipoprotein receptor. J Biol Chem. Mar. 23, 2001;276(12):8934-41. doi: 10.1074/jbc.M008813200. Epub Dec. 19, 2000.

Ohno-Matsui et al., Inducible expression of vascular endothelial growth factor in adult mice causes severe proliferative retinopathy and retinal detachment. Am J Pathol. Feb. 2002;160(2):711-9. doi: 10.1016/S0002-9440(10)64891-2.

Okawa et al., ATP consumption by mammalian rod photoreceptors in darkness and in light. Curr Biol. Dec. 23, 2008;18(24):1917-21. doi: 10.1016/j.cub.2008.10.029. Epub Dec. 11, 2008.

Park et al., AsiDesigner: exon-based siRNA design server considering alternative splicing. Nucleic Acids Res. Jul. 1, 2008;36:W97-103. doi: 10.1093/nar/gkn280. Epub May 14, 2008.

Samulski et al., A recombinant plasmid from which an infectious adeno-associated virus genome can be excised in vitro and its use to study viral replication. J Virol. 1987 Oct.;61(10):3096-101. doi: 10.1128/JVI.61.10.3096-3101.1987.

Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.

Sarac et al., Neuro-ophthalmologic findings in humans with quadrupedal locomotion. Ophthalmic Genet. Dec. 2012;33(4):249-52. doi: 10.3109/13816810.2012.689412. Epub Jun. 11, 2012.

Semple-Rowland et al., Targeted expression of two proteins in neural retina using self-inactivating, insulated lentiviral vectors carrying two internal independent promoters. Mol Vis. Oct. 18, 2007;13:2001-11.

Smyth et al., A novel, evolutionarily conserved enhancer of cone photoreceptor-specific expression. J Biol Chem. Apr. 18, 2008;283(16):10881-91. doi: 10.1074/jbc.M710454200. Epub Feb. 13, 2008.

Spahis et al., Plasma fatty acid composition in French-Canadian children with non-alcoholic fatty liver disease: Effect of n-3 PUFA supplementation. Prostaglandins Leukot Essent Fatty Acids. Aug. 2015;99:25-34. doi: 10.1016/j.plefa.2015.04.010. Epub May 8, 2015.

Stahl et al., Computer-aided quantification of retinal neovascularization. Angiogenesis. 2009;12(3):297-301. doi: 10.1007/s10456-009-9155-3. Author Manuscript. 10 pages.

Stahl et al., Postnatal weight gain modifies severity and functional outcome of oxygen-induced proliferative retinopathy. Am J Pathol. Dec. 2010;177(6):2715-23. doi: 10.2353/ajpath.2010.100526. Epub Nov. 5, 2010.

Steneberg et al., The FFA receptor GPR40 links hyperinsulinemia, hepatic steatosis, and impaired glucose homeostasis in mouse. Cell Metab. Apr. 2005;1(4):245-58. doi: 10.1016/j.cmet.2005.03.007.

Sun et al., DC260126: a small-molecule antagonist of GPR40 that protects against pancreatic β-Cells dysfunction in db/db mice. PLoS One. Jun. 11, 2013;8(6):e66744. doi: 10.1371/journal.pone.0066744.

Tan et al., Expression of cone-photoreceptor-specific antigens in a cell line derived from retinal tumors in transgenic mice. Invest Ophthalmol Vis Sci. Mar. 2004;45(3):764-8. doi: 10.1167/iovs.03-1114.

Townsend et al., Reproducibility of metabolomic profiles among men and women in 2 large cohort studies. Clin Chem. Nov. 2013;59(11):1657-67. doi: 10.1373/clinchem.2012.199133. Epub Jul. 29, 2013.

Trick et al., Retinal oxygenation response and retinopathy. Prog Retin Eye Res. Mar. 2005;24(2):259-74. doi: 10.1016/j.preteyeres.2004.08.001.

Tsujihata et al., TAK-875, an orally available G protein-coupled receptor 40/free fatty acid receptor 1 agonist, enhances glucose-dependent insulin secretion and improves both postprandial and fasting hyperglycemia in type 2 diabetic rats. J Pharmacol Exp Ther. Oct. 2011;339(1):228-37. doi: 10.1124/jpet.111.183772. Epub Jul. 11, 2013.

Tyni et al., Mitochondrial fatty acid beta-oxidation in the human eye and brain: implications for the retinopathy of long-chain 3-hydroxyacyl-CoA dehydrogenase deficiency. Pediatr Res. Nov. 2004;56(5):744-50. doi: 10.1203/01.PDR.0000141967.52759.83. Epub Sep. 3, 2004.

Vandenberghe et al., Efficient serotype-dependent release of functional vector into the culture medium during adeno-associated virus manufacturing. Hum Gene Ther. Oct. 2010;21(10):1251-7. doi: 10.1089/hum.2010.107.

Wagner et al., Transferrin-polycation conjugates as carriers for DNA uptake into cells. Proc Natl Acad Sci U S A. May 1990;87(9):3410-4. doi: 10.1073/pnas.87.9.3410.

Warburg, O., On the origin of cancer cells. Science. Feb. 24, 1956;123(3191):309-14. doi: 10.1126/science.123.3191.309.

Wauson et al., Minireview: Nutrient sensing by G protein-coupled receptors. Mol Endocrinol. Aug. 2013;27(8):1188-97. doi: 10.1210/me.2013-1100. Epub Jul. 2, 2013.

Winkler, B.S., Glycolytic and oxidative metabolism in relation to retinal function. J Gen Physiol. Jun. 1981;77(6):667-92. doi: 10.1085/jgp.77.6.667.

Wong-Riley, M.T., Energy metabolism of the visual system. Eye Brain. 2010;2:99-116. doi: 10.2147/EB.S9078. Epub Jul. 22, 2010.

Wu et al., Adeno-associated virus serotypes: vector toolkit for human gene therapy. Mol Ther. Sep. 2006;14(3):316-27. doi: 10.1016/j.ymthe.2006.05.009. Epub Jul. 7, 2006.

Xia et al., siRNA-mediated gene silencing in vitro and in vivo. Nat Biotechnol. Oct. 2002;20(10):1006-10. doi: 10.1038/nbt739. Epub Sep. 16, 2002.

Yamashima et al., Dual effects of the non-esterified fatty acid receptor 'GPR40' for human health. Prog Lipid Res. Apr. 2015;58:40-50. doi: 10.1016/j.plipres.2015.01.002. Epub Jan. 20, 2015.

Yannuzzi et al., Idiopathic macular telangiectasia. Arch Ophthalmol. Apr. 2006;124(4):450-60. doi: 10.1001/archopht.124.4.450.

Yannuzzi et al., Idiopathic polypoidal choroidal vasculopathy (IPCV). 1990. Retina. Feb. 2012;32 Suppl 1:1-8.

Zhao et al., Glioma-derived mutations in IDH1 dominantly inhibit IDH1 catalytic activity and induce HIF-1alpha. Science. Apr. 10, 2009;324(5924):261-5. doi: 10.1126/science.1170944. Author Manuscript. 10 pages.

(56) References Cited

OTHER PUBLICATIONS

Zhou et al., Nanoceria inhibit the development and promote the regression of pathologic retinal neovascularization in the Vldlr knockout mouse. PLoS One. Feb. 22, 2011;6(2):e16733. doi: 10.1371/journal.pone.0016733.

AAV2-*hRK-shVldlr*

FIG. 10A
Molecular and Cellular Functions
| Name | P-value | # Molecules |
|---|---|---|
| Carbohydrate Metabolism | 3.14E-04-2.85E-02 | 43 |
| Molecular Transport | 3.14E-04-2.64E-02 | 48 |
| Cell Death | 4.95E-04-2.85E-02 | 346 |
| Cell Cycle | 5.24E-04-2.85E-02 | 189 |
| Cellular Compromise | 5.93E-04-2.85E-02 | 41 |
FIG. 10B
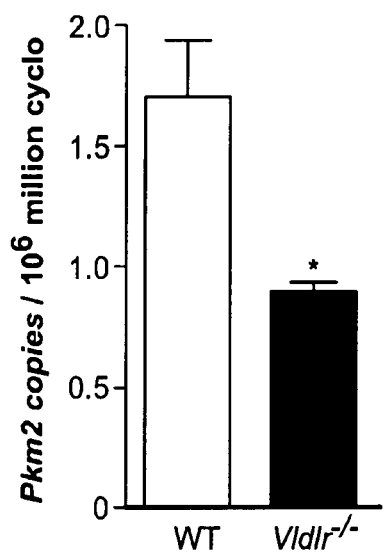
FIG. 10C
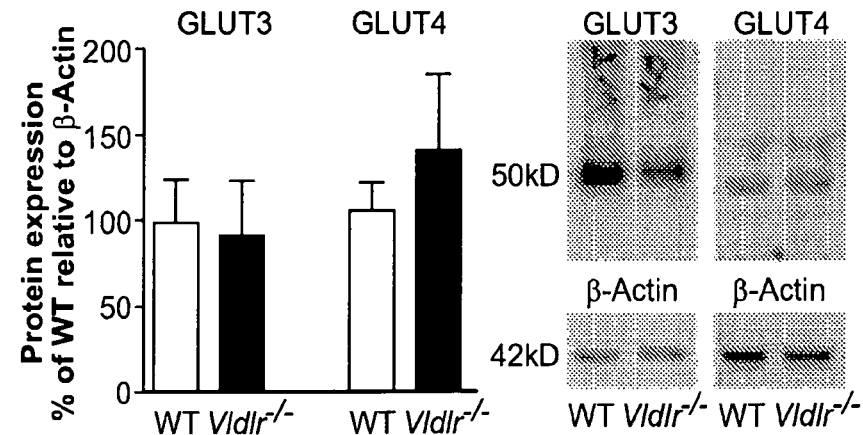

FFA1 (GPR40) AS A THERAPEUTIC TARGET FOR NEURAL ANGIOGENESIS DISEASES OR DISORDERS

RELATED APPLICATIONS

This application is a national stage application, filed under 35 U.S.C. § 371, of International Application No. PCT/US2017/018418, filed Feb. 17, 2017, which claims the benefit of priority under 35 U.S.C. § 119(e) to U.S. Provisional Application No. 62/296,252, filed Feb. 17, 2016, which is incorporated herein by reference in its entirety.

STATEMENT REGARDING FEDERALLY SPONSORED RESEARCH OR DEVELOPMENT

This invention was made with government support under NIH EY024868, EY017017, EY022275, P01 HD18655; Boston's Children's Hospital Ophthalmology Foundation and Faculty Career Development Award, Bright Focus Foundation, Mass Lions Eye Research Inc. NIH EY024963. The government has certain rights in the invention.

SEQUENCE LISTING

The instant application contains a Sequence Listing which has been submitted electronically in ASCII format and is hereby incorporated by reference in its entirety. Said ASCII copy, created on May 28, 2021, is named 048218-543N01US_SL.txt and is 8,879 bytes in size.

BACKGROUND OF THE INVENTION

Retinal neovascularization in the macula is the leading cause of blindness in older adults (Lim, L. S., et al., *Lancet* 379, 1728-1738 (2012)). Photoreceptors are amongst the highest energy consuming cells of the body (Wong-Riley, M. T. T. *Eye Brain* 2, 99-116 (2010), and Okawa, H., et al., *Curr Biol* 18, 1917-1921 (2008)) and the macula is the region of highest photoreceptor density.

Retinal angiomatous proliferation (RAP) vascular lesions are found in macular telangiectasia (MacTel) (Yannuzzi, L. A., et al. *Retina* 32 Suppl 1, 450460 (2012)) as well as in 15-20% of neovascular age-related macular degeneration (AMD) (Bottoni, F., et al. *Arch Ophthalmol* 123, 1644-1650 (2005)), consistent with high energy demands associated with retinal angiogenesis. Although VEGF contributes to neovascularization in macular diseases, the factors that initiate VEGF secretion remain largely unknown. Dyslipidimia and mitochondrial dysfunction (associated with aging) are important risk factors for neovascular AMD (Feehan, M., et al. *BMC Med Genet* 12, 83 (2011), Fritsche, L. G., et al. *Nat Genet* 40, 892-896 (2008), and Barot, M., et al., *Curr Eye Res* 36, 1069-1077 (2011)). There is currently no cure for AMD or MacTel. Therefore, there is a need in the field for the identification of therapeutics that ameliorate and/or prevent AMD and/or MacTel.

SUMMARY OF THE INVENTION

The invention is based, at least in part, upon the identification of Free Fatty Acid Receptor 1 (FFA1, also known as G protein-coupled receptor (GPR) 40-dependent (GPR40) protein) as a therapeutic target for neural cell (e.g., retinal cell) diseases and/or disorders that are characterized by angiogenesis. Targeting of FFA1 with one or more antagonists, including known antagonists such as GW1100, antisense and/or RNAi agents, for treatment or prevention of a disease or disorder of the eye (e.g., retina) characterized by angiogenesis is specifically contemplated. In certain aspects of the invention, it is also identified that targeting of FFA1 as described herein can exert a therapeutic effect for vascular diseases of the eye such as age-related macular degeneration (AMD) and retinopathy of prematurity (ROP), as well as for retinal degeneration and/or tumors in general. In related aspects, it is also identified herein that not only FFA1 (GPR40), but also, e.g., GPR84 and/or GPR 120 can be so targeted, with similar therapeutic effect.

Use of eye and/or retinal cells to screen for and identify additional compounds or agents that inhibit FFA1 is also contemplated. Without wishing to be bound by theory, inhibition of FFA1 is believed to exert a therapeutic effect by increasing glucose entry into the retina.

In one aspect, the invention provides a method for treating or preventing angiogenesis in neural cells of a subject and/or treating or preventing cancer in a subject, the method involving (a) identifying a subject having or at risk of neural cell angiogenesis and/or having or at risk of developing cancer; and (b) administering a FFA1 inhibitor to the subject, thereby treating or preventing angiogenesis in the neural cells of the subject and/or treating or preventing cancer in the subject.

In one embodiment, the neural cells are retinal cells, optionally photoreceptor cells.

Another aspect of the invention provides a method for treating or preventing retinal angiomatous proliferation (RAP) vascular lesions in a subject, the method involving (a) identifying a subject having or at risk of developing RAP vascular lesions; and (b) administering a FFA1 inhibitor to the subject, thereby treating or preventing RAP vascular lesions in the subject.

In certain embodiments, the subject has macular telangiectasia (MacTel) or neovascular age-related macular degeneration (AMD).

In one embodiment, the cells of the subject are impaired for lipid uptake, as compared to the cells of an appropriate control subject.

In another embodiment, the subject has dyslipidemia or mitochondrial dysfunction.

In an additional embodiment, the FFA1 inhibitor is a small molecule antagonist or an RNAi agent.

Optionally, the FFA1 antagonist is GW1100.

In certain embodiments, the FFA1 inhibitor is administered to the eye of the subject. Optionally, the FFA1 inhibitor is administered by intravitreal injection.

In another embodiment, administering the FFA1 inhibitor enhances GLUT1 expression in the retinal cells of the subject.

An additional aspect of the invention provides a method for increasing glucose uptake in a retinal cell, the method involving obtaining a retinal cell and contacting the retinal cell with a FFA1 inhibitor, thereby increasing glucose uptake in the retinal cell.

In one embodiment, the retinal cell is a retinal cell in vitro.

In certain embodiments, GLUT1 expression is enhanced in the retinal cell contacted with the FFA1 inhibitor.

Another aspect of the invention provides a method for identifying a test compound as a FFA1 inhibitor, the method involving contacting a retinal cell with a test compound; and measuring glucose uptake in the retinal cell, where measurement of increased glucose uptake in the retinal cell in the presence of the test compound identifies the test compound as a FFA1 inhibitor.

In certain embodiments, the retinal cell has a mutation or deletion of the very low-density lipoprotein receptor (Vldlr) gene that suppresses fatty acid uptake in the retinal cell.

In one embodiment, GLUT1 expression is enhanced in the retinal cell contacted with the test compound.

An additional aspect of the invention provides a method for treating or preventing a vascular disease of the eye, retinal degeneration and/or cancer in a subject, the method involving (a) identifying a subject having or at risk of developing a vascular disease of the eye, retinal degeneration and/or cancer; and (b) administering a GPR84 inhibitor to the subject, thereby treating or preventing the vascular disease of the eye, retinal degeneration and/or cancer in the subject.

In one embodiment, the GPR84 inhibitor is a small molecule antagonist or an RNAi agent.

In another embodiment, the GPR84 inhibitor is GLPG1205.

In certain embodiments, the vascular disease of the eye is age-related macular degeneration (AMD) or retinopathy of prematurity (ROP).

Another aspect of the invention provides a method for treating or preventing a vascular disease of the eye, retinal degeneration and/or cancer in a subject, the method involving (a) identifying a subject having or at risk of developing a vascular disease of the eye, retinal degeneration and/or cancer; and (b) administering a GPR120 inhibitor to the subject, thereby treating or preventing the vascular disease of the eye, retinal degeneration and/or cancer in the subject.

In certain embodiments, the GPR120 inhibitor is a small molecule antagonist or an RNAi agent.

In another embodiment, the GPR120 inhibitor is 4-Methyl-N-9H-xanthen-9-yl-benzenesulfonamide.

Definitions

Unless defined otherwise, all technical and scientific terms used herein have the meaning commonly understood by a person skilled in the art to which this invention belongs. The following references provide one of skill with a general definition of many of the terms used in this invention: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

An "agent" is meant any small compound, antibody, nucleic acid molecule, or peptide or fragment thereof. An "agent" includes a "therapeutic agent" as defined herein below.

As used herein, "Age-related macular degeneration," or "AMD" refers to an eye condition which causes a deterioration or breakdown of the macula, a small spot near the center of the retina and the part of the eye needed for sharp central vision. More specifically, the photoreceptor cells within the macula die off slowly, thus accounting for the progressive loss of vision.

By "ameliorate" is meant decrease, suppress, attenuate, diminish, arrest, or stabilize the development or progression of a disease.

An "agonist" as used herein is a molecule which enhances the biological function of a protein. The agonist may thereby bind to the target protein to elicit its functions. However, agonists which do not bind the protein are also envisioned. The agonist may enhance the biological function of the protein directly or indirectly. Agonists which increase expression of certain genes are envisioned within the scope of particular embodiments of the invention. Suitable agonists will be evident to those of skill in the art. For the present invention it is not necessary that the agonist enhances the function of the target protein directly. Rather, agonists are also envisioned which stabilize or enhance the function of one or more proteins upstream in a pathway that eventually leads to activation of targeted protein. Alternatively, the agonist may inhibit the function of a negative transcriptional regulator of the target protein, wherein the transcriptional regulator acts upstream in a pathway that eventually represses transcription of the target protein.

An "antagonist" may refer to a molecule that interferes with the activity or binding of another molecule, for example, by competing for the one or more binding sites of an agonist, but does not induce an active response.

Cancer, as used herein, can include the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Any compositions or methods provided herein can be combined with one or more of any of the other compositions and methods provided herein.

By "dyslipidemia" is meant by an abnormal amount of lipids in the blood. Dyslipidemias were traditionally classified by patterns of elevation in lipids and lipoproteins. A more practical system categorizes dyslipidemias as primary or secondary and characterizes them by increases in cholesterol only (pure or isolated hypercholesterolemia), increases in TGs only (pure or isolated hypertriglyceridemia), or increases in both cholesterol and TGs (mixed or combined hyperlipidemias).

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

"Free fatty acid receptor 1" or "Ffa1" is also referred to as GPR40, a class A G-protein couple receptor, encoded by the Ffar1 gene (NM_005303.2 mRNA; NP_005294.1 protein). FFA1 is natively activated by medium to long chain fatty acids.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Chitosan compositions are useful for the delivery of polynucleotides, such as inhibitory nucleic acid molecules, useful for the treatment or prevention of pathogen infection and related disease. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The term "macula" refers to a small area within the retina. The macula is the part of the retina that is responsible for central vision, allowing things to be seen clearly. Although only a small part of the retina, the macula is more sensitive to detail than the rest of the retina. Many older people develop macular degeneration as part of the body's natural aging process. Symptoms of macular degeneration include blurriness, dark areas or distortion in central vision, or even permanent loss in central vision. It usually does not affect side or peripheral vision.

The term, "mitochondrial disease" refers to a chronic, genetic disorder that occurs when the mitochondria of the cell fail to produce enough energy for cell or organ function. There are many forms of mitochondrial disease including, mitochondrial myopathy, diabetes mellitus, Leber's hereditary optic neuropathy, Leigh syndrome, neuropathy, ataxia, retinitis pigmentosa and ptosis (NARP), myoclonic epilepsy and ragged red fibers (MERRF) and mitochondrial myopathy, encephalomyopathy, lactic acidosis, stroke-like syndromes (MELAS).

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

By "photoreceptor cells" refers to the bulk of neurons in the retina. The photoreceptor cells capture light energy units (photons) and register the events as electrical signals of the central nervous system. The signals are then relayed to intermediary layers of neurons in the retina that process and organize the information before it is transmitted along the optic nerve fibers to the brain.

By "PPARα" refers to peroxisome proliferator-activated receptor alpha, a nuclear protein encoded by the PPARA gene. PPARα is a transcription factor and a regulator of lipid metabolism in the liver. PPARα is primarily activated through ligand binding, comprising, for example, fibrate drugs used to treat hyperlipidemia, and a diverse set of insecticides, herbicides, plasticizers, and organic solvents, which are collectively termed peroxisome proliferators.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control, e.g., a standard or control condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reduces" is meant a negative alteration of at least 10%, 25%, 50%, 75%, or 100%.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

As used herein, the term "shRNA" (small hairpin RNA) refers to an RNA duplex wherein a portion of the siRNA is part of a hairpin structure (shRNA). In addition to the duplex portion, the hairpin structure may contain a loop portion positioned between the two sequences that form the duplex. The loop can vary in length. In some embodiments, the loop is 5, 6, 7, 8, 9, 10, 11, 12 or 13 nucleotides in length. The hairpin structure can also contain 3' or 5' overhang portions. In some aspects, the overhang is a 3' or a 5' overhang 0, 1, 2, 3, 4 or 5 nucleotides in length. In certain aspects, a nucleotide sequence in a vector serves as a template for the expression of a small hairpin RNA, comprising a sense region, a loop region and an antisense region. Following expression, the sense and antisense regions form a duplex. It is this duplex, forming the shRNA, which hybridizes to, for example, the Ffar1 mRNA and reduces expression of FFA1, inducing neo-angiogenesis.

By "subject" is meant a mammal, including, but not limited to, a human or non-human mammal, such as a bovine, equine, canine, ovine, or feline.

A "therapeutically effective amount" is an amount sufficient to effect beneficial or desired results, including clinical results. An effective amount can be administered in one or more administrations.

As used herein, the terms "treat," treating," "treatment," and the like refer to reducing or ameliorating a disorder and/or symptoms (e.g., AMD, MacTel or other angiogenesis-associated disease or disorder of the eye, or of tumors in general) associated therewith. It will be appreciated that, although not precluded, treating a disorder or condition does not require that the disorder, condition or symptoms associated therewith be completely eliminated.

The terms "tumor," "solid tumor," "primary tumor," and "secondary tumor" refer to carcinomas, sarcomas, adenomas, and cancers of neuronal origin and, in fact, to any type of cancer which does not originate from the hematopoietic cells and in particular concerns: carcinoma, sarcoma, adenoma, hepatocellular carcinoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphangiosarcoma, synovioma, Ewing's tumor, leiomyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, retinoblastoma, multiple myeloma, rectal carcinoma, thyroid cancer, head and neck cancer, brain cancer, cancer of the peripheral nervous system, cancer of the central nervous system, neuroblastoma, cancer of the endometrium, as well as metastasis of all the above.

Any compositions or methods provided herein can be combined with one or more of any of the other compositions and methods provided herein.

Other features and advantages of the invention will be apparent to those skilled in the art from the following detailed description and claims.

Ffar1$^{+/+}$ mice (P16; n=10 retinas; P=0.0153). Two-tailed Student t-test (FIGS. 3E, 3F, and 3I) and one-way ANOVA with Dunnett's (FIGS. 3B, 3C, 3G, and 3H) or Tukey's (FIG. 3D) post-hoc comparison; *P≤0.05, P<0.01, *P<0.001. Results are presented as mean±SEM.

Figure 4A:
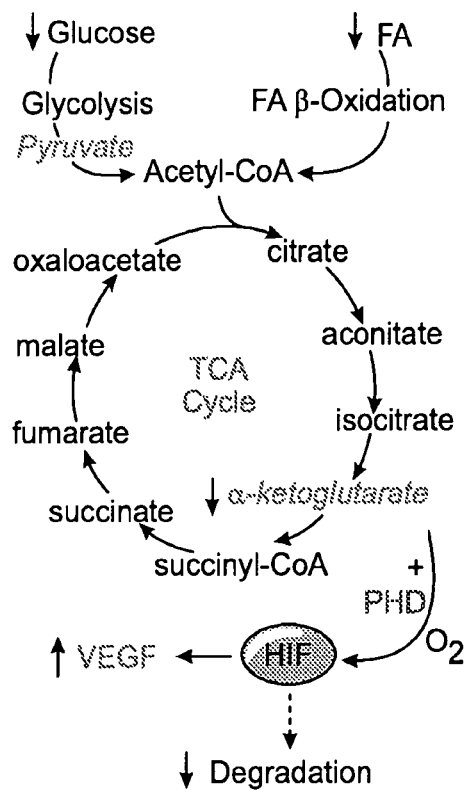

FIG. 4A depicts a schematic showing that fuel deficient Vldlr$^{-/-}$ retina generated less α-Ketoglutarate and more Vegf Dual shortage of glucose and FA uptake reduced acetyl-coA in Vldlr$^{-/-}$ retina (LC/MS/MS; n=WT: 11, Vldlr$^{-/-}$: 15 animal retinas).

Figure 4B:
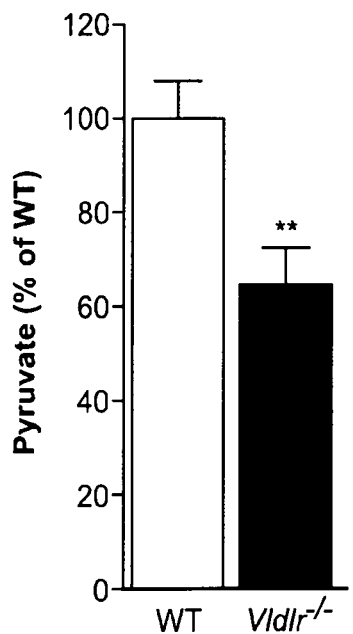

FIG. 4B depicts a bar graph showing dual shortage of pyruvate and FA uptake reduced acetyl-coA in Vldlr$^{-/-}$ retina (LC/MS/MS; n=WT: 15, Vldlr$^{-/-}$: 12 animal retinas; P=0.0032).

Figure 4C:
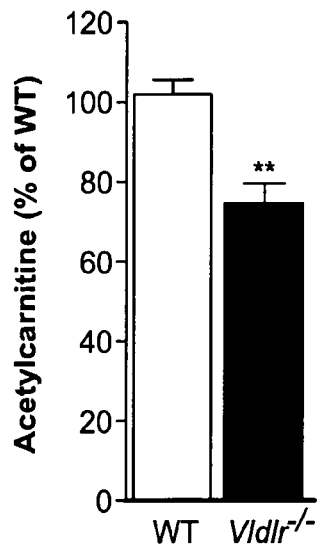

FIG. 4C depicts a bar graph showing dual shortage of glucose and FA uptake reduced acetyl-coA in Vldlr$^{-/-}$ retina (LC/MS/MS; n=WT: 11, Vldlr$^{-/-}$: 15 animal retinas; P=0.0069); estimated by measuring acetylcarnitine.

Figure 4D:
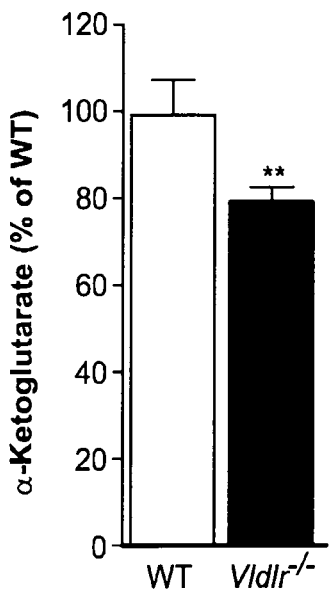

FIG. 4D depicts a bar graph showing TCA (Krebs) cycle intermediate α-KG in Vldlr$^{-/-}$ retina (LC/MS/MS; n=WT: 11, Vldlr$^{-/-}$: 15 animal retinas; P=0.0016). Together with oxygen (O$_2$), α-KG is an essential co-activator of propyl-hydroxylase dehydrogenase (PHD) that tags HIF1α for degradation by proline hydroxylation (hydroxyproline).

Figure 4E:
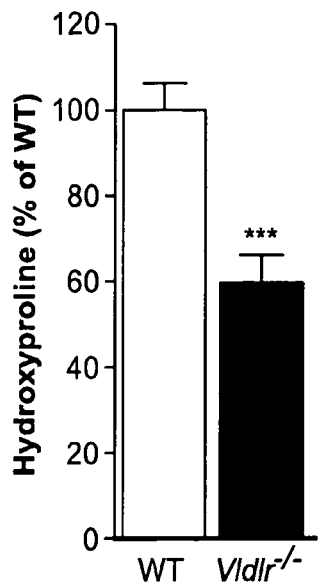

FIG. 4E depicts a bar graph showing levels of hydroxyproline residues in WT and Vldlr$^{-/-}$ retinas were measured by LC/MS/MS; n=WT: 15, Vldlr$^{-/-}$: 12 animal retinas; P=0.0004).

Figure 4F:
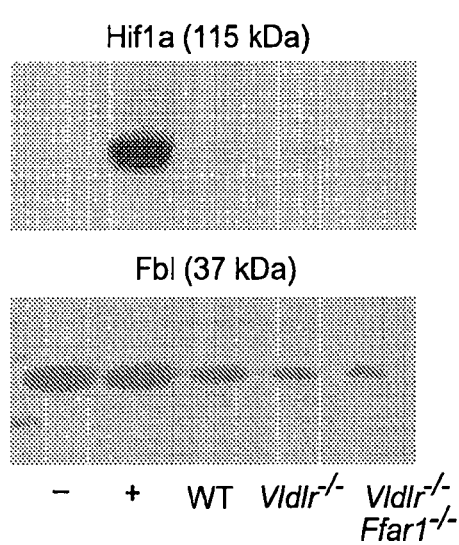
Figure 4F:
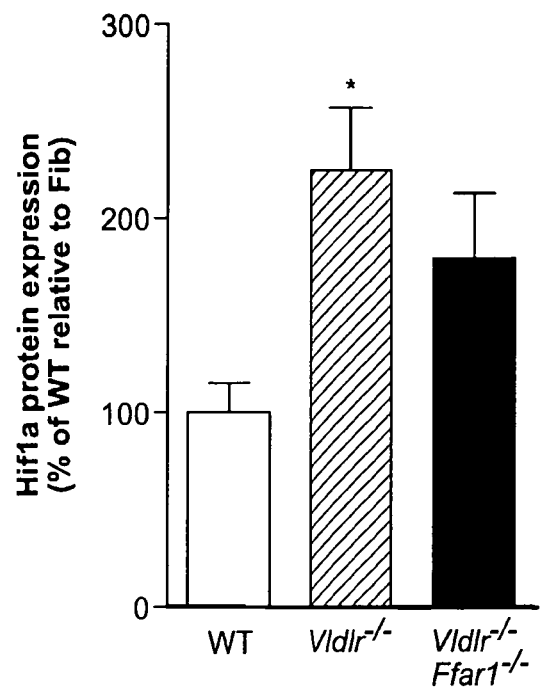

FIG. 4F depicts a blot and a bar graph showing Hif1α stabilization of WT, Vldlr and Vldlr$^{-/-}$/Ffar1$^{-/-}$ retinal nuclear extractions. Fibrillarin (Fbl) was used as a nuclear loading control (n=3 all groups).

Figure 4G:
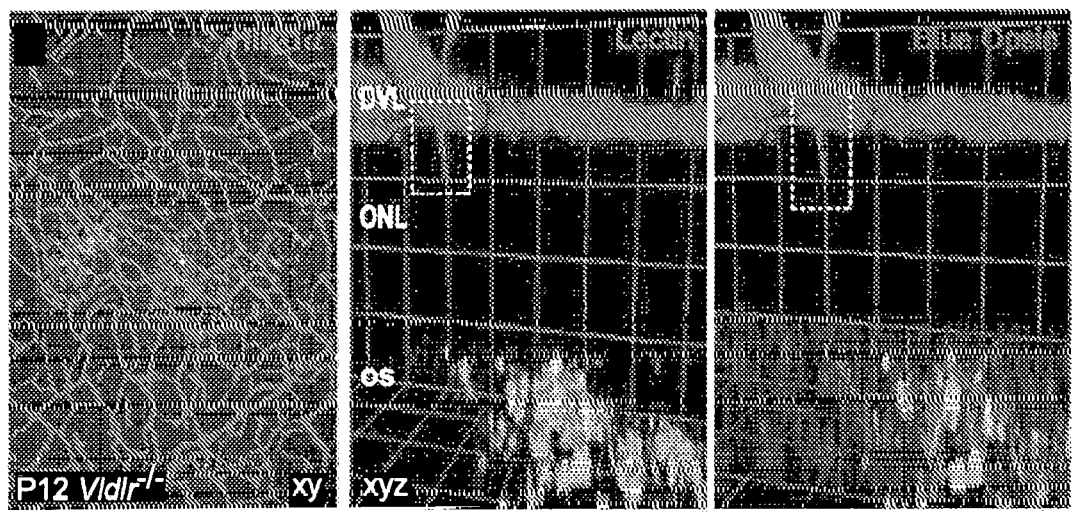

FIG. 4G depicts images showing that Hif1α retinal expression in Vldlr$^{-/-}$ photoreceptor layer (ONL; P12 retinal flat mounts) Scale: 100 μm; left: extended focus; middle and right panels: 3D confocal IHC, n=3.

Figure 4H:
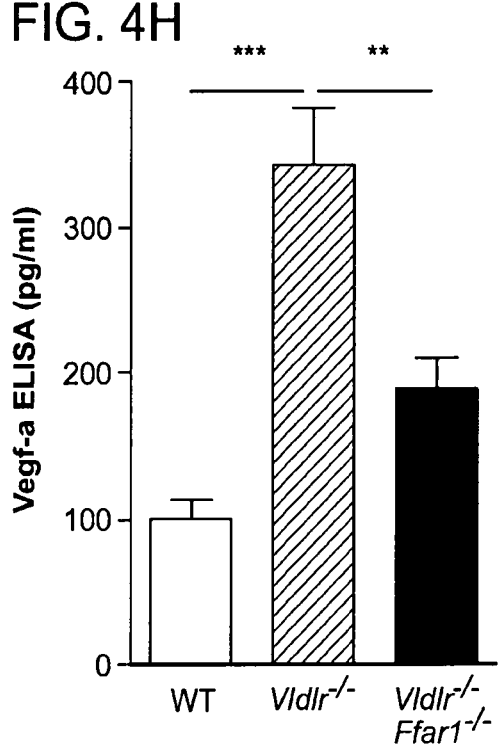

FIG. 4H depicts a bar graph showing that Vegfa was also secreted (P16, ELISA, n=6 retinas; n=3 retinas).

Figure 4I:
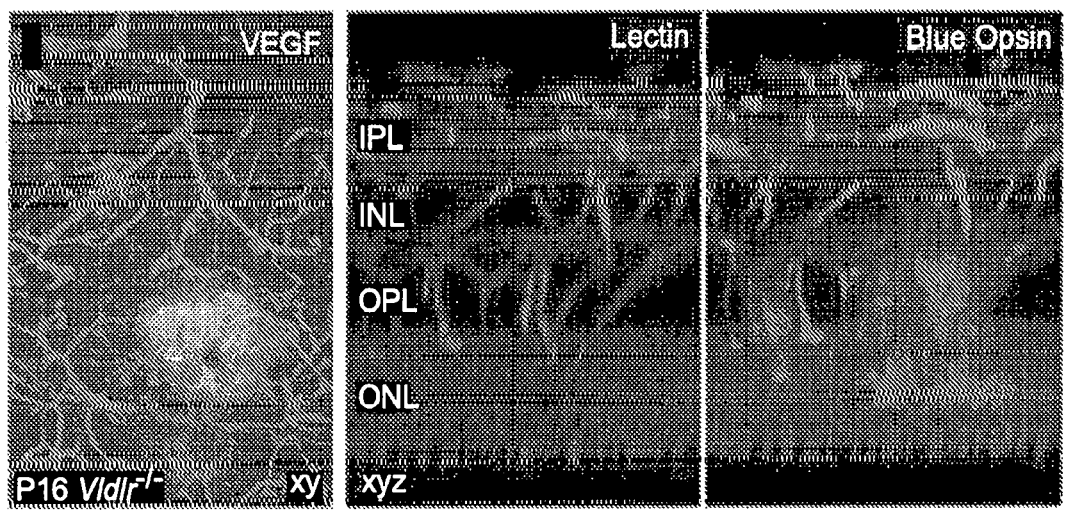

FIG. 4I depicts images showing that Vegfa was also secreted and 3D confocal IHC, n=3 retinas; scale 100 μm; left extended focus; middle and right panels 3D confocal IHC.

Figure 4J:
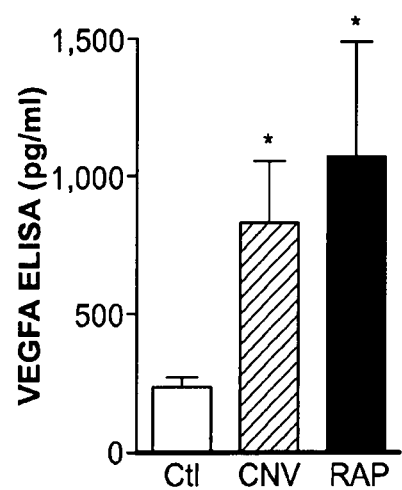

FIG. 4J depicts an a bar graph showing that human subjects with AMD, either retinal angiomatous proliferation (RAP, n=3) or choroidal neovascularization (CNV, n=7) had higher VEGFA vitreous levels by ELISA compared to control subjects without pathologic neovessels (macular hole; n=8). Two-tailed Student t-test (FIGS. 4C and 4D), Mann Whitney test (FIGS. 4B and 4E), and one-way ANOVAs with post-hocDunett's (FIGS. 4F and 4G) or Tukey's multiple comparison (FIG. 4H); *P≤0.05, P<0.01, *P<0.001. Results are presented as mean±SEM.

Figure 5A:
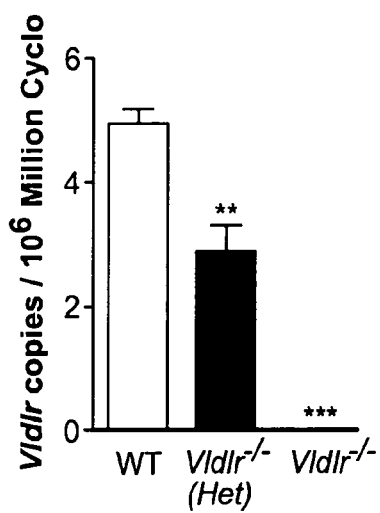

FIG. 5A depicts a bar graph showing that photoreceptor-selective Vldlr depletion generates RAP-like lesions. Retinal Vldlr expression in WT (n=4), heterozygous (het) Vldlr$^{+/-}$ (n=5) and Vldlr mice (n=5 retinas; qRT-PCR); ns: not significant.

Figure 5B:
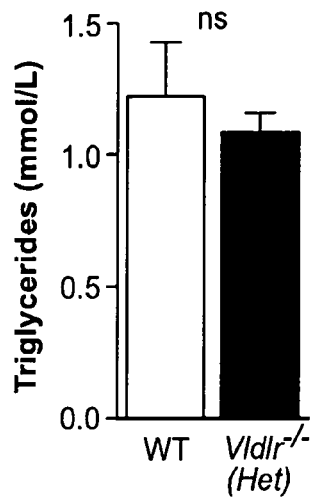

FIG. 5B depicts a bar graph showing triglycerides of Vldlr$^{+/-}$ (Het) mice used to locally knockdown Vldlr in photoreceptors. n=WT: 7 Vldlr$^{+/-}$: 8 plasmas.

Figure 5C:
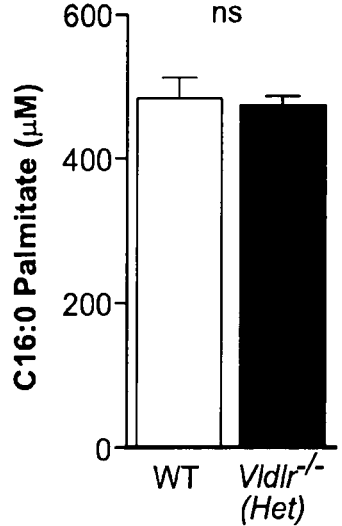

FIG. 5C depicts a bar graph showing palmitate plasma levels of Vldlr$^{+/-}$ (Het) mice used to locally knockdown Vldlr in photoreceptors. n=WT: 7 Vldlr$^{+/-}$: 8 plasmas.

Figure 5D:
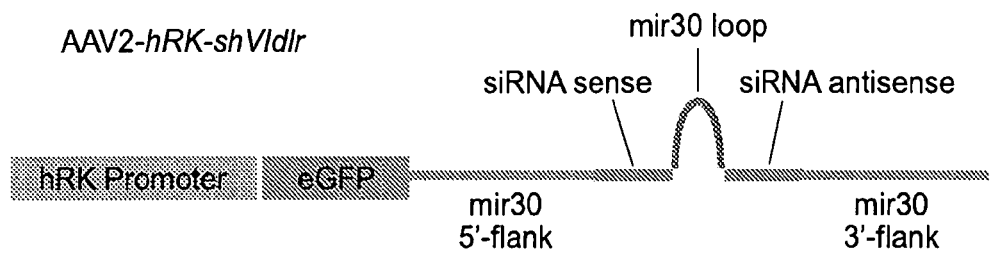

FIG. 5D depicts an image showing that AAV2 viral vector containing a photoreceptor-specific hRK promoter was cloned to include a fluorescent eGFP and different shRNA against Vldlr (Cahill, G. F. *N Engl J Med* 282, 668-675 (1970), Wong-Riley, M. T. T. *Eye Brain* 2, 99-116 (2010), and Niu, Y.-G. & Evans, R. D. *J Lipids* 2011, 189876 (2011).

Figure 5E:
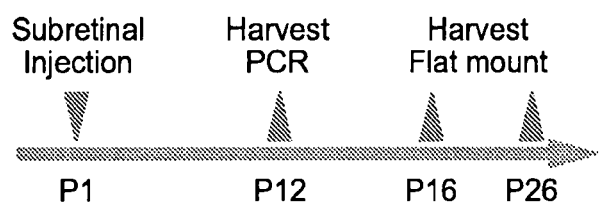

FIG. 5E depicts an image showing that timing of subretinal vector injection (P1) and retina collections (P12, 16, 26).

Figure 5F:
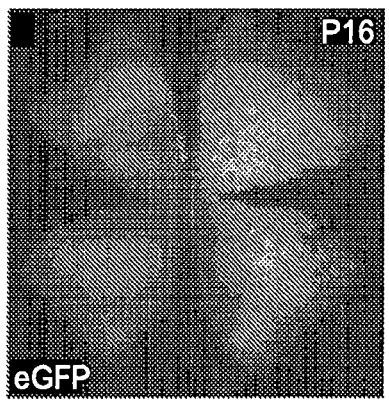

FIG. 5F depicts an image showing retinal distribution of viral vectors.

Figure 5G:
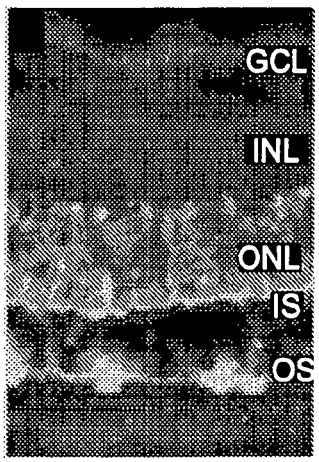

FIG. 5G depicts an image showing retinal distribution of viral vectors in photoreceptors (ONL). OS: outer segment, IS: inner segment, ONL: outer nuclear layer, INL: inner nuclear layer, GCL: ganglion cell layer; n=5 retinas.

Figure 5H:
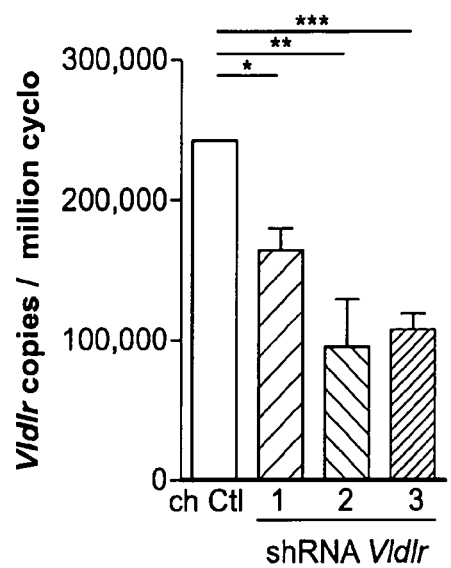

FIG. 5H depicts a bar graph showing retinal Vldlr suppression by 3 different shRNA in Vldlr$^{+/-}$ mice (qRT-PCR; n=shCtl: 8, shRNA-1: 12, shRNA-2: 4, shRNA-3: 8 retinas).

Figure 5I:
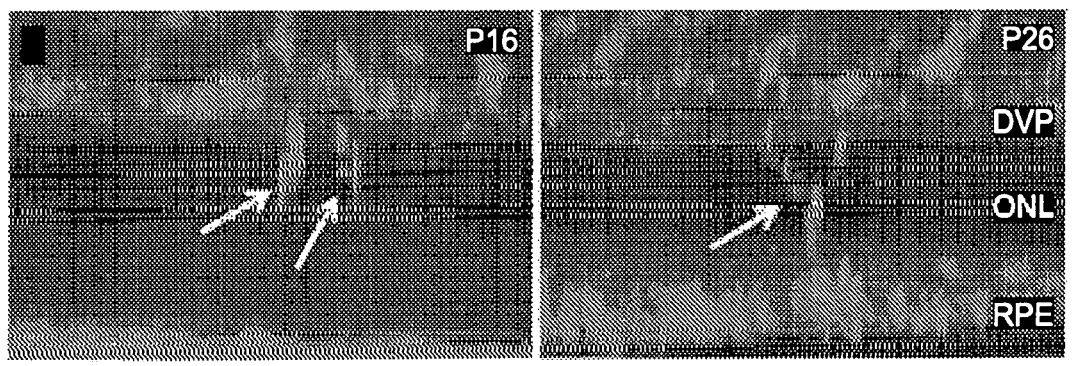

FIG. 5I depicts images showing the development of some RAP-like lesions when Vldlr was selectively depleted in Vldlr$^{+/-}$ mouse photoreceptors. DVP: deep vascular plexus, RPE: retinal pigment epithelium. n=5 retinas. Two-tailed Student t-test (FIGS. 5B and 5C) and one-way ANOVA with Dunnett's post-hoc comparison (FIGS. 5A and 5H); * P<0.05,  P<0.01, *P<0.001.

Figure 6A:
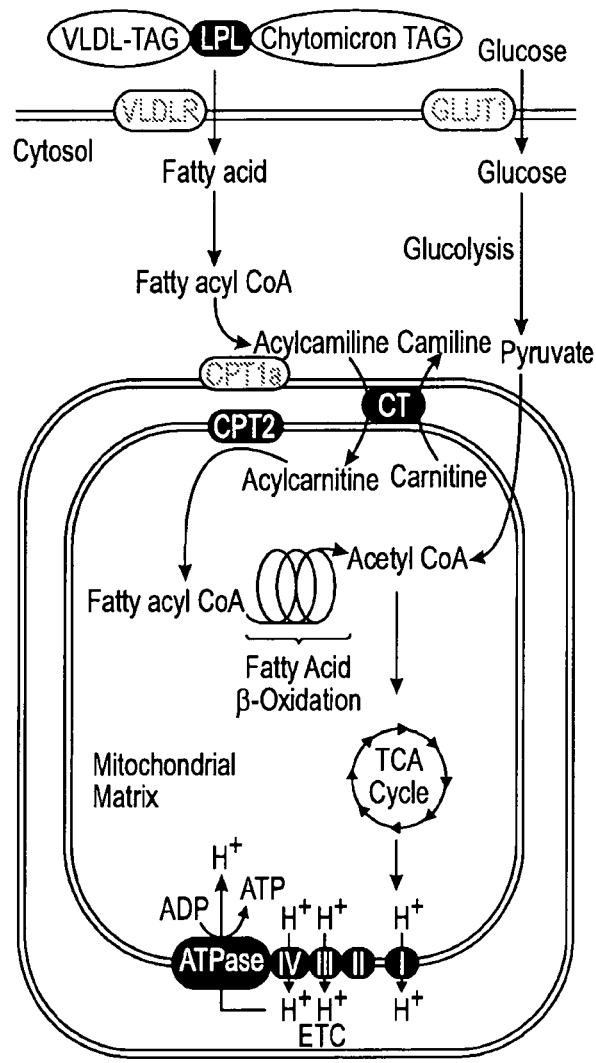

FIG. 6A depicts a schematic showing that fatty acids and glucose fuel the mouse retina. FIG. 6A depicts a schematic overview of lipid and glucose metabolism converging to produce acetyl-coA, which fuels the Krebs (or TCA) cycle and the electron transfer chain (ETC) to produce ATP; ns: not significant.

Figure 6B:
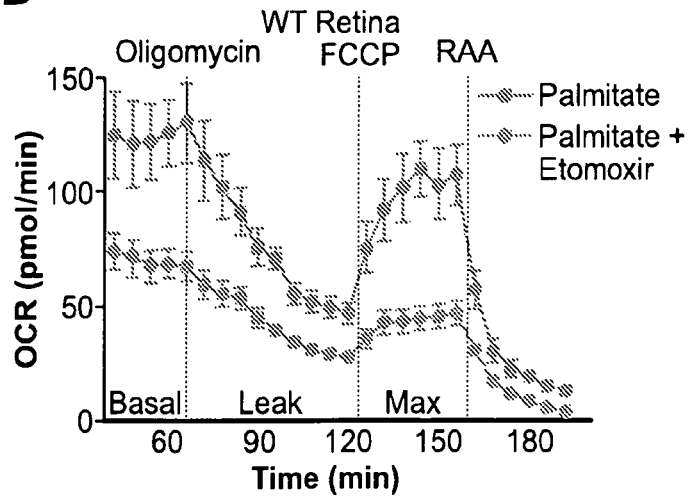

FIG. 6B depicts a graph showing oxygen consumption rates (OCR) of ex vivo retinas incubated with palmitate in the presence (n=8) or absence (n=6 retinas) of Etomoxir (40 μM).

Figure 6C:
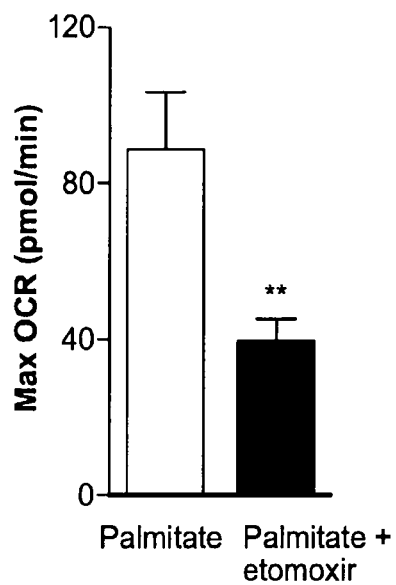

FIG. 6C depicts a bar graph showing maximal OCR of ex vivo retinas incubated with palmitate in the presence (n=8) or absence (n=6 retinas) of Etomoxir (40 μM); P=0.0027.

Figure 6D:
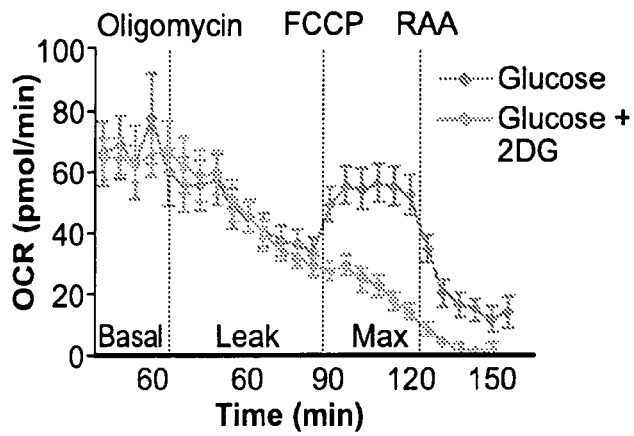

FIG. 6D depicts a graph showing OCR of ex vivo retinas incubated with glucose (12 mM) and treated or not with 2-deoxyglucose (2-DG; 100 mM) to inhibit glycolysis and glucose oxidation; n=8 retinas.

Figure 6E:
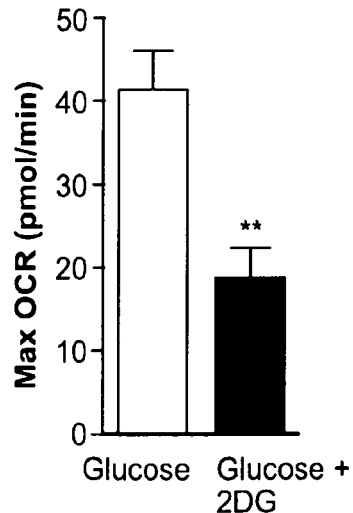

FIG. 6E depicts a bar graph showing maximal OCR of ex vivo retinas incubated with glucose (12 mM) and treated or not with 2-deoxyglucose (2-DG; 100 mM) to inhibit glycolysis and glucose oxidation. n=8 retinas; P=0.0019.

Figure 6F:
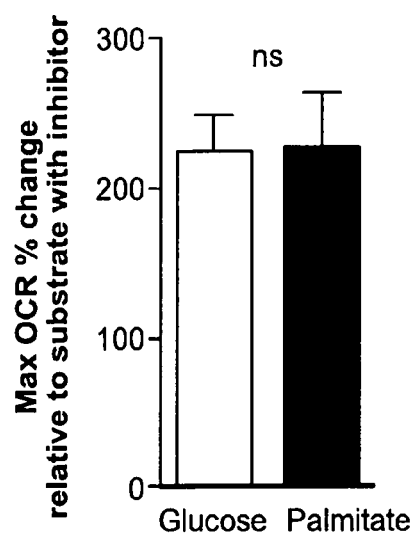

FIG. 6F depicts a bar graph showing maximal oxidation capacity for glucose (n=8) or palmitate (n=6 retinas) relative to their respective inhibitor.

Figure 6G:
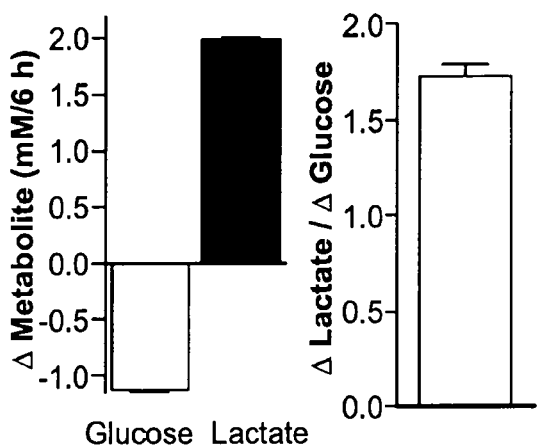

FIG. 6G depicts a bar graph showing glucose uptake and lactate secreted by ex vivo retinas incubated in glucose-containing media (12 mM, 6 hours); glycolysis accounted for the majority of 16 glucose utilization, producing 2 lactates per glucose molecule; n=4 retinas.

Figure 6H:
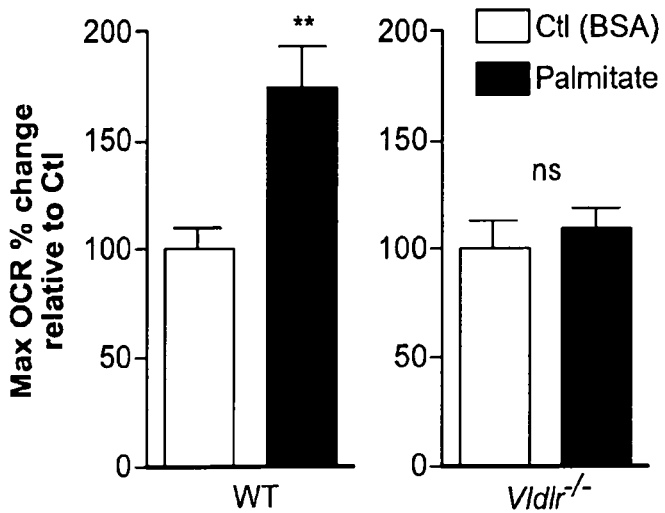

FIG. 6H depicts a bar graph showing that palmitate increased maximal OCR in wild type (WT; n=Ctl: 15, Palmitate: 14 retinas) but not in Vldlr$^{-/-}$ retinas (n=Ctl: 10, Palmitate: 13 retinas; P=0.0035); two-tailed Mann Whitney (FIGS. 6B, 6C, and 6F) or Student t-test (FIGS. 6D, 6E, and 6H); ** P<0.01.

Figure 7A:
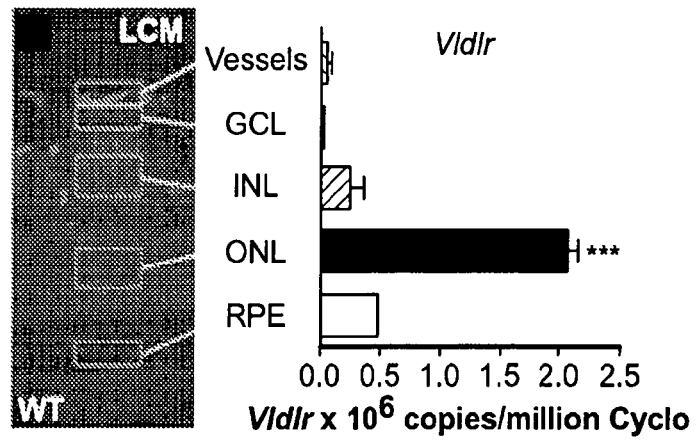

FIG. 7A depicts an image and a bar graph showing deficient lipid uptake in Vldlr$^{-/-}$ mice. Vldlr is highly expressed in photoreceptors (outer nuclear layer; ONL) by laser capture microdissection (LCM and qRT-PCR). GCL: ganglion cell layer, INL: inner nuclear layer, RPE: retinal pigment epithelium. n=3 retinas.

Figure 7B:
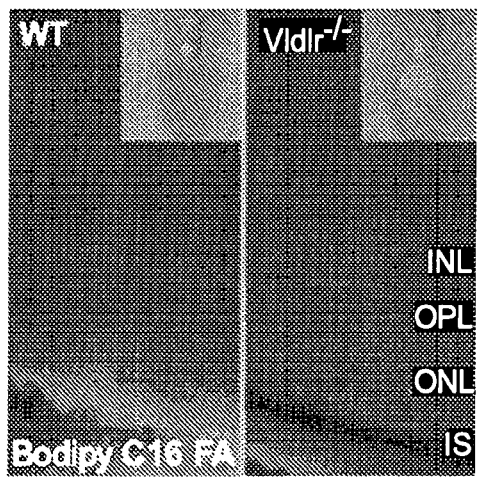

FIG. 7B depicts an image showing increased fluorochrome-labeled long-chain FA (Bodipy C-16) in photoreceptor inner segments (IS) of WT mice, compared to Vldlr$^{-/-}$ mice gavaged with these lipids. Also of note was visibly turbid serum in Vldlr$^{-/-}$ mice from increased serum lipid associated with decreased lipid uptake (corner); n=3 retinas.

Figure 7C:
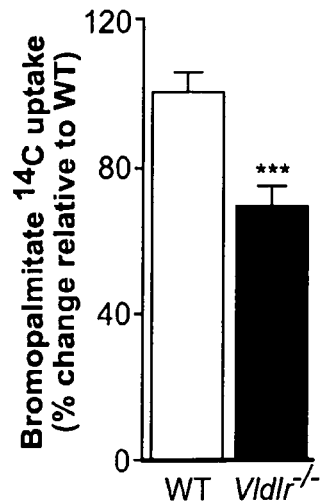

FIG. 7C depicts a bar graph showing reduced bromopalmitate-$^{14}$C retinal uptake in Vldlr$^{-/-}$ (n=12) compared to WT retinas (n=16).

Figure 7D:
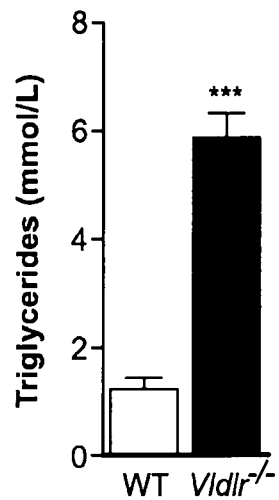

FIG. 7D depicts a bar graph showing reduced bromopalmitate-$^{14}$C retinal uptake in Vldlr$^{-/-}$ (n=12) compared to WT retinas (n=16), associated with increased triglycerides.

Figure 7E:
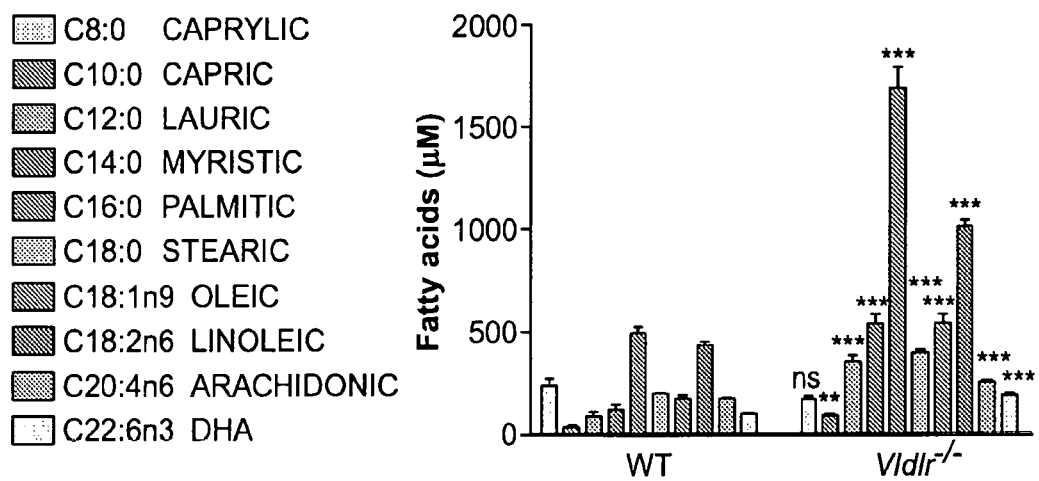

FIG. 7E depicts an image and a bar graph showing reduced bromopalmitate-$^{14}$C retinal uptake in Vldlr$^{-/-}$ (n=12) compared to WT retinas (n=16), FA plasma levels (red: palmitate, C16); n=WT: 7, Vldlr$^{-/-}$; 13 plasma samples; two-tailed Mann Withney (FIG. 7E) or Student t-test (FIGS. 7C-7E) and one-way ANOVA with Tukey's post-hoc comparison (FIG. 7A); * P<0.05, P<0.01, * P<0.001.

Figure 8A:
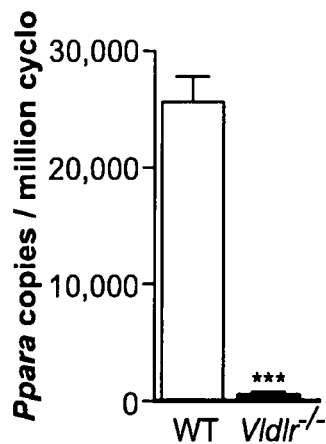

FIG. 8A depicts a bar graph showing the role of PPARα (peroxisome proliferator-activated receptor a) in Vldlr$^{-/-}$ mice. PPARα, which regulates FA β-oxidation, was suppressed in Vldlr$^{-/-}$ retina (n=3, P=0.0079).

Figure 8B:
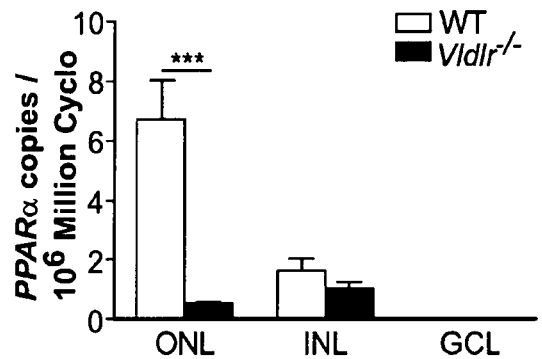

FIG. 8B depicts a bar graph showing that PPARα, which regulates FA β-oxidation, was suppressed in Vldlr$^{-/-}$ retina mostly in photoreceptors (ONL, n=3 animals).

Figure 8C:
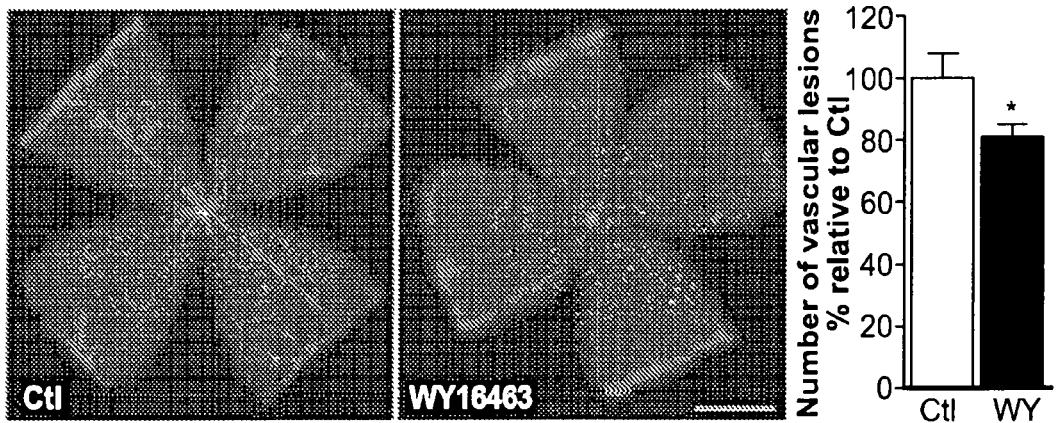

FIG. 8C depicts images and a bar graph showing PPARα agonist WY16463 reduced the number of vascular lesions. Ctl: n=10, WY: n=12 retinas; P=0.0429. Two-tailed Student t-test (FIGS. 8A and 8C) and one-way ANOVA with Tukey's posthoc comparison (FIG. 8B); *P<0.05, ***P<0.001.

Figure 9A:
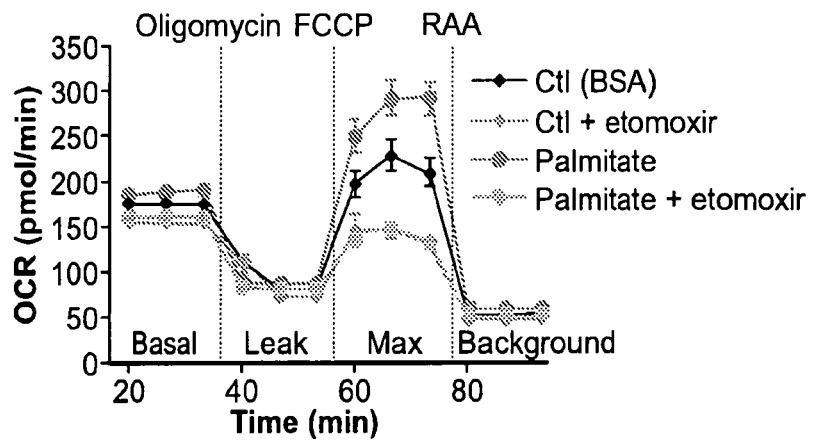

FIG. 9A depicts a graph showing FA oxidation of exogenous and endogenous lipids by photoreceptors. In vitro oxygen consumption rates (OCR) of photoreceptors (661W) incubated with palmitate conjugated to BSA or BSA alone (control) in the presence or absence of Etomoxir (40 μM); n=5-6 retinas.

Figure 9B:
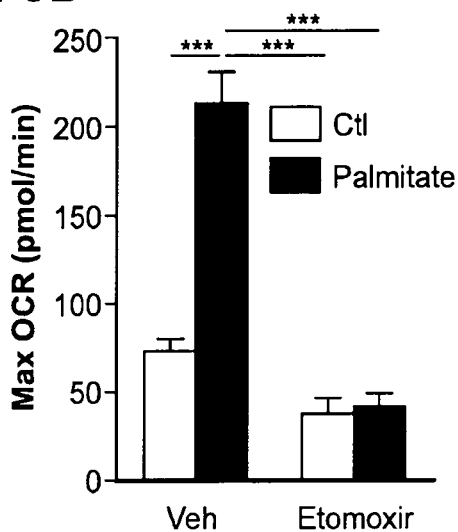

FIG. 9B depicts a bar graph showing maximal oxidative capacity of photoreceptors (661W) incubated with palmitate conjugated to BSA or BSA alone (control) in the presence or absence of Etomoxir (40 μM); n=5-6 retinas.

Figure 9C:
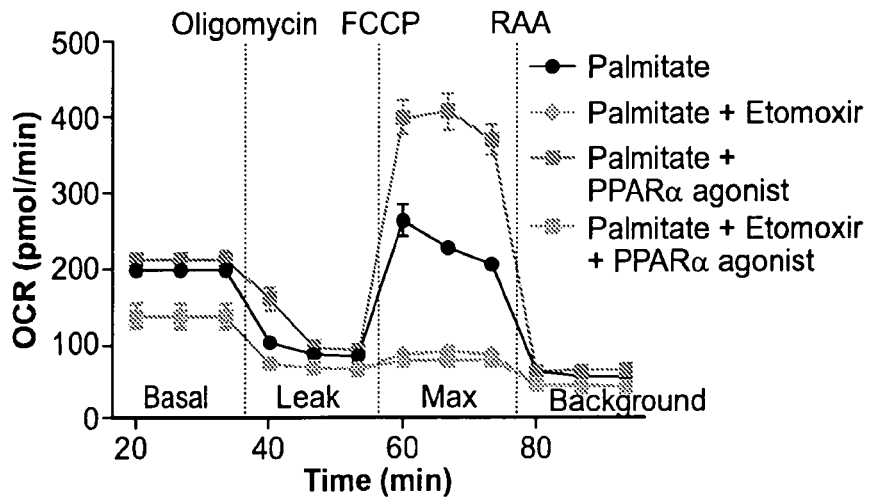

FIG. 9C depicts a graph showing OCR of photoreceptors (661W) in the presence or absence of palmitate and treated or not with PPARα agonist (GW9578, 100 nM, 48 hours); n=4-6 retinas.

Figure 9D:
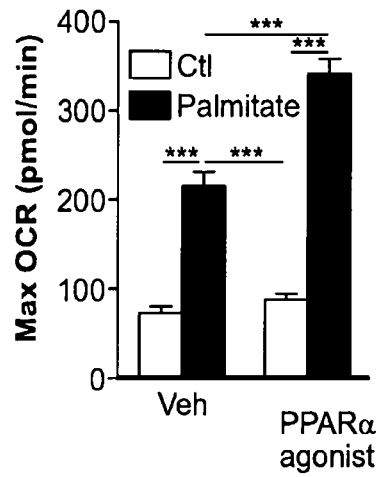

FIG. 9D depicts a bar graph showing maximal oxidation capacity of photoreceptors (661W) in the presence or absence of palmitate and treated or not with PPARα agonist (GW9578, 100 nM, 48 hours); n=4-6 retinas.

Figure 9E:
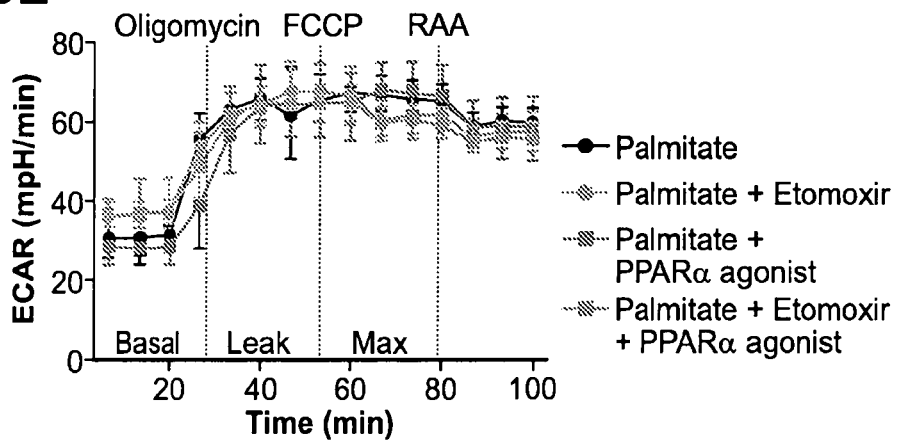

FIG. 9E depicts a graph showing extra cellular acidification rate (ECAR) of photoreceptors (661W) in the presence or absence of palmitate and treated or not with PPARα agonist (GW9578, 100 nM, 48 hours); n=4-6 retinas.

Figure 9F:
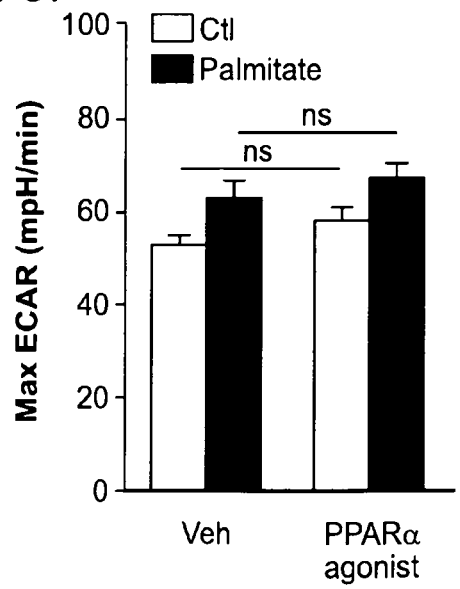

FIG. 9F depicts a bar graph showing extra cellular acidification rate (ECAR) of photoreceptors (661W) in the presence or absence of palmitate and treated or not with PPARα agonist (GW9578, 100 nM, 48 hours); n=4-6 retinas. PPARα agonist induced FA β-oxidation without significantly affecting glycolysis, as suggested by comparable acidification rates. One-way ANOVA with Tukey's post-hoc comparison (FIGS. 9A-9D) and Kruskal-Wallis with Dunn's Multiple comparison (FIGS. 9E and 9F); ns: not significant, *** P<0.001.

FIG. 10A depicts an image showing that glucose metabolism was suppressed in Vldlr$^{-/-}$ retina. Carbohydrate metabolism was the molecular pathway most regulated on a gene array comparing WT and Vldlr$^{-/-}$ retinas. Ingenuity Pathway analysis, n=3 animals (littermates).

FIG. 10B depicts a bar graph showing pyruvate kinase (Pkm2), associated with the final unidirectional step of glycolysis, was highly regulated on the gene array. Pkm2 suppression was confirmed in Vldlr$^{-/-}$ retina by qRT-PCR. n=WT: 6, Vldlr$^{-/-}$: 5 retinas; P=0.0215.

FIG. 10C depicts a bar graph and a blot showing that Glut3 and 4 protein expression was not significantly different between WT (n=4) and Vldlr$^{-/-}$ (n=3) retinas; two-tailed Student t-test; *P<0.05.

Figure 11A:
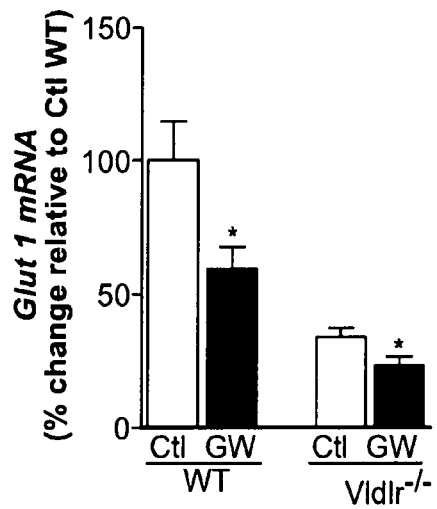

FIG. 11A depicts a bar graph showing that Glut1 is regulated by FFA1. FFA1 agonist GW9508 (GW) reduces Glut1 expression in WT P=0.0142 and Vldlr$^{-/-}$ P=0.0284; retina; n=11-16 retinas.

Figure 11B:
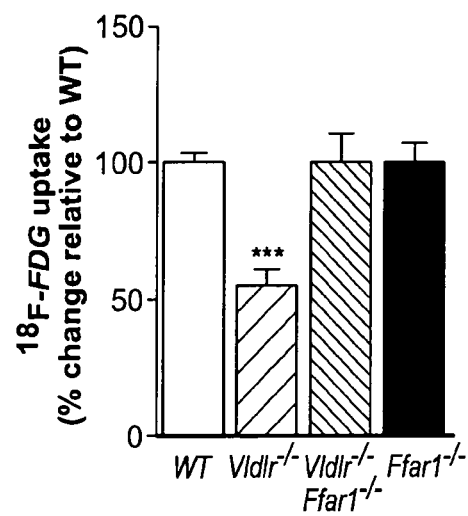

FIG. 11B depicts a bar graph showing that Glucose uptake ($^{18}$F-FDG); Ffar1 deletion in Vldlr$^{-/-}$ mice reestablished retinal glucose uptake and Glut1 expression n=b: 6-17, c: 3-9 retinas.

Figure 11C:
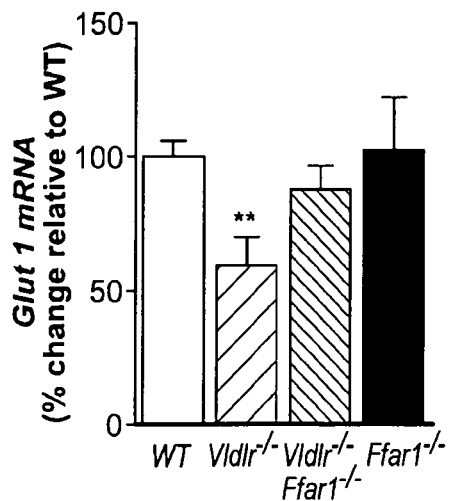

FIG. 11C depicts a bar graph showing Glut1 mRNA expression in WT, Vldlr$^{-/-}$, Vldlr$^{-/-}$/Ffar1$^{-/-}$, and Ffar1$^{-/-}$ retinas. Ffar1 deletion in Vldlr$^{-/-}$ mice reestablished retinal glucose uptake and Glut1 expression n=b: 6-17, c: 3-9 retinas.

Figure 11D:
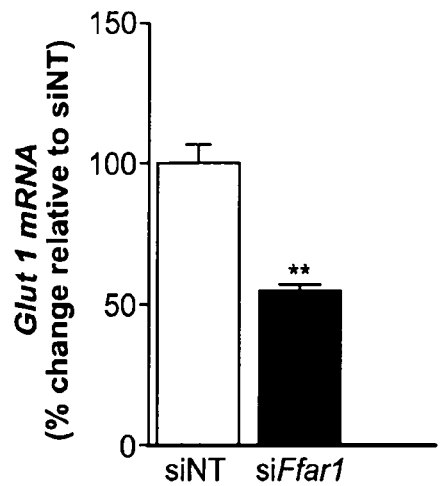

FIG. 11D depicts a bar graph showing knock-down (in vitro) of Ffar1 (using siRNA; P=0.0025).

Figure 11E:
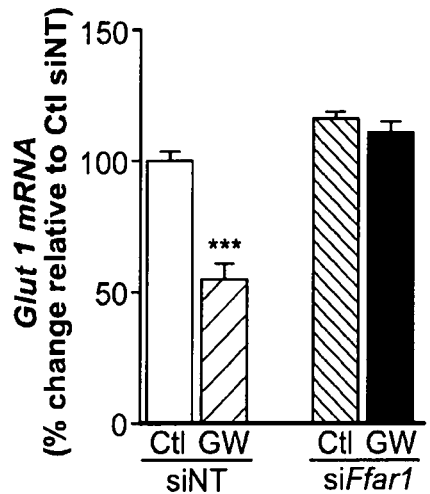

FIG. 11E depicts a bar graph showing that knock-down of Ffar1 using siRNA prevented Glut1 suppression by GW9508 in photoreceptor cells (661W); n=3 experiments.

Figure 11F:
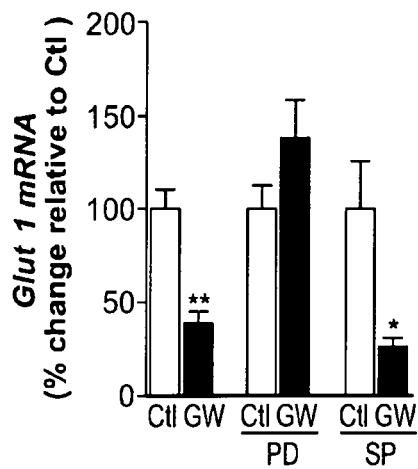

FIG. 11F depicts a bar graph showing that inhibition of MEK/ERK signaling (PD: PD98059, 20 μM; P=0.0056) prevented FFA1-mediated Glut1 suppression in 661W photoreceptors, but not JNK signaling (SP: SP600125, 5004, P=0.0121); n=3-7. Two-tailed Student t-test (FIGS. 11A, 11D, and 11F) or Mann Whitney (FIG. 11F) and one-way ANOVA with Dunnett's (FIGS. 11B and 11C) or Bonferroni's post-hoc comparison (FIG. 11E);* P≤0.05,  P<0.01, * P<0.001. Results are presented as mean±SEM.

Figure 12A:
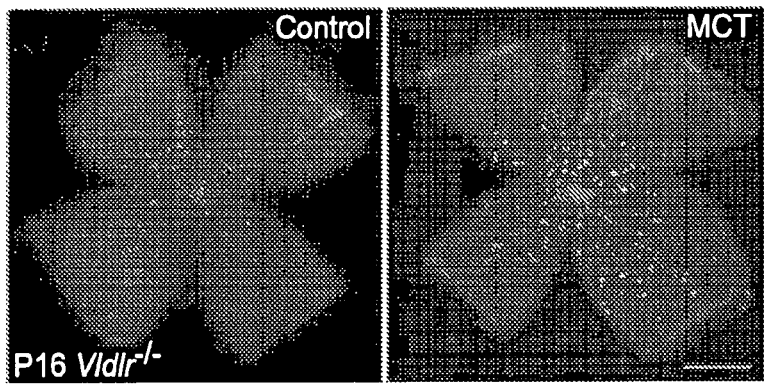

FIG. 12A depicts an image showing that FFA1 agonists increased retinal angiomatous proliferation. FFA1 is activated by fatty acids with C>6 (Briscoe et al. J. Biol. Chem 278: 11303-11311). Mice fed MCT (middle chain triglycerides; n=10 retinas) with C8-10 more than doubled the number of vascular lesions compared to control (normal saline; n=15 retinas; P=0.0011).

Figure 12B:
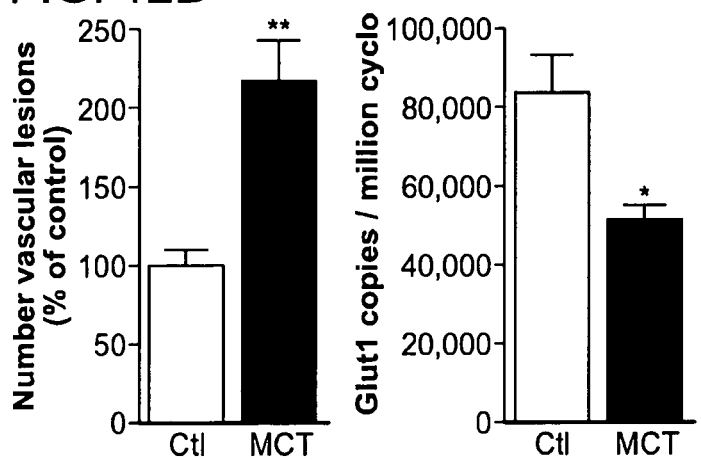

FIG. 12B depicts bar graphs showing that mice fed MCT suppressed Glut1 expression in Vldlr$^{-/-}$ retinas; n=6 retinas; P=0.0231.

Figure 12C:
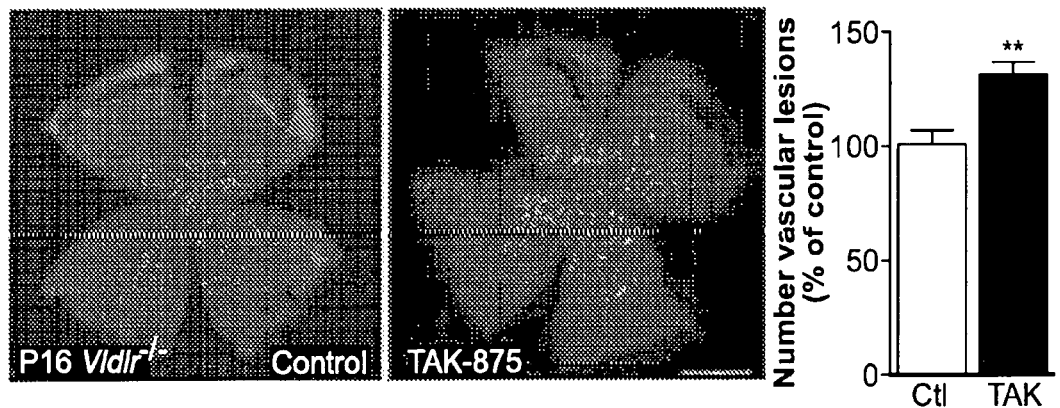

FIG. 12C depicts an image and a bar graph showing that selective FFA1 agonist TAK-875 significantly increased the number of RAP-like lesions; Ctl: n=9, TAK: n=8 retinas; P=0.0035; scale: 1 mm. Results are presented as mean±SEM. Two-tailed Student t-test; * P<0.05, ** P<0.01.

Figure 13A:
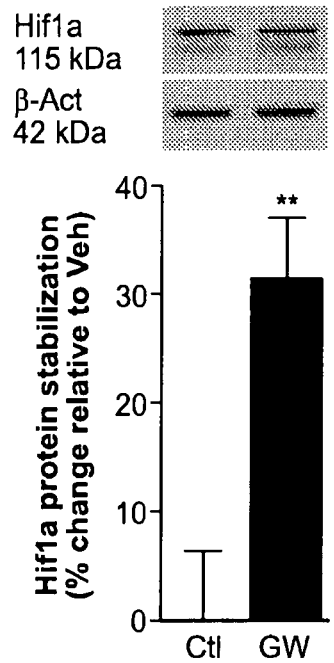

FIG. 13A depicts a blot and a bar graph showing that FFA1 stabilizes Hifα and promotes Vegfa secretion in photoreceptors. In vivo, FFA1 agonist GW9508 (GW) stabilized Hifα in WT retinas; n=6 experiments; P=0.0044.

Figure 13B:
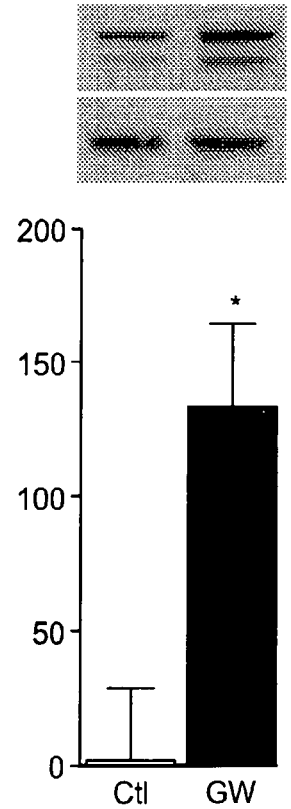

FIG. 13B depicts a blot and a bar graph showing that FFA1 agonist GW9508 (GW) stabilized Hifα in Vldlr$^{-/-}$ retinas; n=6 experiments; P=0.0411.

Figure 13C:
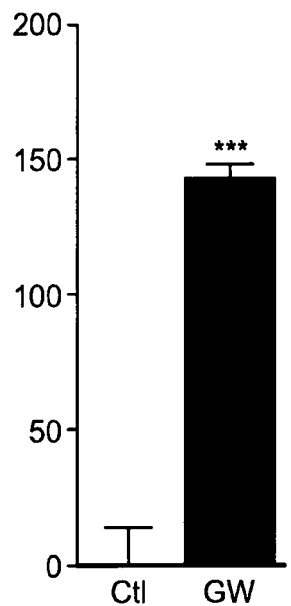

FIG. 13C depicts a blot and a bar graph showing that decreased glucose uptake in GW9508-treated or glucosestarved photoreceptors (661W), was associated with stabilized Hifα; n=3 experiments; P=0.0006.

Figure 13D:
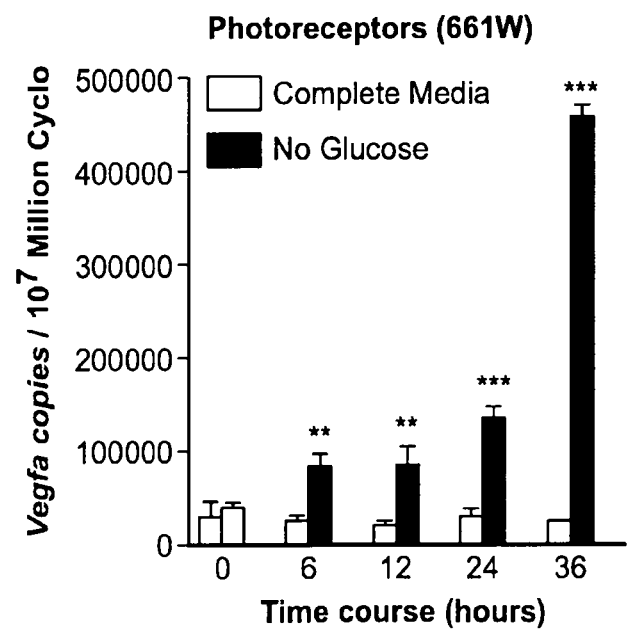

FIG. 13D depicts a bar graph showing that decreased glucose uptake in GW9508-treated or glucosestarved photoreceptors (661W), was associated with increased Vegfa expression; n=3 experiments.

Figure 13E:
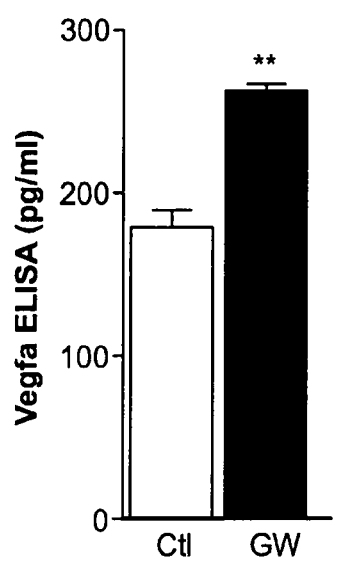

FIG. 13E depicts a bar graph showing that decreased glucose uptake in GW9508-treated or glucosestarved photoreceptors (661W), was associated with secretion (ELISA); n=3 experiments; P=0.0013. Two-tailed Student t-test (FIGS. 13A, 13C and 13E) or Mann Whitney test (FIG. 13B) and Two-way ANOVA with Bonferonni post-hoc comparison (FIG. 13D);
*P<0.05, P<0.01, *P<0.001. Results are presented as mean±SEM.

Figure 14A:
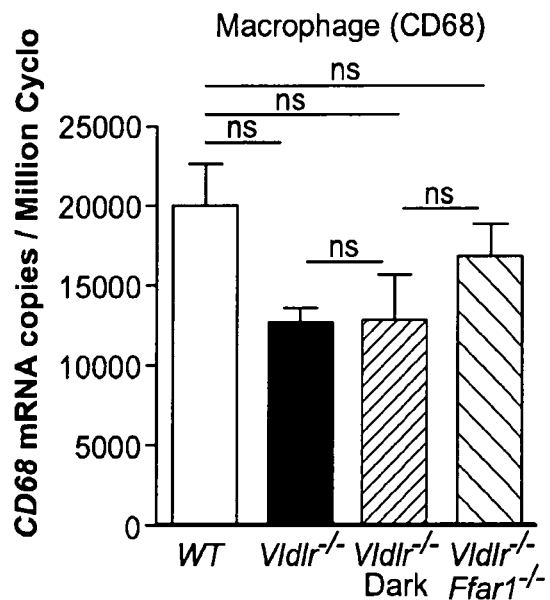

FIG. 14A depicts a bar graph showing that macrophages surround mature (but not early immature) RAP-like lesions. Markers of macrophages (CD68) were not increased in the initial phase of Vldlr$^{-/-}$ RAP-like lesion development (P12), even in pups raised in darkness that have more vascular lesions; n=7-13 retinas.

Figure 14B:
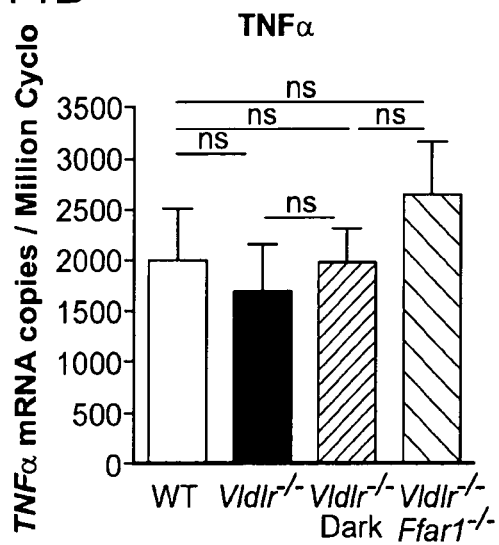

FIG. 14B depicts a bar graph showing that inflammatory cytokines (TNFα) were not increased in the initial phase of Vldlr$^{-/-}$ RAP-like lesion development (P12), even in pups raised in darkness that have more vascular lesions; n=7-13 retinas.

Figure 14C:
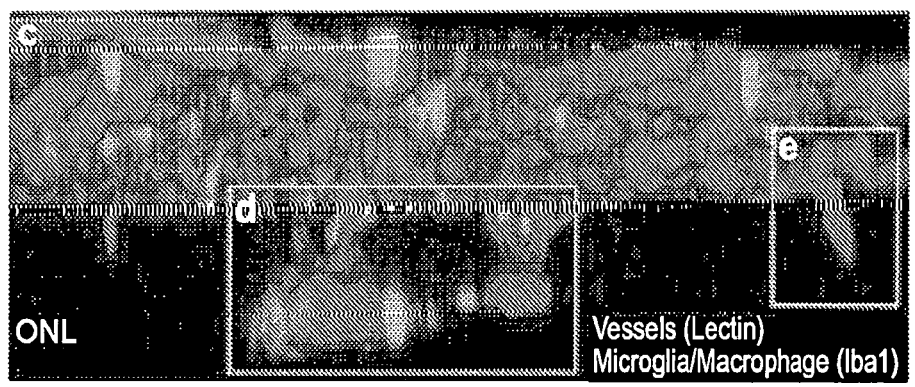

FIG. 14C depicts an image showing macrophages/microglial cells (Iba1, green).

Figure 14D:
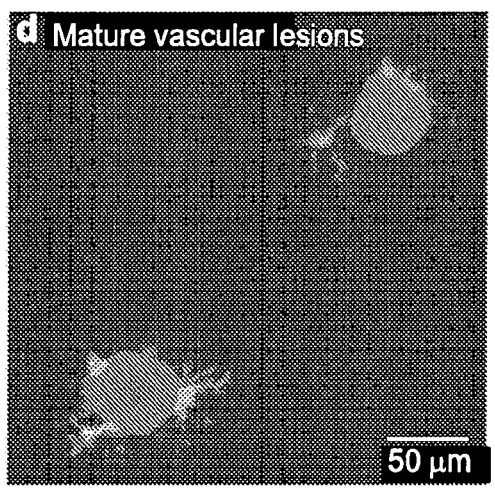

FIG. 14D depicts an image showing that macrophages/microglial cells surround mature vascular legions as confirmed by confocal cross-sections of these lesions; n=5 retinas.

Figure 14E:
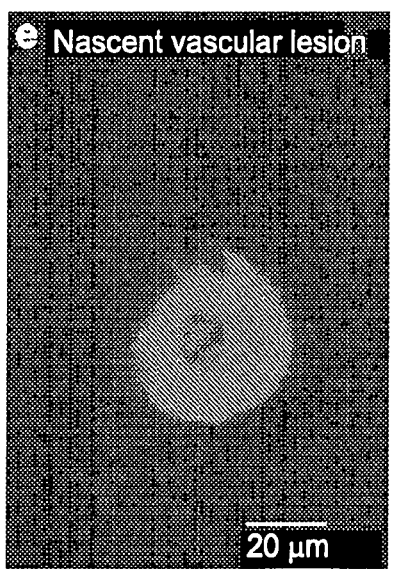

FIG. 14E depicts an image showing that macrophages/microglial cells did not surround nascent RAP-like vessels close to the deep vascular plexus (DVP), as confirmed by confocal cross-sections of these lesions. n=5 retinas. ONL: outer nuclear layer. Scale bar: FIG. 14E, 20 μm. Kruskal-Wallis with Dunn's multiple comparison; *P<0.05, **P<0.01.

DETAILED DESCRIPTION OF THE INVENTION

The invention is based, at least in part, upon the discovery that the retina uses fatty acid (FA) β-oxidation for energy, and, in particular, that a lipid sensor, FFA1, curbs glucose uptake when FAs are available. Discovery of such a role for FFA1, at least in part, indicates that a neural cell (e.g., retinal cell) disease or disorder that is characterized by angiogenesis can be effectively treated or prevented in a subject and/or model system via administration of a therapeutically effective/prophylactically effective amount of a FFA1 inhibitor to the subject and/or model system. Optionally, treatment of vascular diseases of the eye such as age-related macular degeneration (AMD) and retinopathy of prematurity (ROP), as well as treatment of retinal degeneration and/or tumors in general is also contemplated for inhibitors of the invention. In related aspects, not only FFA1 (GPR40), but also, e.g., GPR84 and/or GPR 120 can be targeted, to similar therapeutic effect. Use of known FFA1 inhibitors, including small molecule compounds and inhibitory nucleic acids is expressly contemplated. Methods for identifying new FFA1 inhibitors via, e.g., in vitro monitoring of glucose uptake of retinal cells (optionally comprising Vldlr deletion) contacted with, e.g., a compound library, is also contemplated.

Additional aspects and embodiments of the invention are described below.

Mechanism of Action

Without wishing to be bound by theory, the instant invention is believed to function in the following manner. Tissues with high metabolic rates often use lipid as well as glucose for energy, conferring a survival advantage during feast and famine (Cahill, G. F. *N Engl J Med* 282, 668-675 (1970)). Current dogma suggests that high-energy consuming photoreceptors depend on glucose (Wong-Riley, M. T. T. *Eye Brain* 2, 99-116 (2010)). Very low-density lipoprotein receptor (VLDLR), expressed in tissues with a high metabolic rate, facilitates the uptake of triglyceride-derived FA (Niu, Y.-G. & Evans, R. D. *J Lipids* 2011, 189876 (2011)). Vldlr is present in photoreceptors (Dorrell, M. I., et al. *J Clin Invest* 119, 611-623 (2009)). In Vldlr$^{-/-}$ retinas, FFA1, sensing high circulating lipid levels despite decreased FA uptake (Goudriaan, J. R., et al. *Journal of lipid research* 45, 1475-1481 (2004)), suppresses glucose transporter Glut1. This impaired glucose entry into photoreceptors results in a dual lipid/glucose fuel shortage and reduction in the Krebs cycle intermediate α-ketoglutarate (KG). Low α-KG levels promote hypoxia-induced factor-1α (Hif1α) stabilization and vascular endothelial growth factor (Vegfa) secretion by starved Vldlr$^{-/-}$ photoreceptors, attracting neovessels to supply fuel. These aberrant vessels invading normally avascular photoreceptors in Vldlr$^{-/-}$ retinas are reminiscent of retinal angiomatous proliferation (RAP), a subset of neovascular age-related macular degeneration (AMD) (Bottoni, F., et al. *Arch Ophthalmol* 123, 1644-1650 (2005)), associated with high vitreous VEGF levels in humans. Dysregulated lipid and glucose photoreceptor energy metabolism may therefore be a driving force in neovascular AMD and other retinal diseases.

Retinal neovascularization (RAP) is seen in macular telangiectasia (MacTel) (Yannuzzi, L. A., et al. *Retina* 32 Suppl 1, 450-460 (2012)) as well as in 15-20% of macular neovascular age-related macular degeneration (AMD) (Bottoni, F., et al. *Arch Ophthalmol* 123, 1644-1650 (2005)), the leading cause of blindness in older adults (Lim, L. S., *Lancet* 379, 1728-1738 (2012)). Photoreceptors, densest in the macula, are amongst the highest energy consuming and mitochondria-rich cells (Wong-Riley, *Eye Brain* 2, 99-116 (2010), and Okawa, *Curr Biol* 18, 1917-1921 (2008)) consistent with high-energy demands causing macular neovascularization. VEGF contributes to retinal neovascularization, but factors that initiate VEGF secretion in macular disease remain largely unknown. Disordered photoreceptor mitochondrial energy metabolism was hypothesized drive aberrant angiogenesis in the normally avascular photoreceptors in an attempt to increase fuel supply, consistent with dyslipidemia and mitochondrial dysfunction (associated with aging) being important risk factors of neovascular AMD (Lim, L. S., *Lancet* 379, 1728-1738 (2012).

Retinal neurons are thought to rely on glucose for fuel (Wong-Riley, *Eye Brain* 2, 99-116 (2010), and Cohen, L. H. & Noell, W. K. *J Neurochem* 5, 253-276 (1960)). Glucose is metabolized to pyruvate (by glycolysis) and either converted to lactate in cytosol, or oxidized into acetyl-CoA in mitochondria before entering the Krebs cycle to produce ATP. In photoreceptors, the major glucose transporter is GLUT1 (Mantych, G. J., *Endocrinology* 133, 600-607 (1993), and Gospe, S. M., *J Cell Sci* 123, 3639-3644 (2010)). Clinically, GLUT1 deficiency causes infantile seizures and developmental delay (Klepper, J. *Epilepsia* 49 Suppl 8, 46-49 (2008)), highlighting the importance of glucose metabolism in the brain. However, GLUT1 deficient individuals have normal vision suggesting alternative retinal energy substrates, perhaps through lipid β-oxidation.

Figure 1A:
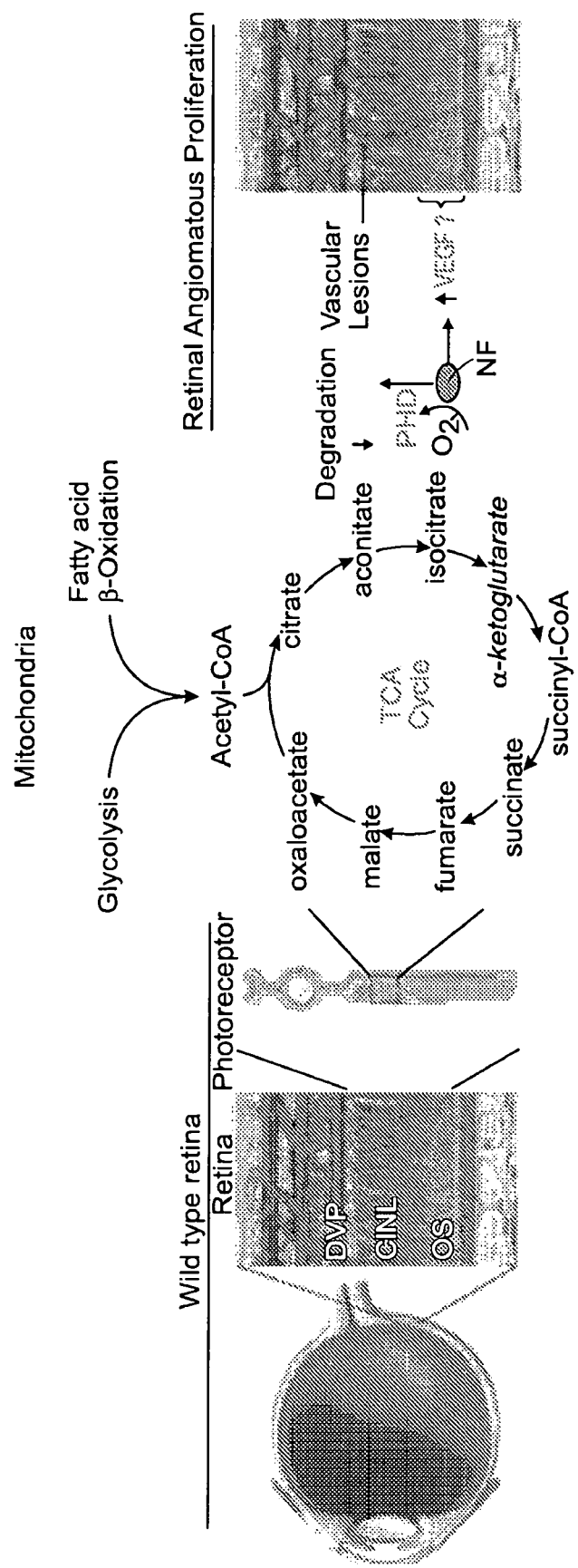
FIG. 1A depicts a schematic showing that retinal energy deficits are associated with vascular lesions in Vldlr$^{-/-}$. Photoreceptors have high metabolic rates, when adequate nutrients meet their energy demands, HIF is degraded and VEGF is not produced. Less substrate for glycolysis and fatty acid β-oxidation may decrease production of the Krebs cycle metabolite α-ketoglutarate, a co-factor of propyl hydroxylase (PHD) that tags HIF1α for degradation. HIF1α stabilization can trigger VEGF expression in photoreceptors, stimulating the development of pathologic neovascular lesions.
Figure 1B:
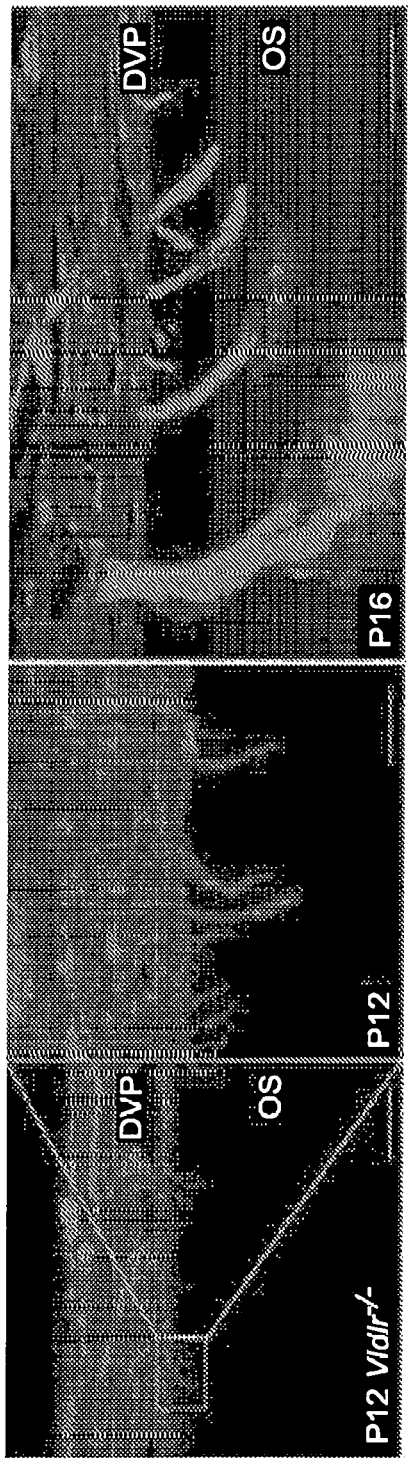
FIG. 1B depicts images showing pathologic vessels in Vldlr$^{-/-}$ retinas originated from the deep vascular plexus (DVP) and breached the outer plexiform layer (P12), extending towards photoreceptor outer segments (os) at P16; Scale: 200 μm. n=5 retinas.
Figure 1C:
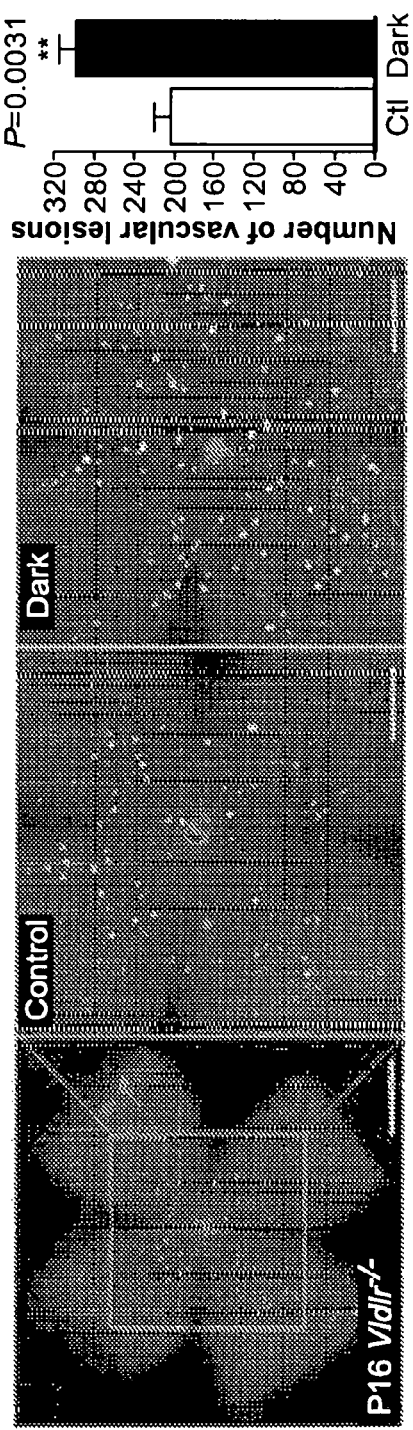
FIG. 1C depicts images and a bar graph of Vldlr$^{-/-}$ pups raised in darkness (n=10 retinas) compared to normal 12 hours light/dark cycle (Ctl: control, n=28) to increase retinal energy demands, scale: 1 mm (left), 0.5 mm (others). White spots label vascular lesions. (P=0.0031).
Figure 1D:
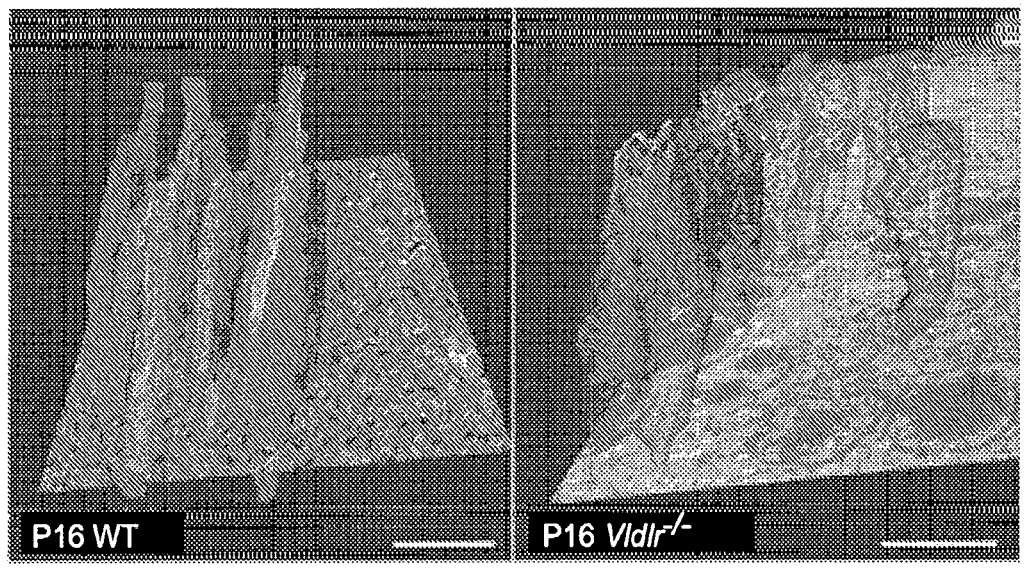
FIG. 1D depicts images showing mitochondrial volume quantified by 3D reconstruction of retinal scanning electron microscopy (SEM) images; mitochondria within photoreceptors (pseudo-colored); n=23 photoreceptors. Scale: 5 μm. P<0.0001.
Figure 1E:
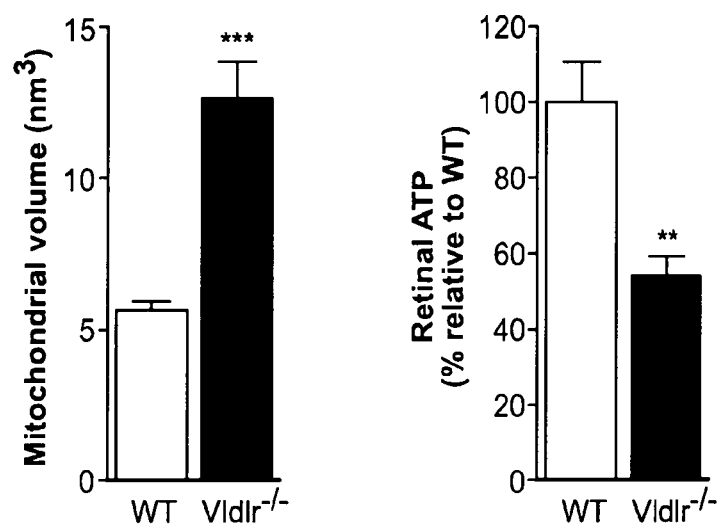
FIG. 1E depicts bar graphs showing that retinal ATP level was significantly lower in Vldlr$^{-/-}$ retina (n=6) compared to littermate control WT (n=4); two-tailed Student t-test,  P<0.01, * P<0.001. P=0.0026. Results are presented in as mean±SEM.

Lipid β-oxidation is common in heart and skeletal muscle with high metabolic rates, where abundant VLDLR facilitates fatty acid (FA) uptake (Lopaschuk, G. D., et al., *Physiol Rev* 90, 207-258 (2010)). VLDLR binds chylomicrons and enables cleavage of long-chain FA from triglycerides (TG)

by lipoprotein lipase (Goudriaan, J. R., et al. *J Lipid Res* 45, 1475-1481 (2004))(Goudriaan, J. R., et al. *Journal of lipid research* 45, 1475-1481 (2004)). VLDLR fosters transcytosis of active lipoprotein lipase across endothelial cells (Obunike, J. C., et al. *J Biol Chem* 276, 8934-8941 (2001)), to deliver free FA to tissue, Vldlr deletion suppresses lipid uptake and FA β-oxidation in the heart (Niu, Y.-G. & Evans, R. D. *J Lipids* 2011, 189876 (2011)). A similar mechanism in Vldlr-rich and lipid-rich photoreceptors was hypothesized. Lipid β-oxidation enzymes are expressed in the eye (Tyni, T., et al., *Pediatr Res* 56, 744-750 (2004)). Clinically, VLDLR deletion causes maculopathy (Sarac, O., et al., *Ophthalmic Genet* 33, 249-252 (2012)) and Vldlr$^{-/-}$ mice develop RAP-like retinal vascular lesions (FIG. 1A) (Dorrell, M. I., et al. *J Clin Invest* 119, 611-623 (2009)). Vldlr$^{-/-}$ mice allow exploration of the hypothesis that lipids fuel photoreceptors and fuel deficiency promotes neovessels.

Age-Related Macular Degeneration (AMD)

AMD is a common eye condition and a leading cause of vision loss among people age 50 and older. It causes damage to the macula, a small spot near the center of the retina and the part of the eye needed for sharp, central vision, which lets us see objects that are straight ahead. In some people, AMD advances so slowly that vision loss does not occur for a long time. In others, the disease progresses faster and may lead to a loss of vision in one or both eyes. As AMD progresses, a blurred area near the center of vision is a common symptom. Over time, the blurred area may grow larger or you may develop blank spots in your central vision. Objects also may not appear to be as bright as they used to be.

AMD by itself does not lead to complete blindness, with no ability to see. However, the loss of central vision in AMD can interfere with simple everyday activities, such as the ability to see faces, drive, read, write, or do close work, such as cooking or fixing things around the house.

Dyslipidemia

Dyslipidemia is characterized by an abnormal amount of lipids in the blood. In developed countries, most dyslipidemias are hyperlipidemias which are often due to diet and lifestyle. Dyslipidemias were traditionally classified by patterns of elevation in lipids and lipoproteins. A more practical system categorizes dyslipidemias as primary or secondary and characterizes them by increases in cholesterol only (pure or isolated hypercholesterolemia), increases in TGs only (pure or isolated hypertriglyceridemia), or increases in both cholesterol and TGs (mixed or combined hyperlipidemias).

Dyslipidemia usually causes no symptoms but can lead to symptomatic vascular disease, including coronary artery disease (CAD), stroke, and peripheral arterial disease. High levels of TGs (>1000 mg/dL [>11.3 mmol/L]) can cause acute pancreatitis. High levels of LDL can cause arcus corneae and tendinous xanthomas at the Achilles, elbow, and knee tendons and over metacarpophalangeal joints.

Mitochondrial Disease (Age-Related)

Mitochondrial disease is a chronic, genetic disorder that occurs when the mitochondria of the cell fail to produce enough energy for cell or organ function. The incidence is about 1:4000 individuals in the US. There are many forms of mitochondrial disease including, mitochondrial myopathy, diabetes mellitus, Leber's hereditary optic neuropathy, Leigh syndrome, neuropathy, ataxia, retinitis pigmentosa and ptosis (NARP), myoclonic epilepsy and ragged red fibers (MERRF) and mitochondrial myopathy, encephalomyopathy, lactic acidosis, stroke-like syndromes (MELAS).

Diseases of the mitochondria appear to cause the most damage to cells of the brain, heart, liver, skeletal muscles, kidney and the endocrine and respiratory systems. Depending on which cells are affected, symptoms may include loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection.

Macula

The macula is made up of millions of light-sensing cells that provide sharp, central vision. It is the most sensitive part of the retina, which is located at the back of the eye. The retina turns light into electrical signals and then sends these electrical signals through the optic nerve to the brain, where they are translated into the images we see. When the macula is damaged, the center of your field of view may appear blurry, distorted, or dark.

MacTel (Macular Telangiectasia)

Macular telangiectasia is a disease in which the macula is affected, causing a loss of central vision. The macula is a small area in the retina (the light-sensitive tissue lining the back of the eye) that is responsible for central vision, allowing fine details to be seen clearly. Macular telangiectasia develops when there are problems with the tiny blood vessels around the fovea, the center of the macula. There are two types of macular telangiectasia (Type 1 and Type 2), and each affects the blood vessels differently. Macular telangiectasia may occur as a result of a retinal vascular disease or a systemic disease such as diabetes or hypertension, but in many cases, clinical findings reveal no known cause.

One serious complication of macular telangiectasia is the development of abnormal blood vessels under the retina. This is called choroidal neovascularization, and may call for injections of a drug called vascular endothelial growth factor inhibitors (anti-VEGF). Anti-VEGF medication targets a specific chemical in the eye that causes abnormal blood vessels to grow under the retina. That chemical is called vascular endothelial growth factor, or VEGF. Blocking VEGF with medication injections reduces the growth of abnormal blood vessels, slows their leakage, helps to reduce swelling of the retina, and in some cases may improve vision.

Type 1 Macular Telangiectasia

In Type 1 macular telangiectasia, the blood vessels become dilated forming tiny aneurysms, causing swelling and damaging macular cells. The disease almost always occurs in one eye, which differentiates it from Type 2.

Type 2 Macular Telangiectasia

The most common form of macular telangiectasia is Type 2 macular telangiectasia, in which the tiny blood vessels around the fovea leak, become dilated (widen), or both. It is a bilateral disease of unknown cause, which characteristic alterations of macular capillary network and neurosensory atrophy. In some cases, new blood vessels form under the retina and they can also break or leak. Fluid from leaking blood vessels causes the macula to swell or thicken, a condition called macular edema, which affects central vision. Also, scar tissue can sometimes form over the macula and the fovea, causing loss of detail vision. Type 2 affects both eyes but not necessarily with the same severity.

RAP (Retinal Angiomatous Proliferation)

RAP describes a vascular process that originates within the neurosensory retina, beginning with capillary proliferation, formation of intraretinal neovascularization, and retinal-retinal anastamoses. RAP lesions have been characterized in the literature as having a poor natural history, but it is unclear what the reference group is. It is also unclear whether these statements refer to vision outcomes, anatomic outcomes, or both. Another recurring theme within the literature reporting on RAP lesions is that these lesions do not respond well to treatment, and that no definite therapy has been shown to be beneficial at reducing visual loss and controlling the lesion. This has led to the use of a variety of treatment modalities for these lesions, with the list of therapies resembling those that have been used for any AMD-related CNV lesion, including direct laser photocoagulation, transpupillary thermotherapy, surgical removal of the lesion, surgical excision of the retinal feeder vessels, photodynamic therapy (PDT) guided by fluorescein or indocyanine green (ICG) dye with and without intravitreal triamincolone, periocular anecortave acetate, anti-vascular endothelial growth factor (VEGF) regimens with pegaptanib sodium (EyeTech Pharmaceuticals, New York, USA), ranibizumab (Lucentis, Genentech Inc, South San Francisco, Calif., USA), or bevacizumab (Avastin, Genentech Inc., South San Francisco, Calif., USA), or various combinations of the above.

Retinopathy of Prematurity (ROP)

Retinopathy of prematurity (ROP) is a potentially blinding eye disorder that primarily affects premature infants weighing about 2¾ pounds (1250 grams) or less that are born before 31 weeks of gestation (A full-term pregnancy has a gestation of 38-42 weeks). The smaller a baby is at birth, the more likely that baby is to develop ROP. This disorder which usually develops in both eyes is one of the most common causes of visual loss in childhood and can lead to lifelong vision impairment and blindness. ROP was first diagnosed in 1942.

With advances in neonatal care, smaller and more premature infants are being saved. These infants are at a much higher risk for ROP. Not all babies who are premature develop ROP. There are approximately 3.9 million infants born in the U.S. each year; of those, about 28,000 weigh 2¾ pounds or less. About 14,000-16,000 of these infants are affected by some degree of RO', The disease improves and leaves no permanent damage in milder cases of ROP. About 90 percent of all infants with ROP are in the milder category and do not need treatment. However, infants with more severe disease can develop impaired vision or even blindness. About 1,100-1,500 infants annually develop ROP that is severe enough to require medical treatment. About 400-600 infants each year in the US become legally blind from ROP.

ROP is classified in five stages, ranging from mild (stage I) to severe (stage V):

Stage I—Mildly abnormal blood vessel growth. Many children who develop stage I improve with no treatment and eventually develop normal vision. The disease resolves on its own without further progression.

Stage II—Moderately abnormal blood vessel growth. Many children who develop stage II improve with no treatment and eventually develop normal vision. The disease resolves on its own without further progression.

Stage III—Severely abnormal blood vessel growth. The abnormal blood vessels grow toward the center of the eye instead of following their normal growth pattern along the surface of the retina. Some infants who develop stage III improve with no treatment and eventually develop normal vision. However, when infants have a certain degree of Stage III and "plus disease" develops, treatment is considered. "Plus disease" means that the blood vessels of the retina have become enlarged and twisted, indicating a worsening of the disease. Treatment at this point has a good chance of preventing retinal detachment.

Stage IV—Partially detached retina. Traction from the scar produced by bleeding, abnormal vessels pulls the retina away from the wall of the eye.

Stage V—Completely detached retina and the end stage of the disease. If the eye is left alone at this stage, the baby can have severe visual impairment and even blindness.

Most babies who develop ROP have stages I or II. However, in a small number of babies, ROP worsens, sometimes very rapidly. Untreated ROP threatens to destroy vision.

Infants with ROP are considered to be at higher risk for developing certain eye problems later in life, such as retinal detachment, myopia (nearsightedness), strabismus (crossed eyes), amblyopia (lazy eye), and glaucoma. In many cases, these eye problems can be treated or controlled.

ROP occurs when abnormal blood vessels grow and spread throughout the retina, the tissue that lines the back of the eye. These abnormal blood vessels are fragile and can leak, scarring the retina and pulling it out of position. This causes a retinal detachment. Retinal detachment is the main cause of visual impairment and blindness in ROP.

Several complex factors may be responsible for the development of ROP. The eye starts to develop at about 16 weeks of pregnancy, when the blood vessels of the retina begin to form at the optic nerve in the back of the eye. The blood vessels grow gradually toward the edges of the developing retina, supplying oxygen and nutrients. During the last 12 weeks of a pregnancy, the eye develops rapidly. When a baby is born full-term, the retinal blood vessel growth is mostly complete (The retina usually finishes growing a few weeks to a month after birth). But if a baby is born prematurely, before these blood vessels have reached the edges of the retina, normal vessel growth may stop. The edges of the retina—the periphery—may not get enough oxygen and nutrients.

It is believed that the periphery of the retina then sends out signals to other areas of the retina for nourishment. As a result, new abnormal vessels begin to grow. These new blood vessels are fragile and weak and can bleed, leading to retinal scarring. When these scars shrink, they pull on the retina, causing it to detach from the back of the eye.

To date, the most effective proven treatments for ROP are laser therapy or cryotherapy. Laser therapy "burns away" the periphery of the retina, which has no normal blood vessels. With cryotherapy, physicians use an instrument that generates freezing temperatures to briefly touch spots on the surface of the eye that overlie the periphery of the retina. Both laser treatment and cryotherapy destroy the peripheral areas of the retina, slowing or reversing the abnormal growth of blood vessels. Unfortunately, the treatments also destroy some side vision. This is done to save the most important part of our sight the sharp, central vision we need for "straight ahead" activities such as reading, sewing, and driving.

Both laser treatments and cryotherapy are performed only on infants with advanced ROP, particularly stage III with "plus disease." Both treatments are considered invasive surgeries on the eye, and doctors don't know the long-term side effects of each.

In the later stages of ROP, other treatment options include:
Sacral buckle. This involves placing a silicone band around the eye and tightening it. This keeps the vitreous gel from pulling on the scar tissue and allows the retina to flatten back down onto the wall of the eye. Infants who have had a sclera buckle need to have the band removed months or years later, since the eye continues to grow; otherwise they will become nearsighted. Sclera buckles are usually performed on infants with stage IV or V.

Vitrectomy. Vitrectomy involves removing the vitreous and replacing it with a saline solution. After the vitreous has been removed, the scar tissue on the retina can be peeled back or cut away, allowing the retina to relax and lay back down against the eye wall. Vitrectomy is performed only at stage V.

While ROP treatment decreases the chances for vision loss, it does not always prevent it. Not all babies respond to ROP treatment, and the disease may get worse. If treatment for ROP does not work, a retinal detachment may develop. Often, only part of the retina detaches (stage IV). When this happens, no further treatments may be needed, since a partial detachment may remain the same or go away without treatment. However, in some instances, physicians may recommend treatment to try to prevent further advancement of the retinal detachment (stage V). If the center of the retina or the entire retina detaches, central vision is threatened, and surgery may be recommended to reattach the retina.

FFA1 (Also Referred to as GPR40)

By "Free fatty acid receptor 1" or "FFA1" is also referred to as GPR40, a class A G-protein couple receptor, encoded by the Ffar1 gene. FFA1 is activated by medium to long chain fatty acids. GPCRs are membrane proteins characterized as having seven putative transmembrane domains that respond to a variety of molecules by activating intra-cellular signaling pathways critical to a diversity of physiological functions. FFA1 was first identified as an orphan receptor (i.e., a receptor without a known ligand) from a human genomic DNA fragment. FFA1 is highly expressed in pancreatic β cells and insulin-secreting cell lines. FFA1 activation is linked to modulation of the Gq family of intra-cellular signaling proteins and concomitant induction of elevated calcium levels. It has been recognized that fatty acids serve as ligands for FFA1, and that fatty acids regulate insulin secretion through FFA1. Modulation (e.g., selective agonist stimulation) of the G-protein coupled receptor results in phospholipase C activation, and production of inositol 1,4,5-triphosphate and diacylglycerol, and increased levels of intracellular calcium, which activates caspase-dependent apoptotic pathways (Tsujihata, et al., *J Pharmacol Exp Ther* 339: 228-237 (2011); and Briscoe, et al. J Bio Chem 278, 11303-11311 (2003)). GPR40 agonists (e.g., by selective agonist stimulation) have been used to inhibit the growth or induce apoptosis of certain cancer cells (e.g., cancers derived from neural crest tissues). Furthermore, GPR40 agonists have been reported to result in a cytotoxic effect on certain cancers and cancer cell lines. Agonist stimulation of GPR40 (e.g., via aomega-3 fatty acids) activates signaling pathways that inhibit and are useful for the treatment and/or prevention of cancers.

GPCRs are membrane proteins having seven transmembrane domains, and can respond to a variety of molecules, thereby activating intracellular signaling transduction pathways, and are critical for achieving a variety of physiological functions. FFA1 was the first fatty acid receptor to be identified on the cell surface, capable of binding the most common fatty acids in plasma such as palmitate, oleate, stearate, linoleate, and linolenate, and the like. FFA1 could be considered as a nutrient sensing receptor, playing several tissue-dependent roles, which may affect overall glucose utilization and/or fat metabolism. For example, long-chain FFAs amplify GSIS in pancreatic 13 cells through the activation of FFA1. A series of FFA1 agonists have been disclosed by some patent applications, such as WO2005087710, WO2005051890, and WO2004106276.

Other GPCRs

Other GPCRs contemplated for targeting by the compositions, formulations and methods of the instant invention include GPR120, GPR44 (also referred to as prostaglandin $D_2$ receptor 2 ($DP_2$), GPR42, GPR84, and human equivalents. GPR120, for example, has been shown to mediate the anti-inflammatory and insulin-sensitizing effects of omega 3 fatty acids, and a deficiency of GPR120 is responsible for reduced fat metabolism, thereby leading to obesity. An Exemplary GPR120 inhibitor may include 4-Methyl-N-9H-xanthen-9-yl-benzenesulfonamide.

In another example, GPR84 is a receptor for medium-chain FFA with carbon chain lengths of C9 to C14. Its expression is highly inducible in inflammation and its expression on neutrophils can be increased with LPS stimulation and reduced with GM-CSF stimulation. GPR84 is not activated by short-chain and long-chain saturated and unsaturated FFAs induced in onocytes/macrophages by LPS. In addition, the activation of GPR84 in monocytes/macrophages may amplify LPS stimulated IL-12 p40 production in a concentration dependent manner. An exemplary GPR 84 inhibitor is GLPG1205.

Diabetic Retinopathy

Diabetic retinopathy describes a diabetic eye disease that affects blood vessels in the retina and is both the most common cause of vision loss among people with diabetes and the leading cause of vision impairment and blindness among working-age adults. Chronically high blood sugar from diabetes is associated with damage to the blood vessels in the retina, thereby leading to diabetic retinopathy. This changes the curvature of the lens and results in the development of symptoms of blurred vision. The blurring of distance vision as a result of lens swelling will subside once the blood sugar levels are brought under control. Better control of blood sugar levels in patients with diabetes also slows the onset and progression of diabetic retinopathy. Symptoms of diabetic retinopathy may include seeing spots or floaters in a subject's field of vision, blurred vision, having a dark or empty spot in the center of a subject's vision, and difficulty seeing well at night. Diabetic retinopathy may progress through four stages:

I. Mild nonproliferative retinopathy: small areas of swelling in the retinal blood vessels causing tiny bulges, called microaneurysms to protrude from their walls may occur.

II. Moderate nonproliferative retinopathy: progression of the disease may lead to blood vessels swelling and distorting, therefore affecting their ability to transport blood.

III. Severe nonproliferative retinopathy: more blood vessels become blocked, depriving the blood supply to areas of the retina.

IV. Proliferative diabetic retinopathy: advanced stage of the disease where growth factors secreted by the retina trigger the proliferation of new blood vessels, which grow along the inside surface of the retina and into the fluid that fills the eye. The fragility of the new blood vessels makes them more likely to leak and bleed. Scar tissue can cause retinal detachment (pulling away of the retina from underlying tissue). Retinal detachment can lead to permanent vision loss.

The fatty acid receptor GPR40 has drawn attention as a potential therapeutic target for treatment of type II diabetes. The art provides support for the notion that activation of GPR40 improves glucose tolerance, which may in turn be beneficial for the treatment of type II diabetes (e.g., agonist TAK-875). However, the literature remains unclear regarding whether inhibition of GPR40 would be beneficial to treat type II diabetes. A small molecule antagonist (DC260126), has been demonstrated to protect against pancreatic β-cell dysfunction by reducing β-cell overload.

FFA1 Inhibitors

Inhibitors of FFA1 are contemplated for use in the methods and compositions of the invention. Such inhibitors include both small molecules and nucleic acid inhibitory agents. Small molecule inhibitors of FFA1 include the following.

GW-1100 (ethyl 4-[5-[(2-ethoxypyrimidin-5-yl)methyl]-2-[(4-fluorophenyl)methylsulfanyl]-4-oxopyrimidin-1-yl]benzoate) is a known inhibitor of FFA1, having the following structure.

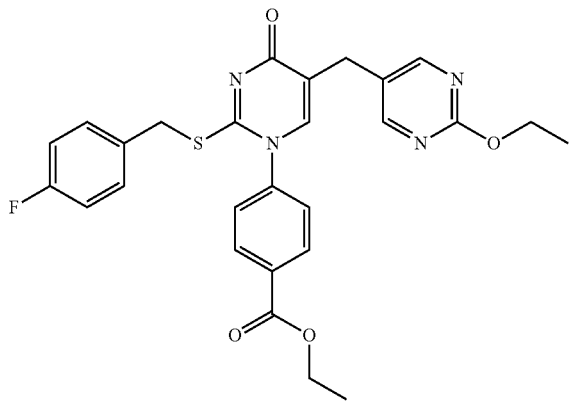 [SMILES: CCOC(=O)c1ccc(-n2cc(Cc3cnc(OCC)nc3)c(=O)nc2SCc2ccc(F)cc2)cc1]

DC260126 (N-(4-Butylphenyl)-4-fluoro-benzenesulfonamide) is another compound identified as a small-molecule antagonist of GPR40 (Sun et al. PLOS DOI: 10.1371/journal.pone.0066744), possessing the following structure.

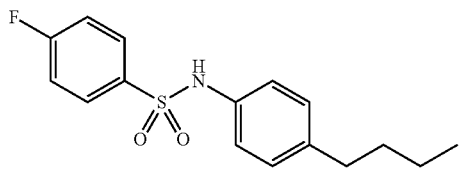 [SMILES: CCCCc1ccc(NS(=O)(=O)c2ccc(F)cc2)cc1]

Other art-recognized inhibitors of FFA1, and of GPCRs more generally include, e.g., pertussis toxin.

The above-described FFA1 inhibitory compounds are merely exemplary, as any art-recognized FFA1 inhibitor is contemplated for use in the methods and compositions of the invention.

Neuronal Degeneration

Neuronal degeneration is characterized by a progressive loss of structure and function of neurons and including death of neurons. Many neurodegenerative diseases including amyotrophic lateral sclerosis, Parkinson's Disease, Alzheimer's Disease, and Huntington's Disease occur as a result of neurodegenerative processes. Such diseases are incurable, resulting in progressive degeneration and/or death of neuron cells. Only an extremely small portion (less than 5%) of neurodegenerative diseases are caused by genetic mutations and the remainder are caused by a build up of toxic proteins in the brain and a loss of mitochondrial function, thereby leading to the increased levels of neurotoxic molecules. As research progresses, many similarities appear that relate these diseases to one another on a subcellular level. There are many parallels between different neurodegenerative disorders including atypical protein assemblies as well as induced cell death. Neurodegeneration can be found in many different levels of neuronal circuitry ranging from molecular to systemic. The greatest risk factor for neurodegenerative diseases is aging. Mitochondrial DNA mutations as well as oxidative stress both contribute to aging. Many of these diseases are late-onset, and an underlying factor in each disease is the gradual loss of function of the neurons with age. There are currently no therapies available to cure neurodegeneration. For each of the diseases, medication can only alleviate symptoms and help to improve patients' quality of life.

Cancer

The invention may further provide methods for the treatment of cancer, and more specifically may be used to alter the metabolism of malignant cells. Cancer may be referred to as an uncontrolled growth of cells which interferes with the normal functioning of the bodily systems. Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer.

Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

Inhibitory Nucleic Acids

A siRNA, shRNA or other inhibitory nucleic acid of the invention can also be expressed from recombinant viral vectors intracellularly at or near the area of neovascularization in vivo. The recombinant viral vectors of the invention comprise sequences encoding the siRNA, shRNA or other inhibitory nucleic acid of the invention and any suitable promoter for expressing the siRNA, shRNA or other inhibitory nucleic acid sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA, shRNA or other inhibitory nucleic acid in a particular tissue or in a particular intracellular environment. The use of recombinant viral vectors to deliver a siRNA, shRNA or other inhibitory nucleic acid of the invention to cells in vivo is discussed in more detail below.

A siRNA, shRNA or other inhibitory nucleic acid of the invention can be expressed from a recombinant viral vector either as two separate, complementary RNA molecules, or as a single RNA molecule with two complimentary regions.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked.

In general, the vectors useful in the invention include, but are not limited to, plasmids, phagemids, viruses, other vehicles derived from viral or bacterial sources that have been manipulated by the insertion or incorporation of nucleic acid according to the invention. Viral vectors are an exemplary type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Certain viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Murry, "Methods in Molecular Biology," vol. 7, Humana Press, Inc., Chiffon, N.J., 1991.

Certain viruses useful for delivery of nucleic acid agents of the invention are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu Z, Asokan A, Samulski R J: Adeno-associated virus serotypes: vector toolkit for human gene therapy. Mol Ther 14:316-327, 2006). Recombinant AAV are derived from the dependent parvovirus AAV2 (Choi V W, Samulski R J, McCarty D M: Effects of adeno-associated virus DNA hairpin structure on recombination. J Virol 79:6801-6807, 2005). The adeno-associated virus type 1 to 12 can be engineered to be replication deficient and is capable of infecting a wide range of cell types and species (Wu Z, Asokan A, Samulski R J: Adeno-associated virus serotypes: vector toolkit for human gene therapy. Mol Ther 14:316-327, 2006). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion and most recombinant adenovirus are extrachromosomal. In the sheltered environment of the retina, AAV vectors are able to maintain high levels of transgene expression in the retinal pigmented epithelium (RPE), photoreceptors, or ganglion cells for long periods of time after a single treatment. Each cell type can be specifically targeted by choosing the appropriate combination of AAV serotype, promoter, and intraocular injection site (Dinculescu et al., Hum Gene Ther. 2005 June; 16(6): 649-63 and Lebherz, C., Maguire, A., Tang, W., Bennett, J. & Wilson, J. M. Novel AAV serotypes for improved ocular gene transfer. J Gene Med 10, 375-82 (2008)). In one embodiment, AAV serotype 8 is particularly suitable.

Any viral vector capable of accepting the coding sequences for the siRNA, shRNA or other inhibitory nucleic acid molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), Gene Therap. 2: 301-310; Eglitis M A (1998), Biotechniques 6: 608-614; Miller A D (1990), Hum Gene Therap. 1: 5-14; and Anderson W F (1998), Nature 392: 25-30, the entire disclosures of which are herein incorporated by reference.

Optionally, viral vectors derived from AV and AAV are employed. In certain embodiments, the siRNA, shRNA or other inhibitory nucleic acid of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA, shRNA or other inhibitory nucleic acid of the invention, a method for constructing the recombinant AV vector, and a method for delivering the vector into target cells, are described in Xia H et al. (2002), Nat. Biotech. 20: 1006-1010.

Suitable AAV vectors for expressing the siRNA, shRNA or other inhibitory nucleic acid of the invention, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosure of which are herein incorporated by reference.

Non-viral administration of nucleic acid in vivo has been accomplished by a variety of methods. These include lipofectin/liposome fusion Proc Natl Acad Sci 84, pp 7413-7417 (1993), polylysine condensation with and without adenovirus enhancement Human Gene Therapy 3, pp 147-154 (1992), and transferrin transferring receptor delivery of nucleic acid to cells Proc Natl Acad Sci 87, pp 3410-3414 (1990) The use of a specific composition consisting of polyacrylic acid has been disclosed in WO 94/24983 Naked DNA has been administered as disclosed in WO90/11092.

In certain embodiments, the use of liposomes and/or nanoparticles is contemplated for the introduction of a nucleic acid of the invention into target cells.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core.

Synthetic cationic lipids designed to limit the difficulties and dangers encountered with liposome mediated transfection can be used to prepare liposomes for in vivo transfection of a nucleic acid. The use of cationic lipids may promote encapsulation of negatively charged nucleic acids, and also promote fusion with negatively charged cell membranes (Felgner et al., 1989).

Alternatively, one of the simplest and the safest ways to deliver the nucleic acid according across cell membranes in vivo may involve the direct application of high concentration free or naked polynucleotides (typically mRNA or DNA). By "naked DNA (or RNA)" is meant a DNA (RNA) molecule which has not been previously complexed with other chemical moieties. Naked DNA uptake by animal cells may be increased by administering the cells simultaneously with excipients and the nucleic acid. Such excipients are reagents that enhance or increase penetration of the DNA across cellular membranes and thus delivery to the cells delivery of the therapeutic agent. Various excipients have been described in the art, such as surfactants, e.g. a surfactant selected form the group consisting of Triton X-100, sodium dodecyl sulfate, Tween 20, and Tween 80; bacterial toxins, for instance streptolysin O, cholera toxin, and recombinant modified labile toxin of E coli; and polysaccharides, such as glucose, sucrose, fructose, or maltose, for instance, which act by disrupting the osmotic pressure in the vicinity of the cell membrane. Other methods have been described to enhance delivery of free polynucleotides, such as blocking of polynucleotide inactivation via endo—or exonucleolytic cleavage by both extra—and intracellular nucleases.

In certain embodiments, a nucleic acid of the invention is under the control of a heterologous regulatory region, e.g., a heterologous promoter. The promoter can be a generally active promoter, or in certain embodiments, can be, e.g., an eye and/or photoreceptor specific promoter, such as the three versions of the human red cone opsin promoter (PROS, 3LCR-PRO.5 and PR2.1), the human blue cone opsin promoter HB569 (Gene Ther. 2008 July; 15(14):1049-55. Epub 2008 Mar. 13., Targeting gene expression to cones with human cone opsin promoters in recombinant AAV. Komáromy A M, Alexander J J, Cooper A E, Chiodo V A, Glushakova L G, Acland G M, Hauswirth W W, Aguirre G D); three photoreceptor specific promoters (interphotoreceptor retinoid binding protein-IRPB1783; guanylate cyclase activating protein 1-GCAP292; rhodopsin-mOP500) '(Mol Vis. 2007 Oct. 18; 13:2001-11. Targeted expression of two proteins in neural retina using self-inactivating, insulated lentiviral vectors carrying two internal independent promoters. Semple-Rowland S L, Eccles K S, Humberstone E J.) the human rhodopsin kinase (RK) promoter (Invest Ophthalmol Vis Sci. 2007 September; 48(9):3954-61. AAV-mediated expression targeting of rod and cone photoreceptors with a human rhodopsin kinase promoter. Khani S C, Pawlyk B S, Bulgakov O V, Kasperek E, Young J E, Adamian M, Sun X, Smith A J, Ali R R, Li T.); the promoter for the alpha subunit of cone transducin or the cone photoreceptor regulatory element 1 (CPRE-1) a novel 20-bp enhancer element in the TalphaC promoter (J Biol Chem. 2008 Apr. 18; 283(16):10881-91. Epub 2008 Feb. 13. A novel, evolutionarily conserved enhancer of cone photoreceptor-specific expression. Smyth V A, Di Lorenzo D, Kennedy B N.), the promoter of the orphan nuclear receptor Nr2e3; the promoter of human retinal guanylate cyclase 1 (retGC1), and the cone transcription factor Trβ2 [(Peng and Chen, 2005; Oh et al., 2007) promoter for the beta subunit of the phosphodiesterase, PDE6B (Mali et al., 2007). The promoter can also optionally be selected form the group of genes consisting of human rhodopsin (hRHO), human red opsin (hRO), human green opsin and mouse cone arrestin-3 (mCAR). In a certain embodiments, mouse cone arrestin-3 (mCAR) can be used.

Suitable methods, i.e., invasive and noninvasive methods, of administering a nucleic acid of the invention, optionally so as to contact a photoreceptor, are well known in the art. Although more than one route can be used to administer a nucleic acid, certain routes can provide a more immediate and more effective reaction than other routes. Accordingly, the described routes of administration are merely exemplary and are in no way limiting. Accordingly, the methods are not dependent on the mode of administering the nucleic acid of the invention to an animal, optionally a human, to achieve the desired effect. As such, any route of administration is appropriate so long as the nucleic acid of the invention targets an appropriate host cell (e.g., an eye cell, e.g., a retinal and/or retinal-associated cell involved in treating or preventing angiogenesis upon FFA1 inhibition). A nucleic acid of the invention can be appropriately formulated and administered in the form of an injection, eye lotion, ointment, implant and the like. A nucleic acid of the invention can be applied, for example, systemically, topically, subconjunctivally, intraocularly, retrobulbarly, periocularly, subretinally, or suprachoroidally. In certain cases, it may be appropriate to administer multiple applications and employ multiple routes, e.g., subretinal and intravitreous, to ensure sufficient exposure of targeted eye cells (e.g., retinal cells and/or retina-associated cells) to the nucleic acid of the invention. Multiple applications of the nucleic acid of the invention may also be required to achieve a desired effect.

Depending on the particular case, it may be desirable to non-invasively administer a nucleic acid of the invention to a patient. For instance, if multiple surgeries have been performed, the patient displays low tolerance to anesthetic, or if other ocular-related disorders exist, topical administration of the nucleic acid according to the invention may be most appropriate. Topical formulations are well known to those of skill in the art. Such formulations are, suitable in the context of the present invention for application to the eye. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art. A nucleic acid of the invention can also be administered non-invasively using a needleless injection device, such as the Biojector 2000 Needle-Free Injection Management System@ available from Bioject, Inc.

A nucleic acid of the invention can optionally be present in or on a device that allows controlled or sustained release of the nucleic acid according, such as an ocular sponge, meshwork, mechanical reservoir, or mechanical implant. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), such as an implantable device, e.g., a mechanical reservoir, an intraocular device or an extraocular device with an intraocular conduit, or an implant or a device comprised of a polymeric composition are particularly useful for ocular administration of the nucleic acid according to the invention. A nucleic acid according to the invention can also be administered in the form of sustained-release formulations (see, e.g., U.S. Pat. No. 5,378,475) comprising, for example, gelatin, chondroitin sulfate, a polyphosphoester, such as bis-2-hydroxyethyl-terephthalate (BHET), or a polylacticglycolic acid.

Alternatively, a nucleic acid according to the invention can be administered using invasive procedures, such as, for instance, intravitreal injection or subretinal injection optionally preceded by a vitrectomy. Subretinal injections can be administered to different compartments of the eye, i.e., the anterior chamber. While intraocular injection is preferred, injectable compositions can also be administered intramuscularly, intravenously, and intraperitoneally. Pharmaceutically acceptable carriers for injectable compositions are well-known to those of ordinary skill in the art (see Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 41h ed., pages 622-630 (1986)). A nucleic acid according to the invention can also be administered in vivo by particle bombardment, i.e., a gene gun. Optionally, a nucleic acid of the invention is administered via an ophthalmologic instrument for delivery to a specific region of an eye. Use of a specialized ophthalmologic instrument can ensure precise administration of the nucleic acid while minimizing damage to adjacent ocular tissue. Delivery of a nucleic acid of the invention to a specific region of the eye also limits exposure of unaffected cells to nucleic acid of the invention, thereby reducing the risk of side effects. An exemplary ophthalmologic instrument is a combination of forceps and subretinal needle or sharp bent cannula. Alternatively, a nucleic acid of the invention may be injected directly into the vitreous, aqueous humour, ciliary body tissue(s) or cells and/or extraocular muscles by electroporation or iontophoresis means.

The dose of a nucleic acid of the invention administered to an animal, particularly a human, in accordance with the present invention should be sufficient to effect the desired response in the animal over a reasonable time frame. One skilled in the art will recognize that dosage will depend upon a variety of factors, including the age, species, the pathology in question, and condition or disease state. Dosage also depends on the nucleic acid to be expressed and/or active, as well as the amount of ocular tissue about to be affected or actually affected by the neural cell (e.g., retinal cell) disease or disorder. The size of the dose also will be determined by the route, timing, and frequency of administration as well as the existence, nature, and extent of any adverse side effects that might accompany the administration of a particular nucleic acid according to the invention and the desired physiological effect. It will be appreciated by one of ordinary skilled in the art that various conditions or disease states, in particular, chronic conditions or disease states, may require prolonged treatment involving multiple administrations.

A nucleic acid of the invention can be administered in a pharmaceutical composition, which comprises a pharmaceutically acceptable carrier and the nucleic acid(s) of the invention. Any suitable pharmaceutically acceptable carrier can be used within the context of the present invention, and such carriers are well known in the art. The choice of carrier will be determined, in part, by the particular site to which the composition is to be administered and the particular method used to administer the composition.

Suitable formulations include aqueous and non-aqueous solutions, isotonic sterile solutions, which can contain antioxidants, buffers, bacteriostats, and solutes that render the formulation isotonic with the blood or intraocular fluid of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Optionally, the pharmaceutically acceptable carrier is a buffered saline solution. In certain embodiments, a nucleic acid of the invention for use in the present inventive methods is administered in a pharmaceutical composition formulated to protect the nucleic acid of the invention from damage prior to administration. For example, the pharmaceutical composition can be formulated to reduce loss of the nucleic acid of the invention on devices used to prepare, store, or administer the nucleic acid of the invention, such as glassware, syringes, or needles. The pharmaceutical composition can be formulated to decrease the light sensitivity and/or temperature sensitivity of the nucleic acid of the invention. To this end, the pharmaceutical composition optionally comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a pharmaceutical composition will extend the shelf life of the nucleic acid, facilitate administration, and increase the efficiency of the methods of the invention. In this regard, a pharmaceutical composition also can be formulated to enhance transduction efficiency.

In addition, one of ordinary skill in the art will appreciate that a nucleic acid can be present in a composition with other therapeutic or biologically-active agents. For example, therapeutic factors useful in the treatment of a particular indication can be present. For instance, if treating vision loss, hyaluronidase can be added to a composition to effect the breakdown of blood and blood proteins in the vitreous of the eye. Factors that control inflammation, such as ibuprofen or steroids, can be part of the composition to reduce swelling and inflammation associated with in vivo administration of the nucleic acid according to the invention and ocular distress. Immune system suppressors can be administered in combination to reduce any immune response to the nucleic acid itself. Similarly, vitamins and minerals, anti-oxidants, and micronutrients can be co-administered. Antibiotics, i.e., microbicides and fungicides, can be present to reduce the risk of infection associated with gene transfer procedures and other disorders.

The present invention also relates to pharmaceutical compositions comprising an isolated nucleic acid according to the invention.

The present invention also relates to a method for treating a neural cell (e.g., retinal cell) disease or disorder comprising administering a patient in need thereof with a therapeutically effective amount of an isolated nucleic acid according to the invention.

The ability of a siRNA, shRNA or other inhibitory nucleic acid containing a given target sequence to cause RNAi-mediated degradation of the target mRNA can be evaluated using standard techniques for measuring the levels of RNA or protein in cells. For example, siRNA, shRNA or other inhibitory nucleic acid of the invention can be delivered to cultured cells, and the levels of target mRNA can be measured by Northern blot or dot blotting techniques, or by quantitative RT-PCR. Alternatively, the levels of FFA1 protein in, e.g., cultured cells and/or cells of a subject, can be measured by ELISA or Western blot.

RNAi-mediated degradation of target mRNA by a siRNA, shRNA or other inhibitory nucleic acid containing a given target sequence can also be evaluated with animal models of retinal angiogenesis, such as the mouse models described herein. For example, areas of angiogenesis/neovascularization in a mouse can be measured before and after administration of a siRNA, shRNA or other inhibitory nucleic acid of the invention. A reduction in the areas of angiogenesis/neovascularization in such mice upon administration of the siRNA, shRNA or other inhibitory nucleic acid indicates the down-regulation of the target mRNA (e.g., Ffar1).

Pharmaceutical Compositions

Another aspect of the invention pertains to pharmaceutical compositions of the compounds of the invention. The pharmaceutical compositions of the invention typically comprise a compound of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer, or in a fat pad described herein. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, certain methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., FFA1 inhibitor) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Exemplary dosages of compounds (e.g., FFA1 inhibitor) of the invention include e.g., about 0.0001% to 5%, about 0.0001% to 1%, about 0.0001% to 0.1%, about 0.001% to 0.1%, about 0.005%-0.1%, about 0.01% to 0.1%, about 0.01% to 0.05% and about 0.05% to 0.1%.

The compound(s) of the invention can be administered in a manner that prolongs the duration of the bioavailability of the compound(s), increases the duration of action of the compound(s) and the release time frame of the compound by an amount selected from the group consisting of at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks, and at least a month, but at least some amount over that of the compound(s) in the absence of the fat pad delivery system. Optionally, the duration of any or all of the preceding effects is extended by at least 30 minutes, at least an hour, at least 2 hours, at least 3 hours, at least 6 hours, at least 12 hours, at least 24 hours, at least 48 hours, at least 72 hours, at least 4 days, at least 5 days, at least 6 days, at least 7 days, at least 2 weeks, at least 3 weeks or at least a month.

A compound of the invention can be formulated into a pharmaceutical composition wherein the compound is the only active agent therein. Alternatively, the pharmaceutical composition can contain additional active agents. For example, two or more compounds of the invention may be used in combination. Moreover, a compound of the invention can be combined with one or more other agents that have modulatory effects on cancer.

Kits

The invention also includes kits that include a composition of the invention, optionally also including a compound (e.g., a FFA1 inhibitor), and instructions for use.

This invention is further illustrated by the following examples which should not be construed as limiting. The contents of all references, patents, and published patent applications cited throughout this application, as well as the figures, are incorporated herein by reference.

EXAMPLES

Example 1: Materials and Methods

Animals

All studies adhered to the NIH guide for the Care and Use of laboratory animals, the Association for Research in Vision and Ophthalmology (ARVO) Statement for the Use of Animals in Ophthalmic and Vision Research and were approved by the Institutional Animal Care and Use Committee at Boston Children's Hospital. Vldlr knockout mice (Vldlr$^{-/-}$; Jackson Lab Stock: 002529) were crossed with wild type C57Bl/6 mice to obtain heterozygous breeders for littermate controlled experiments. Vldlr$^{-/-}$ mice were also crossed with Ffar1 knockout mice (Ffar1$^{-/-}$)[1] to ultimately obtain Vldlr$^{-/-}$/Ffar1$^{-/+}$ heterozygous breeders and double knockout mice (Vldlr$^{-/-}$/Ffar1$^{-/-}$). Pups weighing less than 5 grams or more than 7 grams at postnatal day (P)16 were excluded (Stahl, A., et al. *Am J Pathol* 177, 2715-2723 (2010)). Littermate Vldlr$^{-/-}$ pups were treated from P8 to P15 with WY164363 (50 mg/kg once daily, intraperitoneal; Sigma), GW9508 (14 µM, once daily intraperitoneal; Cayman), TAK-875 (15 mg/kg twice daily, gavage; Selleckchem), medium chain triglyceride oil (MCT, 20 µL once daily gavage; Nestle) or corresponding vehicle and sacrificed at P16 to quantify retinal vascular lesions. Mice pups of both genders were used.

Quantification of Vascular Lesions

For quantification of outer retina vascular lesions, reminiscent of retinal angiomatous proliferation (RAP) or macular telangiectasia (MacTel), mice were euthanized with a mixture of xylazine and ketamine and eyes were enucleated and fixed in 4% paraformaldehyde for 1 h at room temperature. Retinas were dissected, carefully removing all hyaloid vessels, and stained overnight at room temperature with fluoresceinated Isolectin B$_4$ (lectin) (Alexa Fluor 594-I21413, Molecular Probes) in 1 mM CaCl$_2$ in PBS. Lectin-stained retinas were whole-mounted onto Superfrost/Plus microscope slides (Fisher Scientific) with the photoreceptor side up and embedded in SlowFade Antifade reagent (Invitrogen). For quantification of retinal lesions 20 images of each whole-mounted retina were obtained at 10× magnification on a Zeiss AxioObserver.Z1 microscope and merged to form one image using AxioVision 4.6.3.0 software. Vascular lesion counts were analyzed using the SWIFT_MACTEL method, an adaptation of the method used to measure neovascularization (SWIFT_NV) (Stahl, A., et al. *Angiogenesis* 12, 297-301 (2009) in the oxygen induced retinopathy model.

SWIFT_MACTEL

A set of macros were created that were developed to run on ImageJ platform (National Institutes of Health, http://imagej.nih.gov/ij/). In brief, SWIFT_MACTEL isolates the red channel from a lectin-stained retinal whole mount, divides the image into four quadrants and removes background fluorescence to allow for the neovascularization (NV) structures to stand out clearly against the background fluorescence of normal vessels. Using a slide bar to either increase or decrease a particular quadrant's fluorescence threshold, the SWIFT_MACTEL user designates a threshold that marks NV structures but not normal vessels to each quadrant. After setting the appropriate threshold, artifacts like cellular debris or hyperfluorescent retinal edges can be manually removed and excluded from quantification. SWIFT_MACTEL then analyzes all pixels in the image that lie above the chosen intensity threshold and are part of an object that has a minimum size of 100 pixels. By setting this cut-off in object size, small artifacts like vessel branch points are automatically removed. After measuring all four quadrants, SWIFT_MACTEL creates a composite from all four NV quadrants and calculates the total NV pixel number. Results from the SWIFT_NV method have been found to correlate well with results from the established hand measurement protocols ($R^2$=0.9372) and show robust intra-individual ($R^2$=0.9376) and inter-individual ($R^2$=0.9424) reproducibility (Stahl, A., et al. *Angiogenesis* 12, 297-301 (2009)). n is number of eyes quantified.

Scanning Electron Microscopy and 3D Retinal Reconstruction

Tissue was processed for serial block face scanning electron microscopy (SEM) using an adapted version of a protocol established by Deerinck et al. 2010 (T. Deerinck, et al., Microscopy and Microanalysis 16, no. S2 (2010)). Whole eyes were isolated and fixed in Karnovsky's fixative. The cornea and lens were removed and the tissue further fixed in tannic acid overnight. Heavy metal infiltration was then undertaken; tissue was incubated in 1.5% potassium ferrocyanide, 0.5% osmium tetroxide in cacodylate buffer, followed by thiocarbohydrazide treatment and a second exposure to 1% osmium incubation. Walton's lead aspartate exposure was not carried out, so they were finished with 1% uranyl acetate incubation followed by dehydration to propylene oxide and embedded in Durcupan ACM resin. The tissue was serially sectioned and imaged using the Gatan 3VIEW serial block face imaging system (Gatan, Abingdon, UK) fitted to a Zeiss Sigma variable pressure field emission scanning electron microscope (Zeiss, Cambridge, UK). Data was collected and used in Amira Software (FEI, Oregon, USA) in order to reconstruct the 3D images. Using the same software, photoreceptor mitochondrial volume was estimated for WT mice, around the lesions in Vldlr mice, and away from the lesion in Vldlr$^{-/-}$ mice.

ATP Measurement

ATP was measured using a kit per instruction manual (Molecular Probes, A22066). Briefly, a standard reaction solution was made from the following components: $dH_2O$, 20× Reaction Buffer, DTT (0.1 M), D-luciferin (10 mM), firefly luciferase stock solution (5 mg/mL). Low-concentration ATP standard solutions were prepared by diluting ATP solution (5 mM) in $dH_2O$. A standard curve was generated by subtracting the background luminescence of the standard reaction solution from luminescence readings for a series of dilute ATP standard solutions. Luminescence measurements were taken for ATP-containing samples and the amount of ATP in experimental samples were calculated from the standard curve.

Oxygen Consumption and Extracellular Acidification Rates

All oxygen consumption rates were measured using a Seahorse XFe96 Flux Analyzer®. Whole retinas were isolated and 1 mm punch biopsies were loaded into the 96 well plate. Retinal punches were incubated in assay media (DMEM 5030 media supplemented with 12 mM glucose, 10 mM HEPES and 26 mM $NaHCO_3$) to measure oxygen consumption rates (OCR) and extracellular acidification rates (ECAR). Photoreceptor (661W) cells, were incubated in their assay media (DMEM 5030, 12 mM glucose, 10 mM HEPES) one hour prior to measurements. Fatty acid oxidation rates were determined by treating tissues or cells with Etomoxir (40 µM; Sigma) 40 min prior to analysis and then providing BSA (control) or BSA/Palmitate conjugate (Seahorse). Glucose oxidation rates were measured after injection of 2-deoxyglucose (2-DG, 100 mM; Sigma) or media control during data acquisition. To determine the maximal fatty acid or glucose oxidative capacity, the non-mitochondrial respiration (rate after injection of 2 µM Rotenone and 2 µM Antimycin A) was subtracted from the oxygen consumption rate after injection of 0.5 µM carbonyl cyanide-ptrifluoromethoxyphenylhydrazone (FCCP).

Glucose and Lactate Measurements

Whole retinas and photoreceptors (661W) were incubated in assay media (DMEM 5030, 12 mM glucose, 10 mM HEPES) for 6 and 48 hours respectively. Media was collected, spun briefly (13 g) to remove cellular debris, and glucose and lactate levels measured using a Yellow Springs Instrument (YSI) 2950 were compared to control media that was not exposed to tissue or cells. To determine the conversion of glucose to lactate (the glycolytic rate), lactate production was divided by glucose uptake.

Retinal Lipid Uptake

Retinal long-chain fatty acid uptake was compared for wild type and Vldlr$^{-/-}$ mice gavaged with 0.1 mg of 4,4-difluoro-5,7-dimethyl-4-bora-3a, 4a-diaza-s-indacene-3-hexadecanoic acid (BODIPY FL C16; Molecular Probes). Mice were euthanized 2 h later and the eyes were enucleated, embedded in OCT and cryo-sectioned (10 µm) for immediate imaging by fluorescence microscopy. Retinal FA uptake was quantitated using $^{14}$C-labeled 2-bromopalmitate tracer injected twice daily (i.p.; 0.5 uCi per dose) from P9 to P12; total administered radioactivity was normalized for mouse body weight. Retinas were then dissected and homogenized in Ultima Gold liquid scintillation cocktail (PerkinElmer) and beta-counted ($^{14}$C DPM) using Tri-Carb 2900TR instrument (PerkinElmer), correcting for background scintillation.

Plasma Triglycerides (TG) and Fatty Acid (FA) Analysis

Plasma was isolated from WT and Vldlr$^{-/-}$ mice by centrifugation (2000 g×20 min; 4° C.) of whole blood in EDTA-coated tubes. TGs were determined using the RANDOX TRIGS kit (TR210) per instruction manual. FAs in whole plasma were assayed as described previously (Spahis, S., et al. *Prostaglandins Leukot Essent Fatty Acids* 99, 25-34 (2015)). Briefly, each sample was subjected to direct transesterification and then injected into a gas chromatograph using the Agilent GC AutoSampler system (7890A). FAs were identified by comparison with the expected retention times of known standards and then analyzed with OpenLAB Software Suite (Agilent).

β-Oxidation Metabolite Quantification

Acylcarnitine metabolites were extracted from WT and Vldlr$^{-/-}$ (P12) flash frozen retinas using ice-cold methanol. Samples were sonicated, centrifuged and the supernatant was transferred to a fresh tube for nitrogen evaporation. When dry, butanolysis was performed (butanol-HCl, 55° C.

for 20 min) prior to reconstitution in mobile phase (ACN: H$_2$O 80:20, formic acid 0.05%). Samples were analyzed by liquid chromatography followed by tandem mass spectrophotometry (LC/MS/MS, Alliance 2795 LC and Quattro micro, Waters Corp). Data were recorded in positive electrospray ionization and analyzed with Neolynx (Waters Corp).

Retinal Glucose Uptake

Positron emission tomography (PET) imaging studies were performed on WT, Vldlr$^{-/-}$/Ffar1$^{-/-}$ and Ffar1$^{-/-}$ mice (P16; Focus 120 high-resolution, Siemens), followed by micro CAT imaging (MicroCAT II scanner, Siemens). Fluorine-18 fluorodeoxyglucose FDG) was administered by intraperitoneal injection (i.p.) to obtain nontoxic radioactivity levels (3.7 and 37 MBq; or 0.1 to 1.0 mCi). Actual administered activity was determined using a dose calibrator to measure activity in the syringe before and after the injection. Images were acquired 60 minutes after injection to ensure radiotracer uptake. Mice were fasted for 6 hours prior to imaging, kept in darkness and anesthetized by inhalation of isoflurane (2-4%) through a nose cone for the duration of the procedure. Animals were imaged in a head first, prone position, and placed on a heating pad to maintain appropriate body temperature. Upon completion of imaging, mice were euthanized and retinas were dissected for precise $^{18}$F-FDG retinal activity, quantification by gamma counter, and corrected for decay. WT and Vldlr$^{-/-}$ mice pups were also injected with trace amounts of $^3$H-2-deoxyglucose (0.5 µCi daily, i.p.) and treated with GW9508 or vehicle (14 µM daily, i.p.) for 5 days (P7-P12). Retinas were collected and homogenized in a scintillation cocktail (Ecolite+, MP biomedicals) and betacounts measured using the LS6500 Multipurpose Scintillation Counter (Beckman).

Laser-Capture Microdissection

Eyes were embedded in OCT and flash frozen immediately following enucleation. Eyes were cryosectioned under RNase free conditions into 10 µm sections, and collected on RNase-free polyethylene naphthalate glass slides (Ser. No. 11/505,189, Leica). Sections were stained for lectin (1:50 in 1 mM CaCl$_2$) and dehydrated with 70%, 90% and 100% ethanol washes. Retinal vessels and layers were microdissected with a Leica LMD 6000 system (Leica Microsystems) and collected directly into RNA stabilizing buffer from the RNeasy Micro kit (Qiagen, Chatsworth, Calif.). RNA was extracted from microdissected tissues using the RNeasy Kit as described above (Qiagen), and real-time PCR was performed with the generated cDNA.

Reverse Transcription and Quantitative Real-Time PCR Analysis

RNA samples from cell culture, whole retina or laser-captured neovessels and layers were treated with DNase I (Qiagen, Chatsworth, Calif.) to remove any contaminating genomic DNA. The DNase-treated RNA was then converted into cDNA using reverse transcriptase (Invitrogen). PCR primers for target genes and the control gene, cyclophilin A, were designed using Primer Bank and NCBI Primer Blast software. Quantitative analysis of gene expression was generated using an ABI Prism 7700 Sequence Detection System with the SYBR Green Master mix kit and gene expression was calculated relative to cyclophilin A using the ΔcT method.

Primer sequences

| Gene | Forward (5'-3') | SEQ ID NO: | Reverse (5'-3') | SEQ ID NO: |
|---|---|---|---|---|
| Cpt1a | CATGTCAAGCCAGAGGAAGA | 1 | TGGTAGGAGAGCAGCACCTT | 2 |
| Cyclophillin A | CAGACGCCACTGTCGCTTT | 3 | TGTCTTTGGAACTTTGTCTGCAA | 4 |
| Glut1 | CAGTTCGGCTATAACACTGGTG | 5 | GCCCCCGACAGAGAAGATG | 6 |
| Ffar4 (GPR120) | CTTTCTTCTCGGATGTCAAGGG | 7 | GATGAGCCCCAGAACGGTG | 8 |
| Ffar1 (GPR40) | CCTTCGCTCTCTATGTATCTGCC | 9 | GGCTAACAAGTTCAATGGAAAGC | 10 |
| Ffar3 (GPR41) | TTCTGAGCGTGGCCTATCCA | 11 | AGACTACACTGACCAGACCAG | 12 |
| Ffar2 (GPR43) | TGCTACGAGAACTTCACCCAA | 13 | CACACGAAGCGCCAATAACAG | 14 |
| GPR84 | CCAGCGAGGGGATTTCATCTG | 15 | GCTTCTGACGAATCACCTTCCA | 16 |
| Pkm2 | ATCGGGCGATGCAACCGAGC | 17 | AGAGGGCCATCAAGGTACAGGCA | 18 |
| Ppara | AGAGCCCCATCTGTCCTCTC | 19 | ACTGGTAGTCTGCAAAACCAAA | 20 |
| Pparβ/δ | TCCATCGTCAACAAAGACGG | 21 | ACTTGGGCTCAATGATGTCAC | 22 |
| Pparγ | TCGCTGATGCACTGCCTATG | 23 | GAGAGGTCCACAGAGCTGATT | 24 |

-continued

| Primer sequences | | | | |
|---|---|---|---|---|
| Gene | Forward (5'-3') | SEQ ID NO: | Reverse (5'-3') | SEQ ID NO: |
| VE-Cadherin | ATTGGCCTGTGTTTTCGCAC | 25 | CACAGTGGGGTCATCTGCAT | 26 |
| Vldlr | TCTCTTGCTCTTAGTGATGG | 27 | CTTACAACTGATATTGCTGGG | 28 |

Expression Array

Illumina mouse gene microarray analysis of WT and Vldlr$^{-/-}$ retinas was performed in biological triplicate (Mouse-WG6 expression BeadChip, Illumina). The chip contains 45,000 probe sets representing 34,000 genes. Microarray studies, from cDNA synthesis to raw data normalization were performed by the Molecular Genetics Core Facility at Boston Children's Hospital. Briefly, total RNA (1 µg each) was reverse transcribed, followed by a single in vitro transcription amplification to incorporate biotin-labeled nucleotide, and subsequent hybridization and staining with strepatavidin-Cy3 according to the manufacturer's instructions. The chip was scanned with Illumina BeadArray Reader to measure the signal intensity by the labeled target. Raw data were analyzed with the microarray software (Bead Studio Gene Expression version 3.4.0) for quality control, background analysis and normalization with rank invariant algorithm. Normalized data was further analyzed for comparative molecular and cellular pathway regulation using Ingenuity Pathway Analysis (P=0.05 and delta of 0.19; Quiagen) (Calvano, S. E., et al. Nature 437, 1032-1037 (2005)).

Immunohistochemistry

For whole mount immunohistochemistry, eyes were enucleated and fixed in 4% paraformaldehyde at room temperature for 1 h. The retina was isolated and stained for retinal vasculature and lesions with fluoresceinated Isolectin B$_4$ (Alexa Fluor-594 in PBS with CaCl$_2$ 1 mM, I21413, Molecular Probes) overnight at room temperature (RT). Retinas were visualized using a 5× objective with a Zeiss AxioObserver.Z1 microscope, and imaged with a Zeiss AxioCam MRm operated by AxioVision software (version 4.6.3.0). Whole mounts were also fixed and permeabilized in cold methanol (20 min at −20° C.), blocked in 3% bovine serum albumin and 0.1% Triton X-100, stained with Isolectin B$_4$ to visualize vessels (as above) and/or with primary antibodies against HIF1α (1:100 in TBS, NB00-134, Novus), VEGF (1:100, RB-222, Thermo Scientific), IBA-1 (1:200, CP290A, Biocare Medical UK) and blue opsin cone (1:100, sc-14365, Santa Cruz) overnight at 4° C., followed by secondary antibody staining (1 hour at RT; AlexaFluor 1:1000, Invitrogen). Flatmounts (and cross-section) were imaged with confocal microscopy (Leica TCS SP2 AOBS) and z-stacks were 3D reconstructed using Volocity software (Perk Elmer).

Western Blot and ELISA

Retinal samples were obtained as described above. Retinal lysate (20 µg) from three different animals or endothelial cells lysate (10 µg) were loaded on an SDS-PAGE gel and electroblotted onto a PVDF membrane. After blocking, the membranes were incubated with antibodies against β-Actin (Sigma, A1978), Hif1α (Novus, NB100-134), and Glut1 (Novus, NB300-666 and Abcam, Ab652) overnight (1:1000 each). After washing, membranes were incubated with 1:10,000 horseradish peroxidase-conjugated anti-rabbit or anti-mouse secondary antibodies (Amersham, NA931V and NA934V) for one hour at room temperature. Densitometry was analyzed using ImageJ. Retinal Vegfa concentration was measured by ELISA (as per manual, MMV00, R&D Systems) and normalized by doing a Bradford to measure the total cell protein content of each samples.

Metabolite Profiling

Metabolites of rapidly dissected WT and Vldlr$^{-/-}$ retinas (flash frozen less than a minute from euthanasia; 15-16 biological replicates) were homogenized in 80% methanol (8 µL/mg of tissue) containing the internal standards inosine-$^{15}$N$_4$, thymine-d$_4$, and glycocholate-d$_4$ (Cambridge Isotope Laboratories) using a TissueLyser II (Qiagen) bead mill for 4 minutes at 20 Hz. Samples were centrifuged (9,000 g, 10 min, 4° C.) to pellet debris and supernatants were analyzed using two liquid chromatography tandem mass spectrometry (LC-MS) methods to measure polar metabolites as described previously (Jain, M., et al. Science 336, 1040-1044 (2012), and Townsend, M. K., et al. Clin Chem 59, 1657-1667 (2013). Briefly, negative ionization mode multiple reaction mode (MRM) data were acquired using an ACQUITY UPLC (Waters) coupled to a 5500 QTRAP triple quadrupole mass spectrometer (AB SCIEX). The supernatants were injected directly onto a 150×2.0 mm Luna NH$_2$ column (Phenomenex) that was eluted at a flow rate of 400 µL/min with initial conditions of 10% mobile phase A [20 mM ammonium acetate and 20 mM ammonium hydroxide (Sigma-Aldrich) in water (VWR)] and 90% mobile phase B [10 mM ammonium hydroxide in 75:25 v/v acetonitrile/methanol (VWR)] followed by a 10 min linear gradient to 100% mobile phase A. The ion spray voltage was −4.5 kV and the source temperature was 500° C. Positive ionization mode MRM data were acquired using a 4000 QTRAP triple quadrupole mass spectrometer (AB SCIEX) coupled to an 1100 Series pump (Agilent) and an HTS PAL autosampler (Leap Technologies). Cell extracts (10 µL) were diluted using 40 µL of 74.9:24.9:0.2 (v/v/v) acetonitrile/methanol/formic acids containing stable isotope-labeled internal standards [0.2 ng/µL valine-d8, Isotec; and 0.2 ng/µL phenylalanine-d8 (Cambridge Isotope Laboratories)] and were injected onto a 150×2.1 mm Atlantis HILIC column (Waters). The column was eluted isocratically at a flow rate of 250 µL/min with 5% mobile phase A (10 mM ammonium formate and 0.1% formic acid in water) for 1 minute followed by a linear gradient to 40% mobile phase B (acetonitrile with 0.1% formic acid) over 10 minutes. The ion spray voltage was 4.5 kV and the source temperature was 450° C. Raw data were processed using MultiQuant 2.1 (AB SCIEX) for automated peak integration and metabolite peaks were manually reviewed for quality of integration and compared against known standards to confirm identity.

Photoreceptor (661W) Cell Culture

Cone photoreceptor cells (al-Ubaidi, M. R., *J Cell Biol* 119, 1681-1687 (1992), and Tan, E., et al. *Invest Ophthalmol Vis Sci* 45, 764-768 (2004)) (661W; from Dr. Al-Ubaidi) were cultured as monolayers at 37° C., 5% $CO_2$ in a humidified atmosphere in DMEM with FBS 10% supplemented with hydrocortisone (20 μg/500 mL, H-2270, Sigma), Progesterone (20 μg/500 mL, P-8783, Sigma), Putrescine (0.016 g/500 mL, P-7505, Sigma) and β-mercaptoethanol (20 μL/500 mL, M-6250, Sigma). Equal number of 661W cells (0.3×106) were plated in 6-well dishes and cultured to 80% confluence. Cells were washed twice with PBS, starved for 4 hours (above medium without FBS) then stimulated with GW9508 (14 NM, Cayman) or vehicle. Photoreceptors were then collected 8 hours post-treatment for Hif1α protein expression (see Western blot); while their medium was collected at 12 hours for Vegfa quantification by ELISA (as per manual, MMV00, R&D Systems). Vegfa concentration was normalized for the number of cells per well, by doing a Bradford to measure the total cell protein content of each well.

Preparation of AAV2-RKshVldlr Vector and AAV2 Virus

Three independent shRNAs against mouse Vldlr were designed using a published algorithm (Park, Y. K., et al. *Nucleic acids research* 36, W97-103 (2008)). Three independent shRNAs against mouse Vldlr were designed using a published algorithm (Park, Y. K., et al. Nucleic acids research 36, W97-103 (2008)). The template oligonucleotides contained miR-30 microRNA, miR-30 loop and Vldlr shRNA including the sense and the antisense were synthesized (Invitrogen). DNA fragments were amplified, purified, digested and inserted into modified CAG-GFP-miR30 vector (provided by Dr. Zhiqiang Lin and Dr. William T. Pu at Boston Children's Hospital) according to a previous report (Grieger, J. C., et al., Nature protocols 1, 1412-1428 (2006)) and CAG promoter was replaced with rhodopsin kinase (RK) promoter (Khani, S. C., et al. Investigative ophthalmology & visual science 48, 3954-3961 (2007)) that was cloned from pAAVRK-GFP (provided by Dr. Connie Cepko and Dr. Tiansen Li). The Vldlr knock down efficiency was tested in pup retinas. Recombinant AAV2 vectors were produced as previously described (Vandenberghe, L. H., et al. Human gene therapy 21, 1251-1257 (2010)). Briefly, AAV vector, rep/cap packaging plasmid, and adenoviral helper plasmid were mixed with polyethylenimine and transfected into HEK293T cells (CRL-11268, ATCC). Seventy-two hours after transfection, cells were harvested and the cell pellet was resuspended in virus buffer, followed by 3 cycles of freeze-thaw, and homogenized. Cell debris was pelleted at 5,000 g for 20 minutes, and the supernatant was run on an iodixanol gradient. Recovered AAV vectors were washed 3 times with PBS using Amicon 100K columns (EMD Millipore). Real-time PCR was used to determine genome titers of the recombinant AAV. This protocol also was used to prepare a control AAV2-shControl. Viruses were diluted to various concentrations to test infection, and a concentration of approximately 2×1012 gc/mL was used for the experiments. The sequences of the mouse Vldlr siRNAs are as follows: shVldlr #1 (5'-3'), GGA AAG TTC AAG TGC AGA AGC G (SEQ ID NO: 29); shVldlr #2 (5'-3'), GGA ATG CCA TAT CAA CGA ATG C (SEQ ID NO: 30); shVldlr #3 (5'-3'), GGG ATC TGC AGT CAA ATT TGT A (SEQ ID NO: 31); Scramble shRNA control (5'-3'), GAT TTA AGA CAA GCG TAT AAC A (SEQ ID NO: 32).

Human Samples and Vitrectomy

The study conforms to the tenets of the Declaration of Helsinki, and approval of the human clinical protocol and informed consent were obtained from the Maisonneuve-Rosemont Hospital (HMR) ethics committee (Ref. CER: 10059). All patients previously diagnosed with AMD were followed and surgery was performed by a single vitreoretinal surgeon (F.A.R.). Vitreous samples were frozen on dry ice immediately after biopsy and stored (−80° C.). VEGFA ELISAs were performed according to manufacturer's instructions (DVE00, R&D Systems).

Statistical Analysis

A Student's t-test was used, and ANOVA with Dunnet, Bonferroni or Tukey post-hoc analysis (see Table 1), to compare different groups; p<0.05 was considered statistically different. D'Agostino-Pearson or Kolmogorov-Smirnov (KS) normality test were used to confirm normal distribution. Data with non-Gaussian distribution was analyzed using a Mann Whitney test (non-parametric, two groups). Animals were not randomized but quantifications were blinded when possible. All experiments were repeated at least 3 times. Values more than 2 standard deviations from the mean were considered outliers and were excluded. Sample size was estimated to detect a difference of 20% with a power of 80% (1-β) and α of 0.05 in accordance with the 'Guidelines for the Use of Animals in Neuroscience' (2003). Results are presented as mean±SEM. * P<0.05,  P<0.01, * P<0.001.

Description of Statistical Analysis

Detailed description of n, difference in variance, statistical test and P values for each figure panel (Table 1):

| FIGURE & PANEL | | Groups | n | Difference in Variance (F test, P value) | Statistical Test | P value |
|---|---|---|---|---|---|---|
| FIG. 1 | a | | | | Schematic | |
| | b | | 5 retinas/time point | | Descriptive | |
| | c | Control (Dark/Light) Dark | 28 retinas 10 retinas | F = 2.848, P = 0.1034 | Unpaired two-tailed Student t-test | 0.0031 |
| | d | WT Vldlr−/− | 23 photoreceptors 23 photoreceptors | F =, 21.91 P < 0.0001 | Unpaired two-tailed Student t-test with Welch's correction | <0.0001 |
| | e | WT Vldlr−/− | 4 retinas (littermate) 6 retinas (littermate) | F = 3.032, P = 0.2635 | Unpaired two-tailed Student t-test | 0.0026 |
| FIG. 2 | a, b | Ctl (BSA) Palmitate Ctl + Etomoxir Palmitate + Etomoxir | 7 retinas 6 retinas 7 retinas 8 retinas | One-way ANOVA, F = 9.783 P = 0.0002 | Tukey's Multiple Comparison Test | Ctl(BSA) vs Palmitate: <0.01 Palmitate vs BSA + Eto: <0.001 Palmitate vs Palm + Eto: <0.01 |

-continued

| FIGURE & PANEL | | Groups | n | Difference in Variance (F test, P value) | Statistical Test | P value |
|---|---|---|---|---|---|---|
| | c | WT<br>Vldlr$^{-/-}$ | 7 plasmas (from 2 animals each)<br>13 plasmas (from 2 animals each) | F = 22.56, P = 0.0011 | Unpaired two-tailed Student t-test with Welch's correction | <0.0001 |
| | d | WT<br>Vldlr$^{-/-}$ | 3 animals (× 2 pooled retinas) per group (littermate) | | β-Oxidation Metabolite Array | |
| | e left | WT<br>Vldlr$^{-/-}$ | 3 animals (× 2 pooled retinas) per group | F = 2.802, P = 0.5260 | Unpaired two-tailed Student t-test | 0.0108 |
| | e right | WT<br>Vldlr$^{-/-}$ | 3 animals (× 2 pooled retinas) per group (littermate) | F = 1.798, P = 0.7147 | Unpaired two-tailed Student t-test | 0.0014 |
| | f left | WT<br>Vldlr$^{-/-}$ | 3 animals (× 2 pooled retinas) per group (littermate) | F = 1.079, P = 0.9620 | Unpaired two-tailed Student t-test | 0.0052 |
| | f right | WT<br>Vldlr$^{-/-}$ | 3 animals (× 2 pooled retinas) per group (littermate) | One-way ANOVA, F = 15.09 P < 0.0001 | Tukey's Multiple Comparison Test | ONL WT vs Vldlr$^{-/-}$: <0.001 |
| | g | WT<br>Vldlr$^{-/-}$ | 22 retinas<br>12 retinas | F = 1.225, P = 0.7492 | Unpaired two-tailed Student t-test | 0.0116 |
| | h left | WT<br>Vldlr$^{-/-}$ | 9 retinas<br>12 retinas | F = 11.61, P = 0.0005 | Unpaired two-tailed Student t-test with Welch's correction | 0.0119 |
| | h right | WT<br>Vldlr$^{-/-}$ | 3 animals (6 retinas)/ group Littermate controlled | One-way ANOVA, F = 60.63, P < 0.0001 | Tukey's Multiple Comparison Test | ONL - WT vs Vldlr$^{-/-}$: <0.001<br>INL - WT vs Vldlr$^{-/-}$: <0.001 |
| | i | WT<br>Vldlr$^{-/-}$ | 6 retinas<br>6 retinas | F = 1.496, P = 0.6691 | Unpaired two-tailed Student t-test | 0.0300 |
| FIG. 3 | a | | | | Schematic | |
| | b | WT<br>Vldlr$^{-/-}$ | 3 animals (6 retinas)<br>3 animals (6 retinas) | One way ANOVA F = 91.38, P < 0.0001<br>One way ANOVA F = 816.5, P < 0.0001 | Dunnett's Multiple Comparison Test | Ffar1 vs all other Ffar: <0.001 |
| | c | WT<br>Vldlr$^{-/-}$ | 3 animals (6 retinas)<br>3 animals (6 retinas) | One-way ANOVA, F = 209.5, P < 0.0001<br>One-way ANOVA, F = 82.14, P < 0.0001 | Dunnett's Multiple Comparison Test | ONL vs other layers: <0.001 |
| | d WT | Ctl<br>GW | 5 retinas<br>8 retinas | One-way ANOVA, F = 20.03, P < 0.0001 | Tukey's Multiple Comparison Test | WT-Ctl vs WT-GW: <0.001<br>WT-Ctl vs Vldlr$^{-/-}$-Ctl: <0.01<br>WT-Ctl vs Vldlr$^{-/-}$-GW: <0.001<br>Vldlr$^{-/-}$-Ctl vs Vldlr$^{-/-}$-GW: <0.01 |
| | d Vldlr$^{-/-}$ | Ctl<br>GW | 9 retinas<br>16 retinas | | | |
| | e | Ctl<br>GW | 12 retinas<br>12 retinas | F = 5.570, P = 0.0083 | Unpaired two-tailed Student t-test with Welch's correction | <0.0001 |
| | f | Ctl<br>GW | 7 retinas<br>11 retinas | F = 4.719, P = 0.0708 | Unpaired two-tailed Student t-test | 0.0002 |
| | g | WT<br>Vldlr$^{-/-}$<br>Vldlr$^{-/-}$/Ffar1$^{-/-}$ | 4 retinas<br>4 retinas<br>4 retinas | One-way ANOVA, F = 11.75, P = 0.0031 | Dunnett's Multiple Comparison Test | Vldlr$^{-/-}$ vs other groups: <0.05 |
| | h | WT<br>Vldlr$^{-/-}$<br>Vldlr$^{-/-}$/Ffar1$^{-/-}$ | 10 retinas<br>9 retinas<br>9 retinas | One-way ANOVA, F = 4.89, P = 0.0161 | Dunnett's Multiple Comparison Test | Vldlr$^{-/-}$ vs other groups: <0.05 |
| | i | Vldlr$^{-/-}$<br>Vldlr$^{-/-}$/Ffar1$^{-/-}$ | 10 retinas<br>10 retinas | F = 1.075, P = 0.9159 | Unpaired two-tailed Student t-test | 0.0153 |

| FIGURE & PANEL | | Groups | n | Difference in Variance (F test, P value) | Statistical Test | P value |
|---|---|---|---|---|---|---|
| FIG. 4 | a | | | | Schematic | |
| | b | WT | 15 animals (12 × 2 pooled retinas) | non Gaussian distribution | two-tailed Mann Whitney test | 0.0032 |
| | | Vldlr$^{-/-}$ | 12 animals (15 × 2 pooled retinas) | | | |
| | c | WT | 3 animals (2 pooled retinas) | F = 2.362, P = 0.5949 | Unpaired two-tailed Student t-test | 0.0094 |
| | | Vldlr$^{-/-}$ | 3 animals (2 pooled retinas) | | | |
| | d | WT | 11 animals (12 × 2 pooled retinas) | F = 2.622, P = 0.0974 | Unpaired two-tailed Student t-test | 0.0069 |
| | | Vldlr$^{-/-}$ | 15 animals (15 × 2 pooled retinas) | | | |
| | e | WT | 15 animals (12 × 2 pooled retinas) | non Gaussian distribution | two-tailed Mann Whitney test | 0.0004 |
| | | Vldlr$^{-/-}$ | 12 animals (15 × 2 pooled retinas) | | | |
| | f | WT | 3 retinas | One-way ANOVA, F = 4.87, P = 0.0554 | Dunnett's Multiple Comparison Test | WT vs Vldlr$^{-/-}$: <0.05 |
| | | Vldlr$^{-/-}$ | 3 retinas | | | |
| | | Vldlr$^{-/-}$/Ffar1$^{-/-}$ | 3 retinas | | | |
| | g | Vldlr$^{-/-}$ | 3 retinas | | descriptive | |
| | h | WT | 6 retinas | One-way ANOVA, F = 21.68, P < 0.0001 | Tukey's Multiple Comparison Test | WT vs Vldlr$^{-/-}$: <0.001 Vldlr$^{-/-}$ vs Vldlr$^{-/-}$/Ffar$^{-/-}$: <0.01 |
| | | Vldlr$^{-/-}$ | 6 retinas | | | |
| | | Vldlr$^{-/-}$/Ffar1$^{-/-}$ | 6 retinas | | | |
| | i | | 3 retinas | | descriptive | |
| | j | Ctl | 8 vitreous samples | One-way ANOVA, F = 4.972, P = 0.0221 | Dunnett's Multiple Comparison Test | Ctl vs other groups: <0.05 |
| | | CNV | 7 vitreous samples | | | |
| | | RAP | 3 vitreous samples | | | |
| FIG. 5 | a | WT | 4 retinas | One-way ANOVA, F = 44.01, P < 0.0001 | Dunnett's Multiple Comparison Test | WT vs Vldlr$^{+/-}$: <0.01 WT vs Vldlr$^{-/-}$: <0.001 Vldlr$^{+/-}$ vs Vldlr$^{-/-}$: <0.01 |
| | | Vldlr$^{+/-}$ (het) | 5 retinas | | | |
| | | Vldlr$^{-/-}$ | 5 retinas | | | |
| | b | WT | 7 plasmas (2 pooled mice each) | F = 6.855, P = 0.0229 | Unpaired two-tailed Student t-test with Welch's correction | 0.5596 (n.s.) |
| | | Vldlr$^{+/-}$ (het) | 8 plasmas (2 pooled mice each) | | | |
| | c | WT | 7 plasmas (2 pooled mice each) | F = 3.398, P = 0.1346 | Unpaired two-tailed Student t-test | 0.6969 (n.s.) |
| | | Vldlr$^{+/-}$ (het) | 8 plasmas (2 pooled mice each) | | | |
| | d, e | | | | Schematics | |
| | f, g | | 5 retinas/time point | | Descriptive | |
| | h | shCtl | 8 retinas | One-way ANOVA, F = 7.227, P = 0.0010 | Dunnett's Multiple Comparison Test | shCtl vs shVldlr 1: <0.05 shCtl vs shVldlr 2: <0.01 shCtl vs shVldlr 3: <0.001 |
| | | shRNA Vldlr - 1 | 12 retinas | | | |
| | | shRNA Vldlr - 2 | 4 retinas | | | |
| | | shRNA Vldlr - 3 | 8 retinas | | | |
| | i | | 5 retinas/time point | | Descriptive | |
| FIG. 6 | a | | | | Schematic | |
| | b, c | Palmitate | 6 retinas | non Gaussian distribution | two-tailed Mann Whitney test | 0.0027 |
| | | Palmitae + Etomoxir | 8 retinas | | | |
| | d, e | Glucose | 8 retinas | F = 1.512, P = 0.5989 | Unpaired two-tailed Student t-test | 0.0019 |
| | | Glucose + 2-DG | 8 retinas | | | |
| | f | Glucose | 8 retinas | non Gaussian distribution | two-tailed Mann Whitney test | 0.8518 (n.s.) |
| | | Palmitate | 6 retinas | | | |
| | g | Glucose | 4 retinas | | descriptive | |
| | | Lactate | 4 retinas | | | |
| | h left | WT - Ctl | 15 retinas | F = 3.632, P = 0.0229 | Unpaired two-tailed Student t-test with Welch's correction | 0.0035 |
| | | WT - Palmitate | 14 retinas | | | |
| | h right | Vldlr$^{-/-}$ - Ctl | 10 retinas | F = 1.345, P = 0.6194 | Unpaired two-tailed Student t-test | 0.5758 (n.s.) |
| | | Vldlr$^{-/-}$- Palmitate | 13 retinas | | | |
| FIG. 7 | a | WT | 3 retinas | One-way ANOVA, F = 130.6, P < 0.0001 | Tukey's Multiple Comparison Test | ONL vs all layers: <0.001 RPE vs GC layer: <0.05 |

-continued

| FIGURE & PANEL | | Groups | n | Difference in Variance (F test, P value) | Statistical Test | P value |
|---|---|---|---|---|---|---|
| | b | WT<br>Vldlr−/− | 3 retinas<br>3 retinas | | descriptive | |
| | c | WT<br>Vldlr−/− | 16 retinas<br>12 retinas | F = 1.051, P = 0.9540 | Unpaired two-tailed Student t-test | 0.0003 |
| | d | WT<br>Vldlr−/− | 7 plasmas (2 pooled mice each)<br>13 plasmas (2 pooled mice each) | F = 10.37, P = 0.0092 | Unpaired two-tailed Student t-test with Welch's correction | <0.0001 |
| | e<br>C8 | WT<br>Vldlr−/− | 7 plasmas (2 pooled mice each)<br>13 plasmas (2 pooled mice each) | non Gaussian distribution | two-tailed Mann Whitney test | 0.1322 |
| | C10 | WT<br>Vldlr−/− | 7 plasma (2 pooled mice each)<br>13 plasmas (2 pooled mice each) | non Gaussian distribution | two-tailed Mann Whitney test | 0.0012 |
| | C12 | WT<br>Vldlr−/− | 7 plasmas (2 pooled mice each)<br>13 plasmas (2 pooled mice each) | F = 7.974, P = 0.0184 | Unpaired two-tailed Student t-test with Welch's correction | <0.0001 |
| | C14 | WT<br>Vldlr−/− | 7 plasmas (2 pooled mice each)<br>13 plasmas (2 pooled mice each) | F = 12.71, P = 0.0053 | Unpaired two-tailed Student t-test with Welch's correction | <0.0001 |
| | C16 | WT<br>Vldlr−/− | 7 plasmas (2 pooled mice each)<br>13 plasmas (2 pooled mice each) | F = 22.56, P = 0.0011 | Unpaired two-tailed Student t-test with Welch's correction | <0.0001 |
| | C18 | WT<br>Vldlr−/− | 7 plasmas (2 pooled mice each)<br>13 plasmas (2 pooled mice each) | F = 25.57, P = 0.0007 | Unpaired two-tailed Student t-test with Welch's correction | <0.0001 |
| | C18:1n9 | WT<br>Vldlr−/− | 7 plasmas (2 pooled mice each)<br>13 plasmas (2 pooled mice each) | F = 12.89, P = 0.0051 | Unpaired two-tailed Student t-test with Welch's correction | <0.0001 |
| | C18:2n6 | WT<br>Vldlr−/− | 7 plasmas (2 pooled mice each)<br>13 plasmas (2 pooled mice each) | F = 23.96, P = 0.0009 | Unpaired two-tailed Student t-test with Welch's correction | <0.0001 |
| | C20:4n6 | WT<br>Vldlr−/− | 7 plasmas (2 pooled mice each)<br>13 plasmas (2 pooled mice each) | F = 13.54, P = 0.0044 | Unpaired two-tailed Student t-test with Welch's correction | <0.0001 |
| | C22:6n3 | WT<br>Vldlr−/− | 7 plasmas (2 pooled mice each)<br>13 plasmas (2 pooled mice each) | F = 5.334, P = 0.0507 | Unpaired two-tailed Student t-test | <0.0001 |
| FIG. 8 | a | WT<br>Vldlr−/− | 3 animals (× 2 pooled retinas) per group (littermate) | F = 427.2, P = 0.0047 | Unpaired two-tailed Student t-test with Welch's correction | 0.0079 |
| | b | WT<br>Vldlr−/− | 3 animals (× 2 pooled retinas) per group (littermate) | One-way ANOVA, F = 19.02, P < 0.0001 | Tukey's Multiple Comparison Test | WT ONL vs all other layers: <0.001 |
| | c | Ctl<br>WY16463 | 10 retinas<br>12 retinas | F = 2.2, P = 0.218 | Unpaired two-tailed Student t-test | 0.0429 |
| FIG. 9 | a, b | Veh - Ctl<br>Veh - Palmitate<br>Etomoxir - Ctl<br>Etomoxir - Palmitate | 5 retinas<br>5 retinas<br>6 retinas<br>6 retinas | One-way ANOVA, F = 55.54, P < 0.0001 | Tukey's Multiple Comparison Test | Ctl + Veh vs Palmitate + veh: <0.001<br>Palmitate + Veh vs Ctl or Palm + Eto: <0.001 |
| | c, d | Veh - Ctl<br>Veh - Palmitate<br>PPARa agonist - Ctl<br>PPARa + Palmitate | 5 retinas<br>5 retinas<br>6 retinas<br>5 retinas | One-way ANOVA, F = 89.67, P < 0.0001 | Tukey's Multiple Comparison Test | Ctl + Veh vs Palmitate + veh: <0.001<br>Palmitate + PPARa agonist vs all groups: <0.001 |

| FIGURE & PANEL | | Groups | n | Difference in Variance (F test, P value) | Statistical Test | P value |
|---|---|---|---|---|---|---|
| | e, f | Veh - Ctl | 5 retinas | | | |
| | | Veh - Palmitate | 6 retinas | non Gaussian distribution | Kruskal-Wallis with Dunn's Multiple Comparison Test | n.s. |
| | | PPARa - Ctl | 6 retinas | | | |
| | | PPARa + Palmitate | 4 retinas | | | |
| FIG. 10 | a | WT | 3 animals (× 2 pooled retinas) per group (littermate) | | Ingenuity array pathway analysis | |
| | | Vldlr$^{-/-}$ | | | | |
| | b | WT | 6 retinas | F = 52.4, P = 0.0019 | Unpaired two-tailed Student t-test with Welch's correction | 0.0215 |
| | | Vldlr$^{-/-}$ | 5 retinas | | | |
| | c | WT | 4 retinas | F = 1.262, P = 0.8006 | Unpaired two-tailed Student t-test | 0.8403 (n.s.) |
| | | Vldlr$^{-/-}$ | 3 retinas | | | |
| | | WT | 4 retinas | F = 5.733, P = 0.1889 | Unpaired two-tailed Student t-test | 0.4517 (n.s.) |
| | | Vldlr$^{-/-}$ | 3 retinas | | | |
| FIG. 11 | a | WT - Ctl | 11 retinas | F = 3.055, P = 0.0927 | Unpaired two-tailed Student t-test | 0.0284 |
| | | WT - GW | 11 retinas | | | |
| | | Vldlr$^{-/-}$ - Ctl | 16 retinas | F = 1.430, P = 0.5031 | Unpaired two-tailed Student t-test | 0.0142 |
| | | Vldlr$^{-/-}$ - GW | 14 retinas | | | |
| | b | WT | 17 retinas | | | |
| | | Vldlr$^{-/-}$ | 6 retinas | One-way ANOVA, F = 6.613, P < 0.0008 | Dunnett's Multiple Comparison Test | WT vs Vldlr$^{-/-}$: <0.001 |
| | | Vldlr$^{-/-}$/Ffar1$^{-/-}$ | 10 retinas | | | |
| | | Ffar1$^{-/-}$ | 16 retinas | | | |
| | c | WT | 9 retinas | | | |
| | | Vldlr$^{-/-}$ | 9 retinas | One-way ANOVA, F = 4.762, P < 0.01 | Dunnett's Multiple Comparison Test | WT vs Vldlr$^{-/-}$: <0.01 |
| | | Vldlr$^{-/-}$/Ffar1$^{-/-}$ | 6 retinas | | | |
| | | Ffar1$^{-/-}$ | 3 retinas | | | |
| | d | siNT | 3 experiments | F = 12.4, P = 0.1493 | Unpaired two-tailed Student t-test | 0.0025 |
| | | siFfar1 | | | | |
| | e | siNT - Ctl | 3 experiments | One-way ANOVA, | Bonferroni's Multiple Comparison | <0.001 |
| | | siNT - GW | | F = 38.99, P < 0.0001 | | |
| | | siFfar1 - Ctl | 3 experiments | | Bonferroni's Multiple Comparison | ns |
| | | siFfar1 - GW | | | | |
| | f | Ctl | 3 retinas | F = 2.438, P = 0.5818 | Unpaired two-tailed Student t-test | 0.0056 |
| | | GW | 3 retinas | | | |
| | | PD - Ctl | 7 retinas | F = 1.691, P = 0.5345 | Unpaired two-tailed Student t-test | 0.1242 (n.s.) |
| | | PD - GW | 4 retinas | | | |
| | | SP - Ctl | 4 retinas | non Gaussian distribution | two-tailed Mann Whitney test | 0.0121 |
| | | SP - GW | 7 retinas | | | |
| FIG. 12 | a | Ctl | 15 retinas | F = 5.546, P = 0.0047 | Unpaired two-tailed Student t-test with Welch's correction | 0.0011 |
| | | MCT | 10 retinas | | | |
| | b | Ctl | 6 retinas | F = 11.79, P = 0.017 | Unpaired two-tailed Student t-test with Welch's correction | 0.0231 |
| | | MCT | 6 retinas | | | |
| | c | Ctl | 9 retinas | F = 1.807, P = 4504 | Unpaired two-tailed Student t-test | 0.0035 |
| | | TAK-875 | 8 retinas | | | |
| FIG. 13 | a | WT - Ctl | 6 retinas | F = 1.189, P = 0.8541 | Unpaired two-tailed Student t-test | 0.0044 |
| | | WT - GW | 6 retinas | | | |
| | b | Vldlr$^{-/-}$ - Ctl | 6 retinas | non Gaussian distribution | two-tailed Mann Whitney test | 0.0411 |
| | | Vldlr$^{-/-}$ - GW | 6 retinas | | | |
| | c | Ctl | 3 experiments | F = 6.193, P = 0.2781 | Unpaired two-tailed Student t-test | 0.0006 |
| | | GW | 3 experiments | | | |
| | d | Complete media | 3 experiments | Two-way ANOVA | Bonferonni post-tests | Complete vs No glucose: <0.01 |
| | | No glucose | 3 experiments | | | |
| | e | Ctl | 3 experiments | F = 3.435, P = 0.4510 | Unpaired two-tailed Student t-test | 0.0013 |
| | | GW | 3 experiments | | | |
| FIG. 14 | a | WT | 13 retina | non Gaussian distribution | Kruskal-Wallis with Dunn's Multiple Comparison Test | 0.0841 (n.s.) |
| | | Vldlr$^{-/-}$ | 8 retinas | | | |
| | | Vldlr$^{-/-}$ + Dark | 7 retinas | | | |
| | | Vldlr$^{-/-}$/Ffar1$^{-/-}$ | 9 retinas | | | |

-continued

| FIGURE & PANEL | Groups | n | Difference in Variance (F test, P value) | Statistical Test | P value |
|---|---|---|---|---|---|
| b | WT<br>Vldlr$^{-/-}$<br>Vldlr$^{-/-}$ + Dark<br>Vldlr$^{-/-}$/<br>Ffar1$^{-/-}$ | 7 retinas<br>8 retinas<br>9 retinas<br>8 retinas | non Gaussian distribution | Kruskal-Wallis with Dunn's Multiple Comparison Test | 0.6177 (n.s.) |
| c, d, e | | 5 retinas/time point | | Descriptive | |

RAP-Like Lesions and Retinal Energy Demand

The number of RAP-like lesions was linked to photoreceptor energy demand. Rod photoreceptors consume 3-4 times more energy in darkness than in light to maintain an electrochemical gradient required for photon-induced depolarization known as the 'dark current' (Okawa, H., et al., *Curr Biol* 18, 1917-1921 (2008)). Conversely, membrane turnover and visual cycle activity are decreased in darkness (Okawa, H., et al., *Curr Biol* 18, 1917-1921 (2008)). Dark-raised Vldlr$^{-/-}$ mice developed 1.5 fold more vascular lesions than those raised in normal light/dark cycles (FIG. 1B), indicating that energy metabolism influenced neovascular disease. Photoreceptors have been described to mature from the optic nerve outward towards the periphery. Energy consumption increases as photoreceptors mature (P12-16), and at P16 the more mature central retina possessed more RAP-like lesions (Wong-Riley, M. T. T. *Eye Brain* 2, 99-116 (2010), and Trick, G. L. & Berkowitz, B. A. *Prog Retin Eye Res* 24, 259-274 (2005)).

To determine whether Vldlr loss specifically in photoreceptors was sufficient to drive pathological vessels, remaining Vldlr was selectively knocked down in photoreceptors (using AAV2-hRK) of Vldlr$^{+/-}$ mice that possessed normal circulating fatty acid levels (Furukawa, et al., *Cell* 91, 531-541 (1997)) (FIGS. 5A-5I). Consistent with energy deficiency, Vldlr$^{-/-}$ photoreceptors exhibited swollen mitochondria (3D scanning electron microscopy and FIG. 1D; videos—not shown). Such results were further confirmed in videos (data not shown), which compared WT and Vldlr$^{-/-}$ photoreceptor mitochondria, where pseudo-colored mitochondria in WT or in Vldlr$^{-/-}$ photoreceptors were visualized by 3D reconstruction of scanning electron microscopy. In Vldlr$^{-/-}$ mice, a vascular lesion was also detected. Moreover, Vldlr$^{-/-}$ retinas had lower ATP stores, (FIG. 1E), which confirmed an energy deficit in the Vldlr$^{-/-}$ mice.

Example 3: Fatty Acids Contributed to Retinal Energy Production in Addition to Glucose and were Likely Also Deficient in Retinas To explore the etiology of energy deficit fostering neovascularization, the contribution of FA and glucose to WT retinal energy production (FIG. 6A) was examined. The long-chain FA palmitate fueled mitochondrial β-oxidation in retinal explants, doubling oxygen consumption rates (OCR). Etomoxir-induced inhibition of FA transport into mitochondria abrogated mitochondrial respiration, confirming that FA β-oxidation contributes to retinal energy metabolism (FIGS. 2A-2B, and 6A-6C).

The contribution of glucose oxidation was further examined, and retinal glucose was also oxidized by mitochondria as efficiently as FA (FIGS. 6D-6F). However, as reported by Warburg, Cohen and Winkler (Cohen, L. H. & Noell, W. K. *J Neurochem* 5, 253-276 (1960), and Winkler, B. S. *J Gen Physiol* 77, 667-692 (1981)), the vast majority of glucose (87%) was converted to lactate by glycolysis rather than oxidative phosphorylation (FIG. 6G). Unlike WT retinas, Vldlr$^{-/-}$ retinas (with limited FA uptake) did not increase mitochondrial respiration when exposed to palmitate (FIG. 6H). FA, in addition to glucose, contributed to retinal energy production, and may also be deficient in Vldlr$^{-/-}$ retinas.

Quantification of Fatty Acid Uptake

Figure 2A:
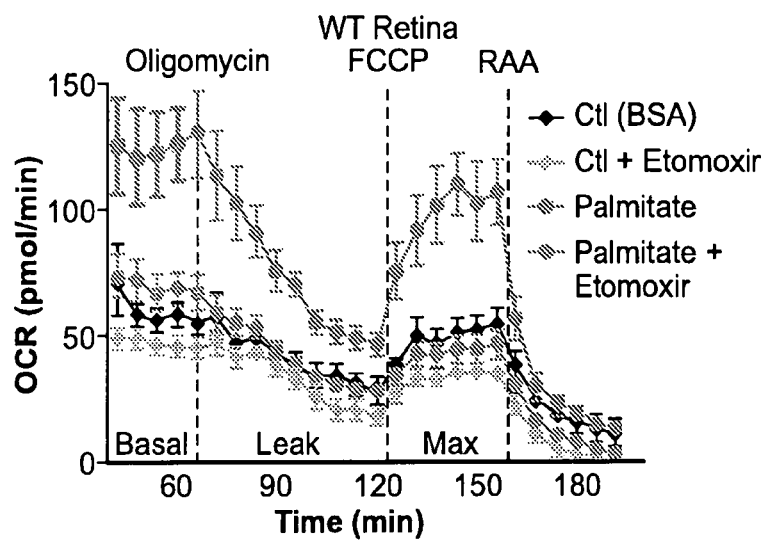
FIG. 2A depicts a graph showing oxygen consumption rate (OCR) of wild type (WT) retinas provided with long-chain fatty acid (FA) palmitate in the presence or absence of FA oxidation inhibitor, etomoxir (40 μM); n=6-8 retinas
Figure 2B:
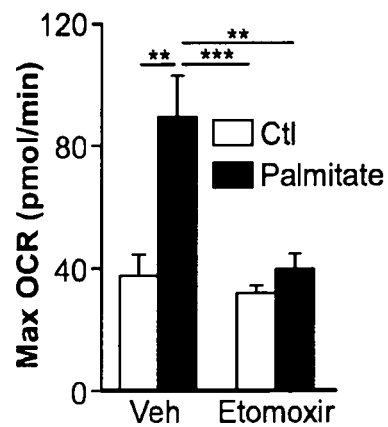
FIG. 2B depicts a bar graph showing maximal OCR of WT retinas provided with long-chain fatty acid (FA) palmitate or control (Ctl: bovine serum albumin or BSA) in the presence or absence of FA oxidation inhibitor, etomoxir (40 μM); n=6-8 retinas.
Figure 2C:
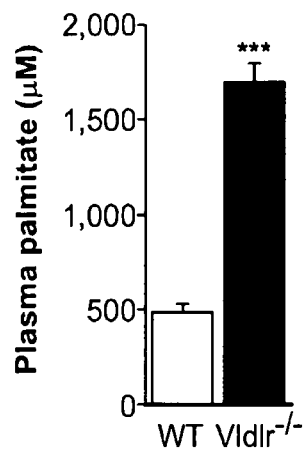
FIG. 2C depicts a bar graph showing circulating plasma palimate levels in WT and Vldlr$^{-/-}$ mice. N=7 WT, 13 Vldlr$^{-/-}$ mice plasma samples; (n=WT: 7, Vldlr$^{-/-}$:13 retinas P<0.0001).
Figure 2D:
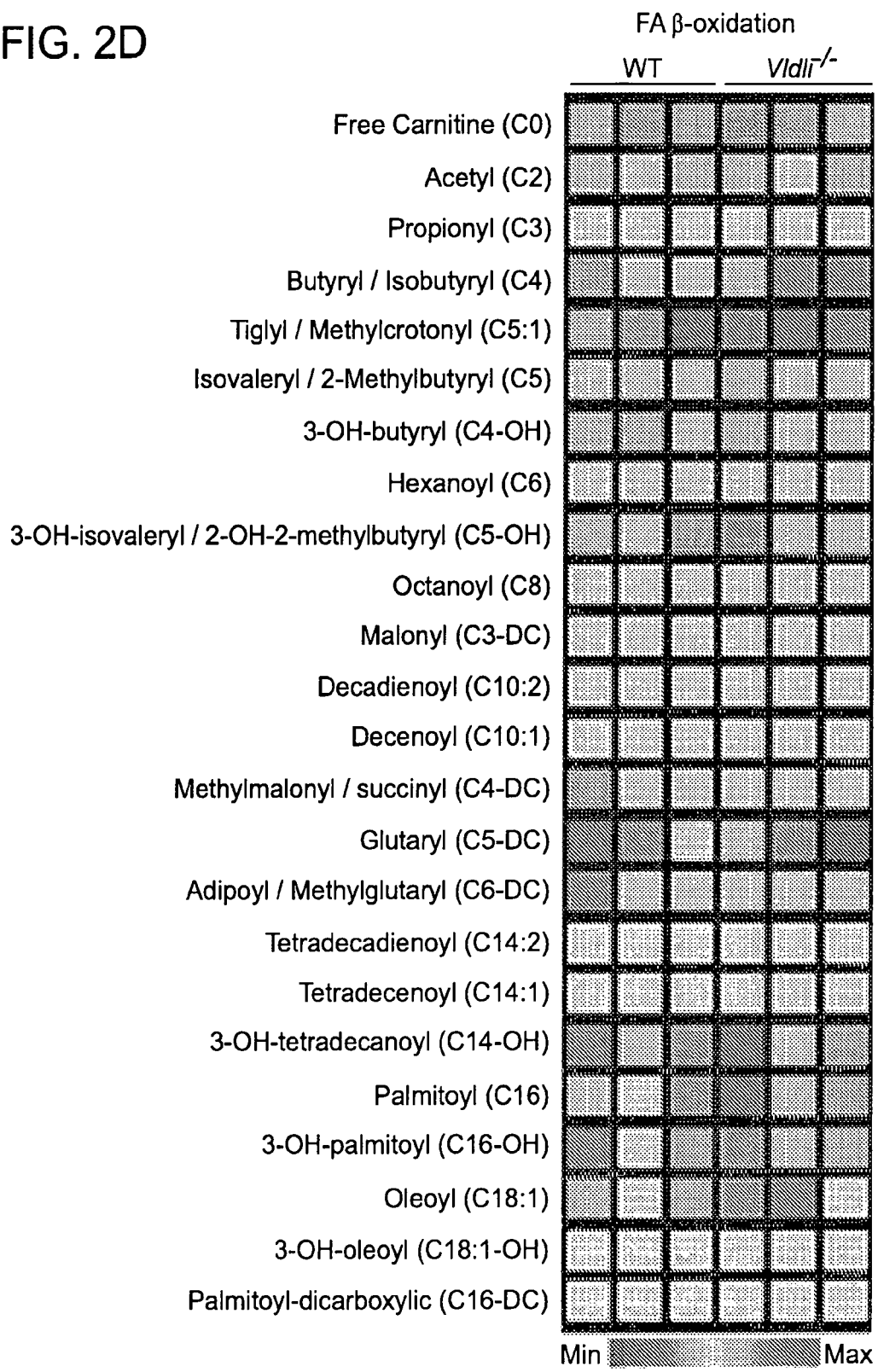
FIG. 2D depicts a heat map showing a metabolite array of FA β-oxidation levels measured by LC/MS/MS; n=3 animal retinas.
Figure 2E:
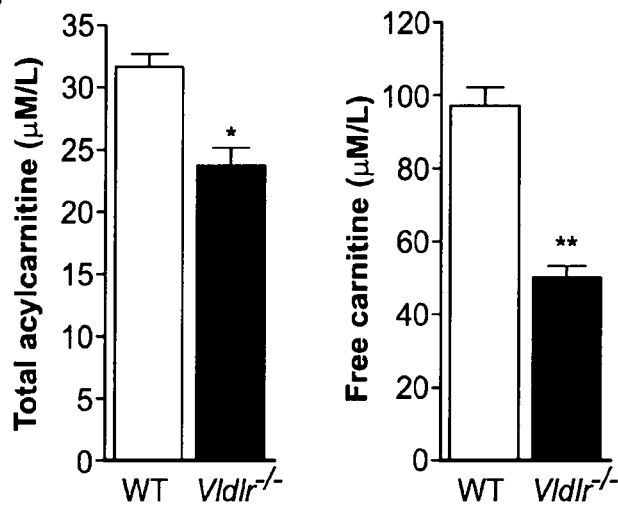
FIG. 2E depicts a bar graph showing total acylcarnitine and free carnitine levels (P=0.0014) measured by LC/MS/MS; n=3 animal retinas.
Figure 2F:
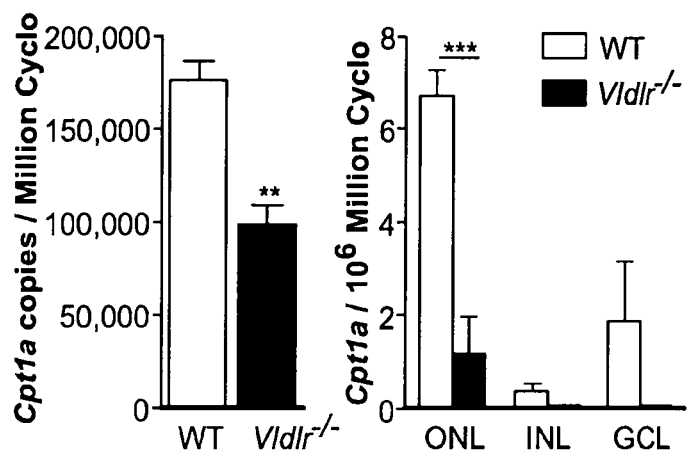
FIG. 2F depicts bar graphs showing that Cpt1a mRNA of intact retinas (left: P=0.0052) laser capture microdissection (LCM) retinal layers by qRT-PCR. ONL: outer nuclear; INL: inner nuclear (photoreceptors) and GCL: ganglion cell layers; n=3 animal retinas.
Figure 2G:
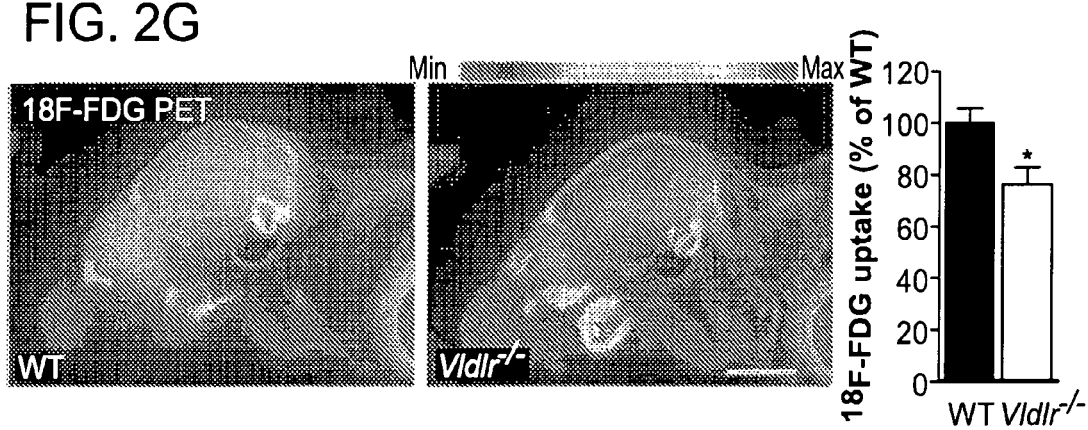
FIG. 2G depicts images and a bar graph showing that $^{18}$F-FDG microPET/CT scan revealed decreased glucose uptake in Vldlr$^{-/-}$ retinas, confirmed by retinal gamma radioactivity counts; Scale; 4 mm, n=22 WT, 12 Vldlr$^{-/-}$ retinas; P=0.0116.

In view of the possible role of Vldlr in retinal lipid energy metabolism, retinal FA uptake was quantified. Vldlr as reported was highly expressed in retinal photoreceptors (FIG. 7A) (Hu, W., et al *Invest Ophthalmol Vis Sci* 49, 407-415 (2008)). Retinal mid/long-chain FA uptake was reduced in Vldlr$^{-/-}$ retinas. Serum turbidity reflected higher circulating lipid levels (FIGS. 7B and 7C). Triglycerides and mid/long-chain FA plasma levels (particularly palmitate) were elevated in Vldlr$^{-/-}$ mice (FIG. 6C, and FIGS. 7D and 7E). Importantly, the process of FA β-oxidation of lipids in mitochondria to produce acetyl-CoA was suppressed (FIG. 6D). In Vldlr$^{-/-}$ retinas, total acylcarnitine and free carnitine levels were reduced (FIG. 6E). Low cytosolic FA levels were associated with decreased peroxisome proliferative activated receptor (PPARα) expression (Lefebvre, P., et al., *J Clin Invest* 116, 571-580 (2006)), mainly in Vldlr$^{-/-}$ photoreceptors (FIGS. 8A and 8B). PPARα is a key regulator of several steps of FA β-oxidation (Lefebvre, P., et al., *J Clin Invest* 116, 571-580 (2006)); including Cpt1a that mediates internalization of FA into mitochondria (FIG. 6B). Cpt1a was enriched in WT but suppressed in Vldlr$^{-/-}$ photoreceptors (FIG. 2F). A selective PPARα agonist (WY16463) used to enhance FA β-oxidation (Nakamura, M. T., et al., *Prog Lipid Res* 53, 124-144 (2014)) reduced RAP-like lesions in Vldlr$^{-/-}$ retina (FIG. 8C). Providing photoreceptor (661W) cells with palmitate alone or with PPARα agonist (GW9578) further increased mitochondrial respiration by FA β-oxidation and not via uncoupling, since etomoxir abrogated the increase in respiration (FIGS. 9A-9D). Extracellular acidification rates, reflecting lactate production from glycolysis, were not detectably affected by a PPARα agonist (FIGS. 9E and 9F). Further exploration of the role of PPARα in metabolic signaling in neovascular eye disease is warranted. Collectively, the findings indicate that lipids are s an energy substrate retina, challenging the current dogma that glucose is the only fuel of photoreceptors.

A compensatory upsurge in glucose uptake was expected to mitigate FA deficiency in Vldlr$^{-/-}$ retinas. Surprisingly, retinal glucose uptake ($^{18}$F-FDG) was assessed by positron emitting tomography (PET) and retinal $^{18}$F-FDG counts was reduced compared to WT (FIG. 2G and video data obtained showing that FFA1 dictated glucose uptake in Vldlr$^{-/-}$ retina, where $^{18}$F-FDG microPET/CT scan compared glucose uptake simultaneously in WT, Vldlr$^{-/-}$, Vldlr$^{-/-}$/

Figure 2H:
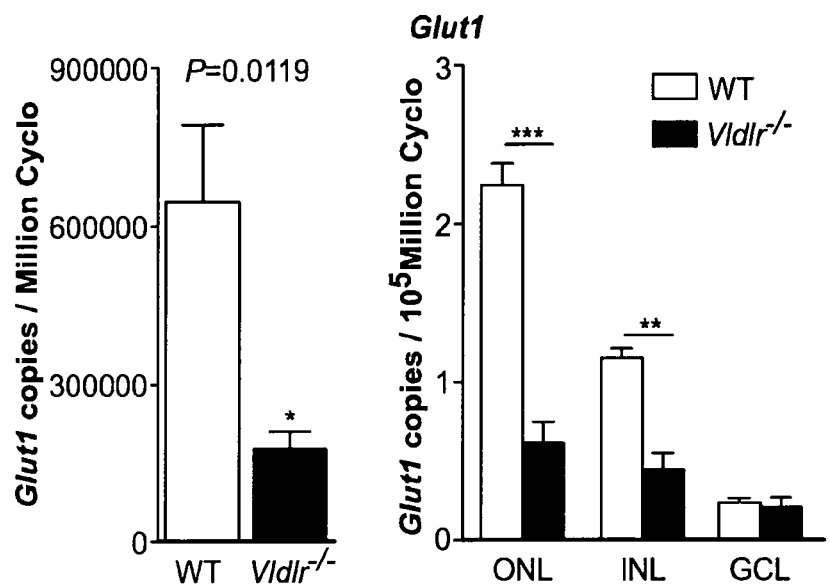
FIG. 2H depicts a bar graph showing that Glut1 mRNA (expression in intact retinas left, n=9 WT; 12 Vldlr$^{-/-}$ retinas; P=0.0119) and retinal layers (right) by LCM and qRT-PCR (n=3 retinas) (Two-tailed Student t-test (FIGS. 2C-2F and FIGS. 2G-2I) and one-way ANOVA with Tukey post-hoc analysis (FIGS. 2B, 2F, and 2H); * P<0.05,  P<0.01, * P<0.001.
Figure 2I:
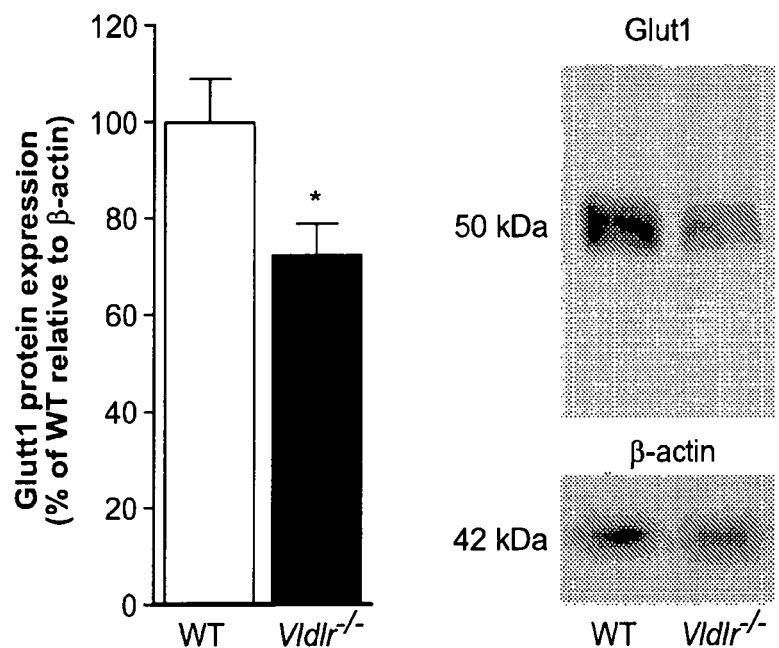
FIG. 2I depicts a bar graph and blot showing that Glut1 protein expression of intact WT and n Vldlr$^{-/-}$ retina; n=6 retinas P=0.03; results are presented as mean±SEM two-tailed Student t-test (FIGS. 2C-2F and FIGS. 2G-2I) and one-way ANOVA with Tukey post-hoc analysis (FIGS. 2B, 2F, and 2H); *P<0.05, P<0.01, *P<0.001.

Ffar1$^{-/-}$ and Ffar1$^{-/-}$ mice (data not shown)), as was GLUT1 expression of the major retinal glucose transporter Glut1 (FIGS. 2H and 2I), particularly in Vldlr$^{-/-}$ photoreceptors (FIG. 2H). In accord, carbohydrate metabolism was the most significantly regulated pathway on a gene microarray comparing Vldlr$^{-/-}$ to WT retinas (FIG. 10A). The suppression of pyruvate kinase (Pkm2), a critical enzyme of glycolysis was identified by the array and confirmed by qRT-PCR (FIG. 10B). Glut3 and 4 were not regulated (FIG. 10C). Hence, Vldlr$^{-/-}$ retinas possessed both lipid and glucose uptake deficiencies (FIGS. 2A-2I), consistent with a generalized energy shortage (FIGS. 1A-1E).

Example 4: Screening of Fatty Acid Sensing G-Protein Coupled Membrane Receptors

Figure 3A:
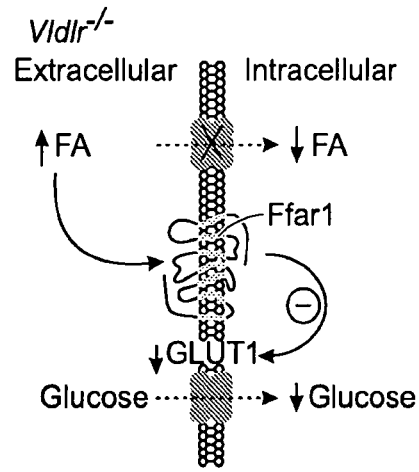
FIG. 3A depicts a schematic showing that FFA1 modulates retinal glucose uptake and RAP. Decreased lipid uptake in Vldlr$^{-/-}$ retina increased extracellular mid/long chain FA, the agonist of lipid sensor FFA1, which was associated with reduced Glut1 expression.
Figure 3B:
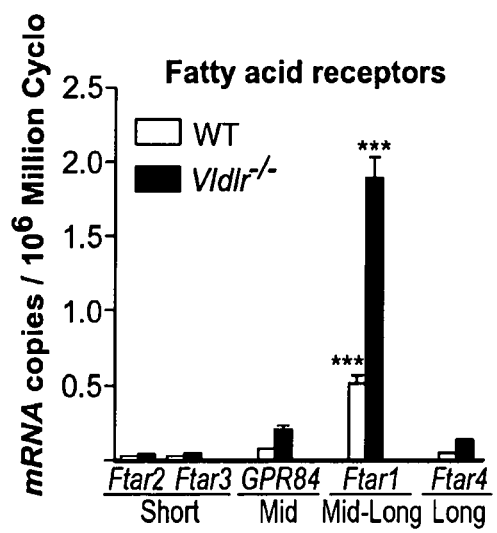
FIG. 3B depicts a bar graph showing that expression of FA sensing GPCR in WT and Vldlr$^{-/-}$ intact retinas.
Figure 3C:
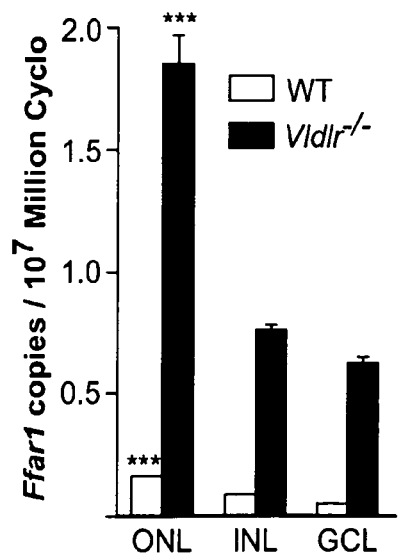
FIG. 3C depicts a bar graph showing that Ffar distribution in retinal layers by LCM (qRT-PCR). ONL: outer nuclear layer, INL: inner nuclear layer, GCL: ganglion cell layer; n=3 animal retinas; FFA1 agonist GW9508.
Figure 3D:
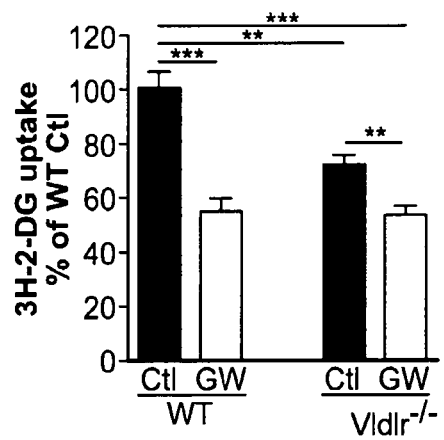
FIG. 3D depicts a bar graph showing that glucose uptake ($^3$H-2-DG tracer) (n=Ctl: 5-8 ctl, GW: 9-16 GW-treated retinas).
Figure 3E:
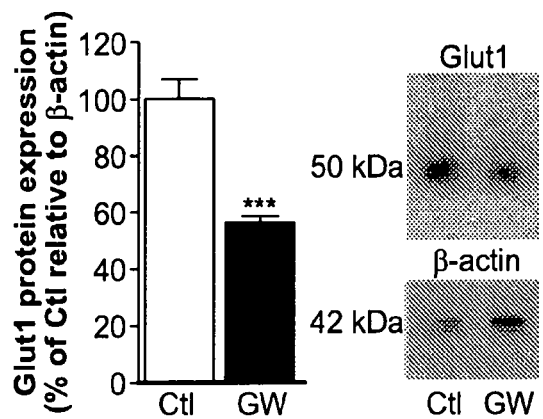
FIG. 3E depicts a bar graph and a blot showing that FFA1 agonist GW9508 agonist Glut1 protein expression (n=12 retinas; P<0.0001).
Figure 3F:
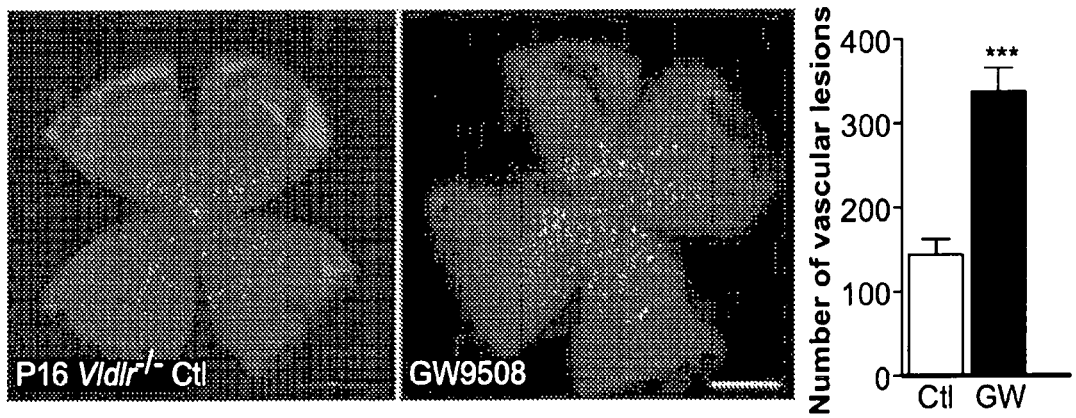
FIG. 3F depicts images and a bar graph showing that the number of RAP-like pathologic vascular lesions at P16 in WT and in Vldlr$^{-/-}$ mice.
Figure 3G:
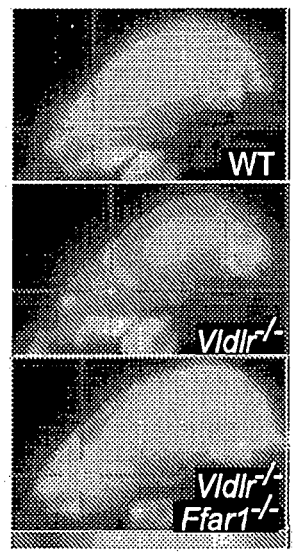
FIG. 3G depicts images showing that Ffar1 deletion in Vldlr$^{-/-}$ mice (Vldlr$^{-/-}$/Ffar1$^{-/-}$) reestablished glucose uptake ($^{18}$F-FDG; n=4 retinas; scale: 4 mm, GW: n=11 vehicle ctl: n=7, P=0.0002)).
Figure 3H:
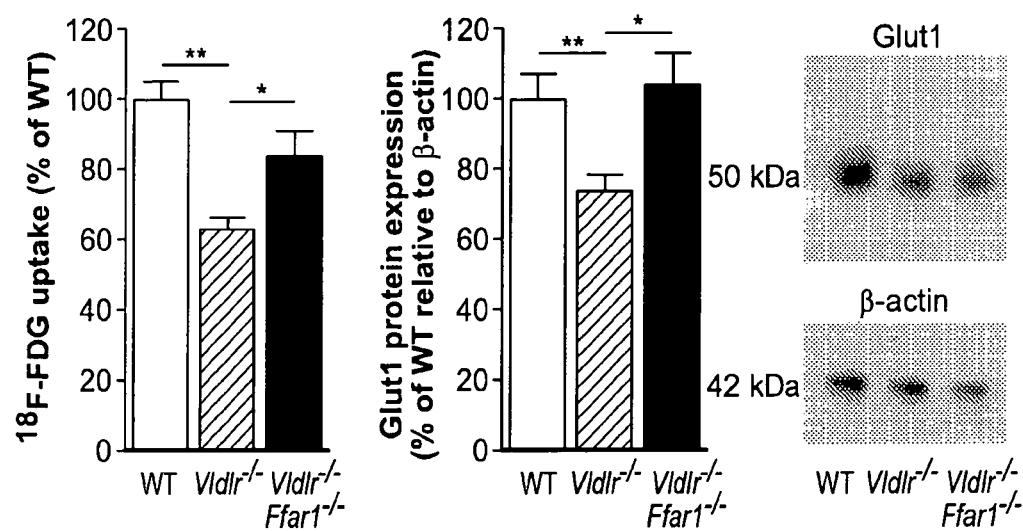
FIG. 3H depicts bar graphs and a blot showing that Ffar1 deletion in Vldlr$^{-/-}$ mice (Vldlr$^{-/-}$/Ffar1$^{-/-}$) increased Glut1 protein expression to WT levels (n=WT:10, others 9 retinas).
Figure 3I:
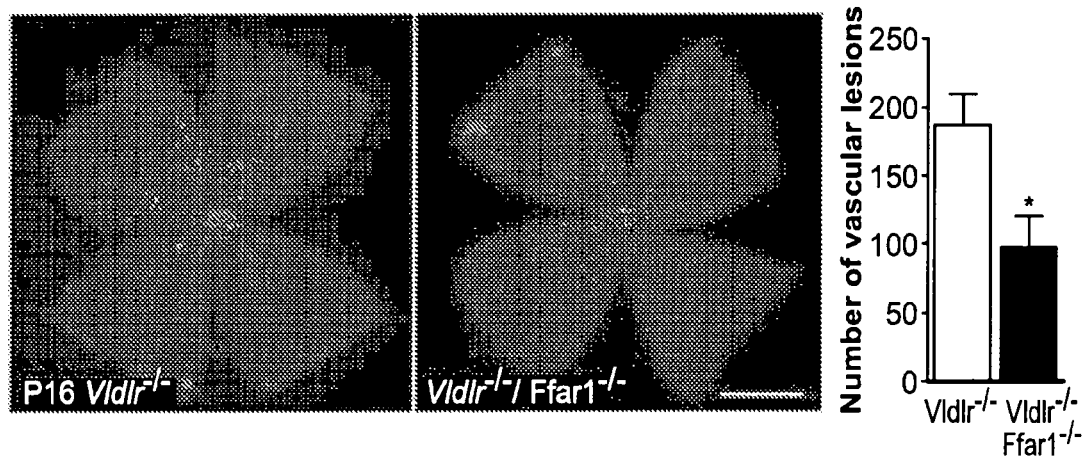
FIG. 3I depicts images and a bar graph showing that Ffar1 deletion in Vldlr$^{-/-}$ mice (Vldlr$^{-/-}$/Ffar1$^{-/-}$) reduced the number of RAP-like pathologic vascular lesions of WT (no lesions) and Vldlr$^{-/-}$ mice compared to littermate Vldlr$^{-/-}$/

An abundance of lipids in Vldlr$^{-/-}$ serum was postulated to signal through lipid sensors to reduce glucose uptake and help control fuel supply to the retina (FIG. 3A). Known FA sensing G-protein coupled membrane receptors (GPCR) in retina were screened. FFA1 was the most abundantly expressed FA receptor in WT and increased further in Vldlr$^{-/-}$ retinas, particularly in photoreceptors (FIGS. 3B and 3C). FFA1, first discovered in the pancreas (Itoh, Y., et al. *Nature* 422, 173-176 (2003)), governs glucose transport and insulin secretion (β-islet cells) (Kebede, M., et al. *Diabetes* 57, 2432-2437 (2008), and Alquier, T., et al. *Diabetes* 58, 2607-2615 (2009)). High pancreatic FFA1 expression suppressed expression of the main endocrine pancreas glucose transporter, Glut2 (Steneberg, P., et al., *Cell Metabolism* 1, 245-258 (2005)). Ffar1 has also been localized in brain, where its function is not well defined Honoré, J.-C., et al. *Arterioscler Thromb Vasc Biol* 33, 954-961 (2013)), and Briscoe, C. P., et al. *The J Biol Chem* 278, 1130311311 (2003)). In WT and Vldlr$^{-/-}$ retinas a FFA1 agonist (GW9508) was identified that suppressed the expression of Glut1 (Gospe, S. M., et al. *J Cell Sci* 123, 3639-3644 (2010)) and retinal glucose uptake (FIG. 3D and FIG. 11A). Importantly, treatment with FFA1 agonist (GW9508) more than doubled the number of RAP-like lesions in Vldlr$^{-/-}$ retinas compared to controls (FIG. 3F). FFA1 binds lipids comprising more than 6 carbons Briscoe, C. P., et al. *The J Biol Chem* 278, 1130311311 (2003)). Vldlr$^{-/-}$ mice treated with FFA1 lipid agonists medium chain triglycerides (MCT; 8-10 carbons) (Briscoe, C. P., et al. *The Journal of biological chemistry* 278, 1130311311 (2003)) or a second FFA1 selective agonist TAK-875 (Naik, H., et al. *J Clin Pharmacol* 52, 1007-1016 (2012)) increased Glut1 suppression and more RAP-like lesions versus controls (FIGS. 12A-12C). Deletion of Ffar1 in Vldlr$^{-/-}$ mice raised retinal glucose uptake (FIG. 3G and video data as described above (data not shown)) and Glut1 expression towards WT and Ffar1$^{-/-}$ levels (FIG. 3H, and FIGS. 11B-11C), with fewer RAP-like lesions in Vldlr$^{-/-}$/Ffar1$^{-/-}$ mice (FIG. 3I). In vitro knock down of Ffar1 or treating cells with MEK/ERK inhibitor (PD98059) prevented Glut1 suppression by GW9508 in photoreceptors (661W; FIGS. 11D-11F). Therefore, Ffar1 may act as nutrient sensor, coupling mitochondrial metabolism with circulating substrate availability.

Example 5: Lipid/Glucose Fuel Insufficiency in Retina, can Drive Aberrant Angiogenesis in the Normally Avascular Photoreceptor Layer It was hypothesized that photoreceptors challenged by a dual glucose and lipid fuel substrate deficiency would signal to increase vascular supply, in an attempt to restore energy homeostasis (FIG. 4A). Hypoxia has been assumed to be the main driver of angiogenesis, but inadequate nutrient availability to tissue might also control blood vessel growth. A reduction in pyruvate levels, metabolic intermediates feeding into the Krebs (TCA) cycle from decreased glucose uptake and glycolysis (FIG. 4B) and also less acetylcarnitine from decreased FA uptake and β-oxidation (FIG. 4C) were identified as associated with reduced production of essential intermediates, such as α-ketoglutarate (α-KG was lower, FIG. 4D).

Together with oxygen, α-KG is a necessary co-activator of propyl-hydroxylase dehydrogenase (PHD) that tags HIF1α for degradation by proline hydroxylation (Kaelin, W. G. *Cold Spring Harb Symp Quant Biol* 76, 335-345 (2011)). Less hydroxyproline was detected in Vldlr$^{-/-}$ retinas, consistent with reduced PHD activity (FIG. 4E). Indeed, reduction in retinal glucose uptake by FFA1 agonist GW9508 and glucose starvation in photoreceptors (661W) was associated with Hif1α stabilization (FIGS. 13A-13C) and Vegfa secretion (FIGS. 13D and 13E). In vivo, Hif1α stabilization (FIG. 4F) in Vldlr$^{-/-}$ photoreceptors (FIG. 4G) was associated with Vegfa production (FIGS. 4H and 4I). Deletion of Ffar1 in Vldlr$^{-/-}$ retinas suppressed HIFα stabilization and Vegfa secretion (FIGS. 4F and 4H), thereby leading to fewer vascular lesions (FIG. 3I). Consistent with the previous results Hua, J., et al. *Investigative ophthalmology & visual science* 52, 2809-2816 (2011)), mice engineered to secrete Vegfa in photoreceptors developed retinal angiomatous proliferation comparable to Vldlr$^{-/-}$ mice (Ohno-Matsui, K., et al. *The American journal of pathology* 160, 711-719 (2002)); Vegfa from photoreceptors was therefore sufficient to promote RAP-like lesions. Importantly, oxidative stress associated with an energy crisis likely also directly stabilized Hif1α and promoted Vegfa secretion in Vldlr$^{-/-}$ photoreceptors (Dorrell, M. I., et al. *J Clin Invest* 119, 611-623 (2009), Chen, Y., et al. *Microvasc Res* 78, 119-127 (2009), and Zhou, X., et al., *PloS One* 6, e16733 (2011)), potentially contributing to vascular lesions. However, macrophages, often implicated in the etiology of AMD, were not associated with the onset of development of nascent RAP-like lesions, surrounding only mature vascular lesions (FIGS. 14A-14D). Translating these findings to human disease, higher vitreous VEGF levels were detected in AMD/RAP human subjects compared to controls (macular hole; FIG. 4J). These findings indicated that lipid/glucose fuel insufficiency in retina, in part through reduction of Krebs cycle metabolite α-KG, could drive aberrant angiogenesis in the normally avascular photoreceptor layer.

In the retina, the ability to use both lipids and glucose as fuel might be beneficial during periods of high fuel need or fuel deprivation. Fasting liberates FA from adipose tissue that is used by high-energy consuming organs capable of FA β-oxidation, such as heart, and perhaps retina (FIGS. 2A-2F, FIGS. 6A-6C, and FIGS. 9A-9D). Indeed, FA β-oxidation disorders were previously identified as associated with retinopathy (Fletcher, et al., *Molecular Genetics and Metabolism* 106, 18-24 (2012)). Tissues that use lipid as fuel curb glucose uptake during starvation (Mantych, G. J et al., *Endocrinology* 133, 600-607 (1993), and Ferrannini, E., et al. *J Clin Invest* 72, 1737-1747 (1983)). The capacity to sense nutrient availability and adapt fuel uptake could improve metabolic efficiency.

G-protein coupled receptors (GPCR) are known membrane sensors of amino acids, glucose and lipids (Wauson, E. M. et al. *Mol Endocrinol* 27, 1188-1197 (2013)). Here, FFA1 was shown to be a metabolic sensor of FA availability, which controls glucose entry into the retina (FIGS. 3A-3I). Long-term suppression of glucose entry by FFA1 in photoreceptors (perhaps secondary to circulating lipids) likely contributed to age-related mitochondrial dysfunction in AMD or MacTel. Retinal effects of FFA1 agonists considered for the treatment of type II diabetes should be carefully monitored, particularly in older individuals at increased risk of AMD.

Summary

Mitochondrial metabolism may contribute to pathological angiogenesis in other diseases, such as cancer. To provide building blocks for proliferation, tumors promote angiogenesis at the cost of efficient ATP production by the Warburg effect (Warburg, O. *Science* 123, 309-314 (1956)). In suppressing mitochondrial oxidative phosphorylation, tumor cells may generate less α-KG (Zhao, S., et al. *Science* 324, 261-265 (2009)) (or accumulate competing metabolites) (Kaelin, W. G. *Cold Spring Harb Symp Quant Biol* 76, 335-345 (2011)). This inhibits prolyl-hydroxylase dehydrogenase (PHD) with ensuing HIF1α stabilization, driving tumor angiogenesis required for growth. The findings indicate the importance of mitochondrial fuel starvation as a driver of angiogenesis, matching energy demands with vascular supply. With a decline in mitochondrial function with age, this process may contribute to pathological angiogenesis in diseases of aging retina.

In summary, lipid uptake and lipid β-oxidation are curtailed in Vldlr$^{-/-}$ retinas. Increased circulating FA can activate FFA1, associated with decreased retinal glucose uptake and decreased Kreb cycle intermediate α-KG. Hifα is stabilized and Vegfa secreted by Vldlr$^{-/-}$ photoreceptors, giving rise to pathologic RAP-like neovessels. This study uncovered three important novel mechanisms contributing to retinal physiology and neovascular AMD/RAP:

(1) lipid β-oxidation is an energy source for the retina, (2) FFA1 is an important nutrient sensor of circulating lipids that controls retinal glucose entry to match mitochondrial metabolism with available fuel substrates, and (3) nutrient scarcity is a driver of retinal pathological angiogenesis.

These pathways may be important for discovery of new therapeutics.

Example 6: Use of FFA1 Inhibitors to Treat Neural Cell (e.g., Retinal Cell) Diseases or Disorders In this example, a subject having or at risk of developing a neural cell (e.g., retinal cell) disease or disorder characterized by angiogenesis (e.g., a subject having or at risk of RAP vascular lesions, e.g., a subject having or at risk of MacTel and/or AMD) is administered a pharmaceutical composition comprising a FFA1 inhibitor. Prevention and/or improvement of the neural cell (e.g., retinal cell) disease or disorder characterized by angiogenesis is monitored both before and after administration of the FFA1 inhibitor to the subject. The FFA1 inhibitor (e.g., RNAi and/or small molecule) is administered systemically or locally to the subject (e.g., via intraocular injection to a subject). Prophylactic and/or therapeutic efficacy of the FFA1 inhibitor in the subject is thereby identified.

Example 7: Identification of Novel FFA1 Inhibitors

In this example, photoreceptor cells (e.g., 661W cells) are grown in vitro, optionally in an array format. Cells (optionally having a mutation or deletion of the very low-density lipoprotein receptor (Vldlr) gene) are contacted with libraries of test compounds, and cellular glucose uptake is monitored. Test compounds that reproducibly affect a significant increase in glucose uptake are thereby identified as candidate novel inhibitors of FFA1.

Contemplated assays for identification of new FFA1 inhibitors include radioactive calorimetric assays, as well as non-radioactive calorimetric assays to measure glucose uptake. The assays are optionally optimized for high throughput analysis. For example, a non-radioactive assay includes a colorimetric glucose uptake assay kit (e.g., Abcam product number ab136955). Additionally, a glucose uptake cell-based assay kit (Cayman chemical Item No 600470) is used to measure glucose uptake using a fluorescent deoxyglucose analog. In yet another example, the FFA1 inhibitors are identified through the cell surface representation of the glucose transporter, Glut1 (e.g., ELISA-based assays and/or gene expression assays).

Example 8: Use of FFA1 Inhibitors to Treat Neurodegeneration

In this example a subject having or at risk of developing neurodegeneration (characterized by a loss in function of neurons and also including death of neurons) is administered a pharmaceutical composition comprising a FFA1 inhibitor. Prevention and/or improvement of the neurodegeneration is monitored both before and after administration of the FFA1 inhibitor to the subject. Prophylactic and/or therapeutic efficacy of the FFA1 inhibitor in the subject is thereby identified.

Example 9: Use of FFA1 Inhibitors to Treat Cancer

In this example, a subject having or at risk of developing cancer is administered a pharmaceutical composition comprising a FFA1 inhibitor. Prevention and/or improvement of the cancer is monitored both before and after administration of the FFA1 inhibitor to the subject. Prophylactic and/or therapeutic efficacy of the FFA1 inhibitor in the subject is thereby identified. In some examples, the inhibitors alter the metabolism of malignant cells, thereby treating the subject.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating angiogenesis in neural cells of a subject and/or treating retinal angiomatous proliferation (RAP) in a subject, the method comprising:
   (a) identifying a subject having or at risk of neural cell angiogenesis and/or having or at risk of developing RAP; and
   (b) administering GW1100 to the subject, thereby treating angiogenesis in the neural cells of the subject and/or treating RAP in the subject.

2. The method of claim 1, wherein the neural cells are retinal cells, optionally photoreceptor cells.

3. A method for treating retinal angiomatous proliferation (RAP) vascular lesions in a subject, the method comprising:
   (a) identifying a subject having or at risk of developing RAP vascular lesions; and
   (b) administering GW1100 to the subject, thereby treating RAP vascular lesions in the subject.

4. The method of claim 1, wherein the subject has macular telangiectasia (MacTel) or neovascular age-related macular degeneration (AMD).

5. The method of claim 1, wherein the cells of the subject are impaired for lipid uptake, as compared to the cells of an appropriate control subject.

6. The method of claim 1, wherein the subject has dyslipidemia or mitochondrial dysfunction.

7. The method of claim 1, wherein the GW1100 is administered to the eye of the subject.

8. The method of claim 7, wherein GW1100 is administered by intravitreal injection.

9. The method of claim 1, wherein administering GW1100 enhances GLUT1 expression in the retinal cells of the subject.

10. The method of claim 3, wherein the subject has macular telangiectasia (MacTel) or neovascular age-related macular degeneration (AMD).

11. The method of claim 3, wherein the cells of the subject are impaired for lipid uptake, as compared to the cells of an appropriate control subject.

12. The method of claim 3, wherein the subject has dyslipidemia or mitochondrial dysfunction.

13. The method of claim 3, wherein the GW1100 is administered to the eye of the subject.

14. The method of claim 3, wherein GW1100 is administered by intravitreal injection.

15. The method of claim 3, wherein administering GW1100 enhances GLUT1 expression in the retinal cells of the subject.

* * * * *

UNITED STATES PATENT AND TRADEMARK OFFICE
CERTIFICATE OF CORRECTION

| | |
|---|---|
| PATENT NO. | : 11,583,528 B2 |
| APPLICATION NO. | : 15/999535 |
| DATED | : February 21, 2023 |
| INVENTOR(S) | : Lois Smith et al. |

It is certified that error appears in the above-identified patent and that said Letters Patent is hereby corrected as shown below:

In the Specification

Column 1, Line 14, please replace the paragraph titled "STATEMENT REGARDING FEDERALLY SPONSORED RESEARCH OR DEVELOPMENT" with the following paragraph:
FEDERALLY SPONSORED RESEARCH
This invention was made with government support under Grant Numbers EY024864, EY017017, EY022275, EY024963, and HD018655, awarded by the National Institutes of Health. The Government has certain rights in the invention.

Signed and Sealed this
Thirtieth Day of May, 2023

Katherine Kelly Vidal
*Director of the United States Patent and Trademark Office*

SEQUENCE LISTING

<160> NUMBER OF SEQ ID NOS: 34

<210> SEQ ID NO 1
<211> LENGTH: 20
<212> TYPE: DNA

```
<213> ORGANISM: Homo sapiens

<400> SEQUENCE: 1
catgtcaagc cagaggaaga                                              20

<210> SEQ ID NO 2
<211> LENGTH: 20
<212> TYPE: DNA
<213> ORGANISM: Homo sapiens

<400> SEQUENCE: 2
tggtaggaga gcagcacctt                                              20

<210> SEQ ID NO 3
<211> LENGTH: 19
<212> TYPE: DNA
<213> ORGANISM: Homo sapiens

<400> SEQUENCE: 3
cagacgccac tgtcgcttt                                               19

<210> SEQ ID NO 4
<211> LENGTH: 23
<212> TYPE: DNA
<213> ORGANISM: Homo sapiens

<400> SEQUENCE: 4
tgtctttgga actttgtctg caa                                          23

<210> SEQ ID NO 5
<211> LENGTH: 22
<212> TYPE: DNA
<213> ORGANISM: Homo sapiens

<400> SEQUENCE: 5
cagttcggct ataacactgg tg                                           22

<210> SEQ ID NO 6
<211> LENGTH: 19
<212> TYPE: DNA
<213> ORGANISM: Homo sapiens

<400> SEQUENCE: 6
gcccccgaca gagaagatg                                               19

<210> SEQ ID NO 7
<211> LENGTH: 22
<212> TYPE: DNA
<213> ORGANISM: Homo sapiens

<400> SEQUENCE: 7
ctttcttctc ggatgtcaag gg                                           22

<210> SEQ ID NO 8
<211> LENGTH: 19
<212> TYPE: DNA
<213> ORGANISM: Homo sapiens

<400> SEQUENCE: 8
gatgagcccc agaacggtg                                               19

<210> SEQ ID NO 9
<211> LENGTH: 23
```

-continued

```
<212> TYPE: DNA
<213> ORGANISM: Homo sapiens

<400> SEQUENCE: 9
ccttcgctct ctatgtatct gcc                                           23

<210> SEQ ID NO 10
<211> LENGTH: 23
<212> TYPE: DNA
<213> ORGANISM: Homo sapiens

<400> SEQUENCE: 10
ggctaacaag ttcaatggaa agc                                           23

<210> SEQ ID NO 11
<211> LENGTH: 20
<212> TYPE: DNA
<213> ORGANISM: Homo sapiens

<400> SEQUENCE: 11
ttctgagcgt ggcctatcca                                               20

<210> SEQ ID NO 12
<211> LENGTH: 21
<212> TYPE: DNA
<213> ORGANISM: Homo sapiens

<400> SEQUENCE: 12
agactacact gaccagacca g                                             21

<210> SEQ ID NO 13
<211> LENGTH: 21
<212> TYPE: DNA
<213> ORGANISM: Homo sapiens

<400> SEQUENCE: 13
tgctacgaga acttcaccca a                                             21

<210> SEQ ID NO 14
<211> LENGTH: 21
<212> TYPE: DNA
<213> ORGANISM: Homo sapiens

<400> SEQUENCE: 14
cacacgaagc gccaataaca g                                             21

<210> SEQ ID NO 15
<211> LENGTH: 21
<212> TYPE: DNA
<213> ORGANISM: Homo sapiens

<400> SEQUENCE: 15
ccagcgaggg gatttcatct g                                             21

<210> SEQ ID NO 16
<211> LENGTH: 22
<212> TYPE: DNA
<213> ORGANISM: Homo sapiens

<400> SEQUENCE: 16
gcttctgacg aatcaccttc ca                                            22

<210> SEQ ID NO 17
```

-continued

```
<211> LENGTH: 20
<212> TYPE: DNA
<213> ORGANISM: Homo sapiens

<400> SEQUENCE: 17
atcgggcgat gcaaccgagc                                                 20

<210> SEQ ID NO 18
<211> LENGTH: 23
<212> TYPE: DNA
<213> ORGANISM: Homo sapiens

<400> SEQUENCE: 18
agagggccat caaggtacag gca                                             23

<210> SEQ ID NO 19
<211> LENGTH: 20
<212> TYPE: DNA
<213> ORGANISM: Homo sapiens

<400> SEQUENCE: 19
agagccccat ctgtcctctc                                                 20

<210> SEQ ID NO 20
<211> LENGTH: 22
<212> TYPE: DNA
<213> ORGANISM: Homo sapiens

<400> SEQUENCE: 20
actggtagtc tgcaaaacca aa                                              22

<210> SEQ ID NO 21
<211> LENGTH: 21
<212> TYPE: DNA
<213> ORGANISM: Homo sapiens

<400> SEQUENCE: 21
tccatcgtca acaaagacgg g                                               21

<210> SEQ ID NO 22
<211> LENGTH: 21
<212> TYPE: DNA
<213> ORGANISM: Homo sapiens

<400> SEQUENCE: 22
acttgggctc aatgatgtca c                                               21

<210> SEQ ID NO 23
<211> LENGTH: 20
<212> TYPE: DNA
<213> ORGANISM: Homo sapiens

<400> SEQUENCE: 23
tcgctgatgc actgcctatg                                                 20

<210> SEQ ID NO 24
<211> LENGTH: 21
<212> TYPE: DNA
<213> ORGANISM: Homo sapiens

<400> SEQUENCE: 24
gagaggtcca cagagctgat t                                               21
```

-continued

```
<210> SEQ ID NO 25
<211> LENGTH: 20
<212> TYPE: DNA
<213> ORGANISM: Homo sapiens

<400> SEQUENCE: 25
attggcctgt gttttcgcac                                                   20

<210> SEQ ID NO 26
<211> LENGTH: 20
<212> TYPE: DNA
<213> ORGANISM: Homo sapiens

<400> SEQUENCE: 26
cacagtgggg tcatctgcat                                                   20

<210> SEQ ID NO 27
<211> LENGTH: 20
<212> TYPE: DNA
<213> ORGANISM: Homo sapiens

<400> SEQUENCE: 27
tctcttgctc ttagtgatgg                                                   20

<210> SEQ ID NO 28
<211> LENGTH: 21
<212> TYPE: DNA
<213> ORGANISM: Homo sapiens

<400> SEQUENCE: 28
cttacaactg atattgctgg g                                                 21

<210> SEQ ID NO 29
<211> LENGTH: 22
<212> TYPE: DNA
<213> ORGANISM: Mus musculus

<400> SEQUENCE: 29
ggaaagttca agtgcagaag cg                                                22

<210> SEQ ID NO 30
<211> LENGTH: 22
<212> TYPE: DNA
<213> ORGANISM: Mus musculus

<400> SEQUENCE: 30
ggaatgccat atcaacgaat gc                                                22

<210> SEQ ID NO 31
<211> LENGTH: 22
<212> TYPE: DNA
<213> ORGANISM: Mus musculus

<400> SEQUENCE: 31
gggatctgca gtcaaatttg ta                                                22

<210> SEQ ID NO 32
<211> LENGTH: 22
<212> TYPE: DNA
<213> ORGANISM: Mus musculus

<400> SEQUENCE: 32
gatttaagac aagcgtataa ca                                                22
```

<210> SEQ ID NO 33
<211> LENGTH: 923
<212> TYPE: DNA
<213> ORGANISM: Homo sapiens

<400> SEQUENCE: 33

```
cggcggcccc atggacctgc ccccgcagct ctccttcggc ctctatgtgg ccgcctttgc      60
gctgggcttc ccgctcaacg tcctggccat ccgaggcgcg acggcccacg cccggctccg     120
tctcacccct agcctggtct acgccctgaa cctgggctgc tccgacctgc tgctgacagt     180
ctctctgccc ctgaaggcgg tggaggcgct agcctccggg gcctggcctc tgccggcctc     240
gctgtgcccc gtcttcgcgg tggcccactt cttcccactc tatgccggcg ggggcttcct     300
ggccgccctg agtgcaggcc gctacctggg agcagcctlc cccttgggct accaagcctt     360
ccggaggccg tgctattcct gggggggtgtg cgcggccatc tgggccctcg tcctgtgtca     420
cctgggtctg gtcttgggt tggaggctcc aggaggctgg ctggaccaca gcaacacctc     480
cctgggcatc aacacccgg tcaacggctc tccggtctgc ctggaggcct gggacccggc     540
ctctgccggc ccggcccgct tcagcctctc tctcctgctc ttttttctgc ccttggccat     600
cacagccttc tgctacgtgg gctgcctccg ggcactggcc cgctccggcc tgacgcacag     660
gcggaagctg cgggccgcct gggtggccgg cggggccctc ctcacgctgc tgctctgcgt     720
aggaccctac aacgcctcca acgtggccag cttcctgtac cccaatctag gaggctcctg     780
gcggaagctg ggctcatca cgggtgcctg gagtgtggtg cttaatccgc tggtgaccgg     840
ttacttggga aggggtcctg gcctgaagac agtgtgtgcg caagaacgc aaggggggcaa     900
gtcccagaag taacgccact gct                                             923
```

<210> SEQ ID NO 34
<211> LENGTH: 300
<212> TYPE: PRT
<213> ORGANISM: Homo sapiens

<400> SEQUENCE: 34

Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro

```
              165                 170                 175
Ala Ser Ala Gly Pro Ala Arg Phe Ser Leu Ser Leu Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220

Val Ala Gly Gly Ala Leu Leu Thr Leu Leu Cys Val Gly Pro Tyr
225                 230                 235                 240

Asn Ala Ser Asn Val Ala Ser Phe Leu Tyr Pro Asn Leu Gly Gly Ser
            245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285

Cys Ala Ala Arg Thr Gln Gly Gly Lys Ser Gln Lys
    290                 295                 300
```